(12) United States Patent
Yang

(10) Patent No.: US 11,786,606 B2
(45) Date of Patent: Oct. 17, 2023

(54) SITE-SPECIFIC QUANTITATION OF DRUG CONJUGATIONS

(71) Applicant: Regeneron Pharmaceuticals, Inc., Tarrytown, NY (US)

(72) Inventor: Xiangkun Yang, Medford, MA (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 254 days.

(21) Appl. No.: 17/074,387

(22) Filed: Oct. 19, 2020

(65) Prior Publication Data

US 2021/0154321 A1 May 27, 2021

Related U.S. Application Data

(60) Provisional application No. 63/043,756, filed on Jun. 24, 2020, provisional application No. 62/916,876, filed on Oct. 18, 2019.

(51) Int. Cl.
*A61K 47/68* (2017.01)
*G01N 33/68* (2006.01)

(52) U.S. Cl.
CPC ...... *A61K 47/6889* (2017.08); *A61K 47/6815* (2017.08); *A61K 47/6817* (2017.08); *G01N 33/6851* (2013.01)

(58) Field of Classification Search
None
See application file for complete search history.

(56) References Cited

FOREIGN PATENT DOCUMENTS

WO 2017151892 * 9/2017
WO WO2017/151892 A2 9/2017

OTHER PUBLICATIONS

A Beck et al: "Cutting-edge multi-level analytical and structural characterization of antibody-drug conjugates: present and future", Expert Review of Proteomics, vol. 16, No. 4, Apr. 3, 2019 (Apr. 3, 2019), pp. 337-362.
Jia Chen et al: "Development of a Native Nanoelectrospray Mass Spectrometry Method for Determination of the Drug-to-Antibody Ratio of Antibody-Drug Conjugates", Analytical Chemistry, vol. 85, No. 3, Feb. 5, 2013 (Feb. 5, 2013), pp. 1699-1704.
Santiago Esteban Farias et al: "Mass spectrometric characterization of transglutaminase based site-specific antibody-drug conjugates", Bioconjugate Chemistry, Dec. 20, 2013 (Dec. 20, 2013), XP055094950.

(Continued)

*Primary Examiner* — Karl J Puttlitz
(74) *Attorney, Agent, or Firm* — Kramer Levin Naftalis & Frankel LLP

(57) ABSTRACT

A method for site-specific quantitation or characterization of drug conjugations of antibody-drug conjugates using protease-assisted drug deconjugation, linker labelling and mass spectrometry, wherein the conjugation includes an attachment linked to a specific conjugation site of a partially conjugated peptide or protein in a sample. The method comprises cleaving a portion of the attachment to generate the peptide or protein containing a cleaved linker, adding a modified linker to an unconjugated conjugation site of the partially conjugated peptide or protein, and subsequently subjecting the sample to mass analysis to identify the peptide or protein containing the cleaved linker and/or the modified linker.

28 Claims, 50 Drawing Sheets

Specification includes a Sequence Listing.

(56) References Cited

OTHER PUBLICATIONS

Adamo Michael et al: "Drug-to-antibody determination for an antibody-drug-conjugate utilizing cathepsin B digestion coupled with reversed-phase high-pressure liquid chromatography analysis", Journal of Chromatography A, vol. 1481, Dec. 19, 2016 (Dec. 19, 2016), pp. 44-52.
Janin-Bussat Marie-Claire et al: "Characterization of antibody drug conjugate positional isomers at cysteine residues by peptide mapping LC-MS analysis", Journal of Chromatography B, vol. 981, Dec. 24, 2014 (Dec. 24, 2014), pp. 9-13, XP029190637.
Hernandez-Alba Oscar et al: "A Case Study to Identify the Drug Conjugation Site of a Site-Specific Antibody-Drug-Conjugate Using Middle-Down Mass Spectrometry", Journal of the American Society for Mass Spectrometry, vol. 30, No. 11, Aug. 19, 2019 (Aug. 19, 2019), pp. 2419-2429.
International Application No. PCT/US2020/056368, International Filing Date Oct. 19, 2020, International Search Report dated Feb. 10, 2021.

* cited by examiner

Gemtuzumab ozogamicin (Mylotarg®)

Trastuzumab emtansine (Kadcyla®)

Brentuximab vedotin (Adcetris®)

Formula I

Formula II

Formula III

Formula IV

Formula V

Formula VI

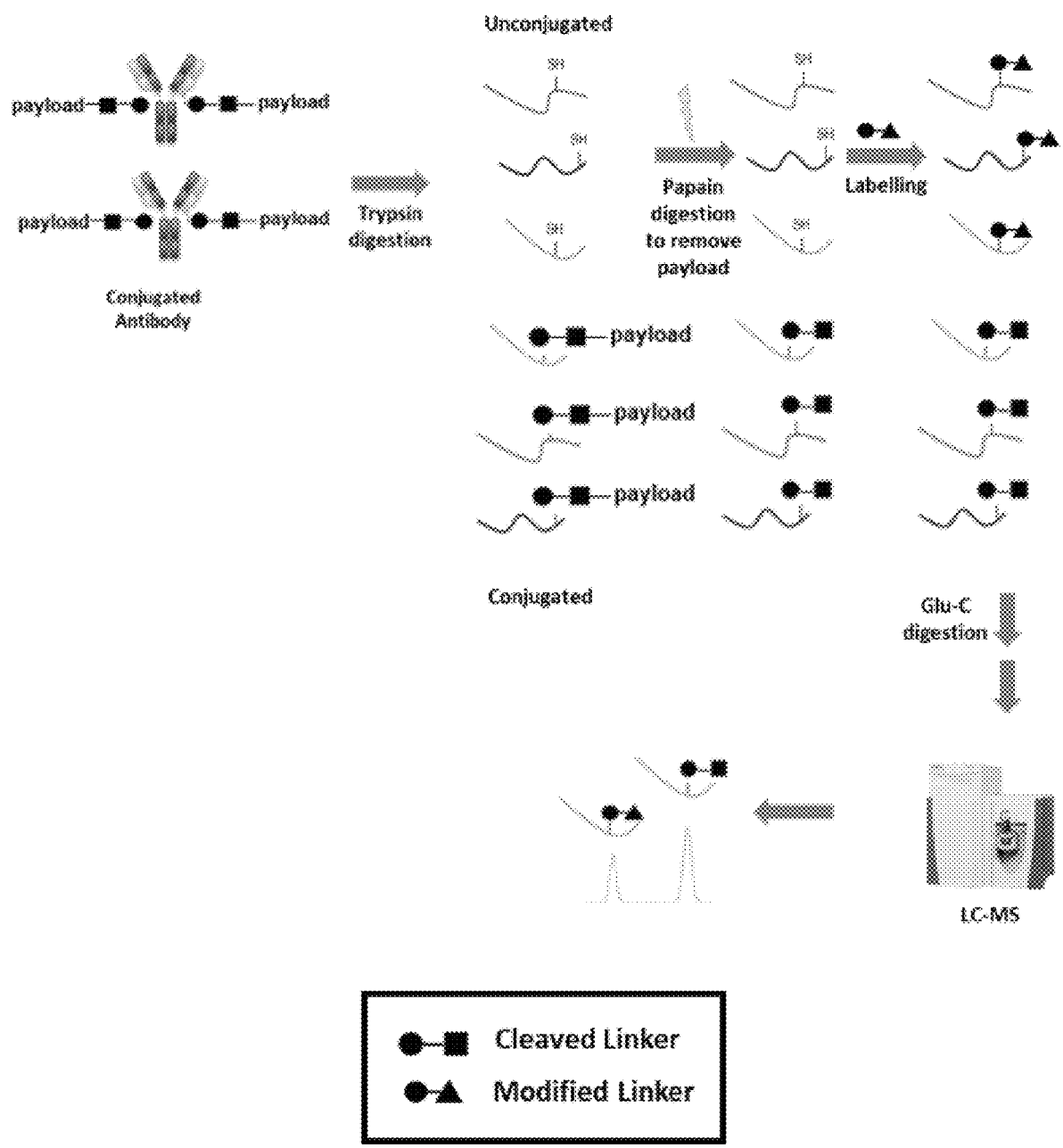

Multiple papain cleavage sites on the hinge region peptide:
TH↑T↑CPPCPAPE↑LL↑G↑GPSVFLFPPKPK

TH↑T↑CPPCPAPE↑L↑L↑G↑GPSVF↑L↑FPPKPK

FIG. 17

|  | MAB1-L19 (n=3) Low DAR (ESI, intact: 1.9) | | MAB1-L8 (n=3) High DAR (ESI, intact: 3.6) | |
| --- | --- | --- | --- | --- |
|  | Measured conjugation% | CV% | Measured conjugation% | CV% |
| GEC | 12.1 ± 0.1 | 0.9 | 24.0 ± 0.3 | 1.1 |
| SCDK | 23.1 ± 0.5 | 2.0 | 51.6 ± 0.6 | 1.2 |
| Hinge Region Peptides | 73.0 ± 0.4 | 0.6 | 95.0 ± 0.2 | 0.2 |
| DAR | 2.16 ± 0.01 | 0.5 | 3.41 ± 0.02 | 0.6 |

S C D K

MAB1-LK3 Papain:Substrate Ratio

FIG. 25

| Conjugation site | MAB1-LK3-L9 (ESI: 2.2) | | | | MAB1-LK1-L8 (ESI: 3.6) | | | |
| --- | --- | --- | --- | --- | --- | --- | --- | --- |
| | Intra-day (n=3) | | Inter-day (n=3 x 3/day) | | Intra-day (n=3) | | Inter-day (n=3 x 3/day) | |
| | Ratio | RSD% | Ratio | RSD% | Ratio | RSD% | Ratio | RSD% |
| GEC | 0.40 | 2.8% | 0.40 | 1.7% | 0.31 | 0.4% | 0.31 | 2.9% |
| SCDK | 0.41 | 3.4% | 0.43 | 4.5% | 0.58 | 0.9% | 0.57 | 0.9% |
| Hinge region (-CPPCPAPE-) | 0.49 | 1.5% | 0.48 | 2.1% | 0.88 | 0.9% | 0.89 | 4.0% |
| DAR | 2.61 | 2.4% | 2.63 | 1.8% | 3.54 | 0.8% | 3.56 | 2.6% |
| Hinge region peptide % (0 drug) | 71.3% | 0.5% | 71.8% | 0.7% | 39.8% | 1.3% | 39.2% | 4.2% |
| Hinge region peptide % (1 drug) | 8.2% | 0.7% | 8.3% | 1.0% | 32.9% | 0.7% | 32.3% | 1.5% |
| Hinge region peptide % (2 drug) | 20.5% | 1.7% | 20.0% | 2.5% | 27.3% | 1.1% | 28.4% | 6.9% |

SEQUENCE LISTING

```
<160> NUMBER OF SEQ ID NOS: 22

<210> SEQ ID NO 1
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Thr His Thr Cys Pro Pro Cys Pro Ala Pro Glu Leu Leu Gly Gly Pro
1               5                   10                  15

Ser Val Phe Leu Phe Pro Pro Lys Pro Lys
            20                  25

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Cys Pro Pro Cys Pro Ala Pro Glu
1               5

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3
```

```
Cys Pro Pro Cys Pro Ala Pro Glu Leu Leu
1               5                   10

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Cys Pro Pro Cys Pro Ala Pro Glu
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Thr Cys Pro Pro Cys Pro Ala Pro Glu
1               5

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Thr His Thr Cys Pro Pro Cys Pro Ala Pro Glu
1               5                   10

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ser Cys Asp Lys
1

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Thr His Thr Cys Pro Pro Cys Pro Ala Pro Glu Leu
1               5                   10

<210> SEQ ID NO 9
<211> LENGTH: 4
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 9

Gly Gly Tyr Arg
1

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ser Phe Asn Arg Gly Glu Cys
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ser Cys Asp Lys Thr His Thr
1               5

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Thr Cys Pro Pro Cys Pro Ala Pro Glu Leu
1               5                   10

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Cys Pro Pro Cys
1

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Glu Glu Gln Tyr Asn Ser Thr Tyr Arg
1               5
```

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Glu Glu Gln Tyr Gln Ser Thr Tyr Arg
1               5

<210> SEQ ID NO 16
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Ser Cys Asp Lys Thr His Thr Cys Pro Pro Cys Pro Ala Pro Glu Leu
1               5                   10                  15

Leu Gly Gly Pro Ser Val Phe Leu Phe Pro Pro Lys Pro Lys
            20                  25                  30

<210> SEQ ID NO 17
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Val Thr His Gln Gly Leu Ser Ser Pro Val Thr Lys Ser Phe Asn Arg
1               5                   10                  15

Gly Glu Cys

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Asn Asn Tyr Lys Thr Thr Pro Pro Val Leu
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asp Ser Val Lys Gly Arg Phe Thr Ile Ser Arg
1               5                   10

<210> SEQ ID NO 20
<211> LENGTH: 53
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 20

Asp Arg Val Thr Ile Thr Cys Arg Ala Ser Gln Ser Ile Ser Ser Tyr
1               5                   10                  15

Leu Asn Trp Tyr Gln Gln Lys Pro Gly Lys Ala Pro Lys Leu Leu Ile
            20                  25                  30

Tyr Ala Ala Ser Ser Leu Gln Ser Gly Val Pro Ser Arg Phe Ser Gly
        35                  40                  45

Ser Gly Ser Gly Thr
    50

<210> SEQ ID NO 21
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Asp Ser Val Lys Gly Arg Phe Thr Ile Ser Arg His Asn Ser Lys Asn
1               5                   10                  15

Thr Leu Tyr Leu Gln Met
            20

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ser Thr Ala Ala Leu Gly Cys Leu Val Lys
1               5                   10
```

SITE-SPECIFIC QUANTITATION OF DRUG CONJUGATIONS

SEQUENCE LISTING

The instant application contains a Sequence Listing which has been submitted electronically in ASCII format and is hereby incorporated by reference in its entirety. Said ASCII copy, created on Jan. 21, 2021, is named 070816-01402_SL.txt and is 6,122 bytes in size.

FIELD

The present application generally pertains to methods for site-specific quantitation or characterization of drug conjugations of antibody-drug conjugates using protease-assisted drug deconjugation and mass spectrometry.

BACKGROUND

An antibody-drug conjugate (ADC) includes an antibody having attachments of biologically active drugs, e.g., drug payloads, through linkers. The development of ADCs is a strategy to improve drug efficacy, since antibodies can bind to specific sites of target cells allowing for efficient delivery of the biologically active drugs to target cells. Significant improvements have been achieved using ADCs to deliver chemotherapeutic drugs to target cancer cells.

Due to the polyvalent nature of antibodies and the non-specific electrophilic reactions between the amino acids and the linker molecules, the preparation of ADCs can be challenging. The general distribution profile of ADCs contains a mixture of ADCs, unconjugated antibodies, and unconjugated drug payloads. The amount of drugs which can be delivered to the target cells would decrease in the presence of unconjugated antibodies, since the unconjugated antibodies compete with drug-conjugated antibodies for the target antigens. Commonly, the derived ADCs are highly heterogeneous species containing various ADC species with variable drug-to-antibody ratios (DARs) and varied conjugation sites including conjugated conjugation sites and unconjugated conjugation sites. The heterogeneity of ADCs can have significant impacts on drug safety and efficacy due to the presence of undesired ADC species. Desirable ADC formulations should include well-defined DARs and a degree of homogeneity. Quantitation and characterization of site-specific drug conjugations of ADCs with variable DARs, such as site-specific quantitation of drug conjugation, are critical processes to control the quality attributes of ADC formulations, which can directly affect the efficacy of ADC.

Mass spectroscopy (MS), liquid chromatography coupled mass spectroscopy (LC-MS) and imaged capillary isoelectric focusing (iCIEF) have been used to characterize ADC mixtures (Wagh et al., mAbs, 10:2, 222-243, 2018, Challenges and new frontiers in analytical characterization of antibody-drug conjugates). However, due to the complexity of ADC heterogeneity, substantial challenges exist in site-specific quantitation of drug conjugations for characterization of ADCs.

It will be appreciated that a need exists for methods to characterize ADCs to ensure well-defined DARs and a degree of homogeneity relevant to drug safety and efficacy, particularly for site-specific quantitation and/or characterization of drug conjugations of ADCs.

SUMMARY

The present application provides a method for site-specific quantitation and/or characterization of drug conjugations of antibody-drug conjugates, wherein conjugation includes an attachment linked to a specific conjugation site of a partially conjugated peptide or protein in a sample. There may be issues regarding the linkage chemistries used for drug-antibody conjugation due to wide variance in DAR and poor control of attachment location on the antibody. The resultant ADC can be a highly heterogeneous mixture containing various ADC species. Challenges remain to quantify site-specific drug conjugation at different sites and desirable ADC formulations should include well-defined DARs and a degree of homogeneity.

This disclosure provides a method for quantifying or characterizing conjugation of at least one attachment linked to at least one specific conjugation site of a partially conjugated peptide or protein in a sample, comprising: cleaving a portion of the attachment to generate the peptide or protein containing a cleaved linker, wherein the attachment comprises the cleaved linker; adding a modified linker to an unconjugated conjugation site of the partially conjugated peptide or protein; and subjecting the sample to mass analysis to identify the peptide or protein containing the cleaved linker and/or the modified linker. In some aspects, the portion of the attachment is cleaved using papain, cathepsin B or plasmin.

In some aspects, in the method of the present application, the at least one attachment comprises a linker and a payload, wherein the cleaved portion of the attachment comprises the payload and wherein the linker comprises the cleaved linker. In some aspects, the method of the present application further comprises quantifying or characterizing the site-specific conjugation of the attachment based on quantifying the cleaved linker and the modified linker. In some aspects, in the method of the present application, the mass analysis is conducted using a mass spectrometer, electrospray ionization mass spectrometer, nano-electrospray ionization mass spectrometer, or a triple quadrupole mass spectrometer, wherein the mass spectrometer can be coupled to a liquid chromatography system, wherein the mass spectrometer is capable of performing a LC-MS (liquid chromatography-mass spectrometry), a LC-MRM-MS (liquid chromatography-multiple reaction monitoring-mass spectrometry) or a LC-MS/MS analyses.

In some aspects, the method of the present application further comprises treating the peptide or protein with an enzyme prior to cleaving the portion of the attachment and/or prior to adding the modified linker to the unconjugated conjugation site. In some aspects, the method of the present application further comprises treating the sample with an enzyme prior to subjecting the sample to the mass analysis. In some aspects, the portion of the attachment is cleaved using an enzyme, a protease, a chemical, an acid, a base, or a reducing agent. In some aspects, the step of adding the modified linker to the unconjugated conjugation site is performed prior to conducting the step of cleaving the portion of the attachment. In some aspects, the step of cleaving a portion of the attachment is performed prior to conducting the step of adding a modified linker and the step of subjecting the sample to mass analysis. In some aspects, a molecular weight of the modified linker is different from a molecular weight of the cleaved linker.

In other aspects, the method of the present application further comprises treating the peptide or protein with an enzyme prior to cleaving the portion of the attachment and/or prior to adding the modified linker to the unconjugated conjugation site, wherein the enzyme is trypsin. In some aspects, the method of the present application further comprises treating the sample with an enzyme prior to subjecting the sample to the mass analysis, wherein the enzyme is Glu-C. In some aspects, the specific conjugation site or the unconjugated conjugation site is located within a cysteine reside of the peptide or the protein. In some aspects, the attachment is linked to the at least one specific conjugation site through a maleimide attachment group. In some aspects, the peptide or protein is an antibody, an antibody fragment, a Fab region of an antibody, a Fc region of an antibody or a fusion protein.

In some aspects, the linker is an acid-labile linker, a protease-cleavable linker, a disulfide-containing linker, a pyrophosphate-diester linker, or a hydrazone linker. In some aspects, the linker comprises a peptide including valine-alanine, phenylalanine-lysine, valine-citrulline, or derivatives thereof. In some aspects, the linker further comprises polyethylene glycol, para-aminobenzyloxycarbonyl (PABC) or para-aminobenzylalcohol (PABA).

In other aspects, the modified linker comprises polyethylene glycol. In some aspects, the modified linker is added to the unconjugated conjugation site through a maleimide attachment group.

In yet other aspects, the payload is a drug, a compound, a toxin, a cytotoxic agent, an anti-mitotic agent, a microtubule inhibitor, a DNA-damaging agent, a topoisomerase inhibitor, a RNA polymerase inhibitor, an amanitins analog, a tubu-lysin analog, a chemotherapeutic drug, a microtubule polymerization inhibitor or a microtubule polymerization promoter.

In some aspects, the partially conjugated peptide or protein is selected from the group consisting of a conjugated peptide or protein of formula I,

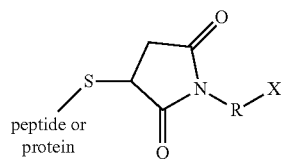

wherein R is a linker, wherein X is a payload. In some aspects, the linker comprises polyethylene glycol and the payload is a drug, a compound, a toxin, a cytotoxic agent, an anti-mitotic agent, a microtubule inhibitor, a DNA-damaging agent, a topoisomerase inhibitor, a RNA polymerase inhibitor, an amanitins analog, a tubu-lysin analog, a chemotherapeutic drug, a microtubule polymerization inhibitor, or a microtubule polymerization promoter.

In some aspects, the partially conjugated peptide or protein is selected from the group consisting of a conjugated peptide or protein of formula II,

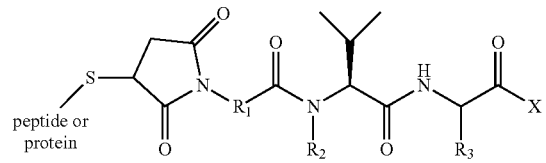

wherein $R_1$ is a spacer, wherein $R_2$ is —H or —$CH_3$, wherein $R_3$ is —$CH_3$, or —$(CH_2)_3NHC(O)NH_2$, wherein X is a payload. In some aspects, the spacer comprises polyethylene glycol and the payload is a drug, a compound, a toxin, a cytotoxic agent, an anti-mitotic agent, a microtubule inhibitor, a DNA-damaging agent, a topoisomerase inhibitor, a RNA polymerase inhibitor, an amanitins analog, a tubu-lysin analog, a chemotherapeutic drug, a microtubule polymerization inhibitor, or a microtubule polymerization promoter.

In other aspects, the partially conjugated peptide or protein is selected from the group consisting of a conjugated peptide or protein of formula III,

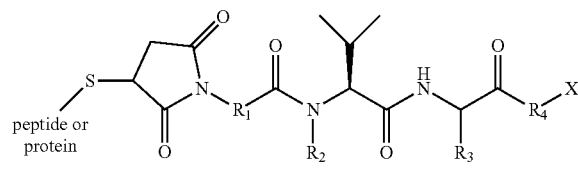

wherein $R_1$ is a first spacer, wherein $R_2$ is —H or —$CH_3$, wherein $R_3$ is —$CH_3$, or —$(CH_2)_3NHC(O)NH_2$, wherein $R_4$ is a second spacer, wherein X is a payload. In some aspects, the first spacer comprises polyethylene glycol, the second space comprises para-aminobenzyloxycarbonyl (PABC) or para-aminobenzylalcohol (PABA), and the payload is a drug, a compound, a toxin, a cytotoxic agent, an anti-mitotic agent, a microtubule inhibitor, a DNA-damaging agent, a topoisomerase inhibitor, a RNA polymerase inhibitor, an amanitins analog, a tubu-lysin analog, a chemotherapeutic drug, a microtubule polymerization inhibitor or a microtubule polymerization promoter.

This disclosure, at least in part, provides a method for quantifying or characterizing conjugation of at least one attachment linked to at least one specific conjugation site of a partially conjugated protein in a sample. In some embodiments, the method of the present application comprises cleaving a portion of the attachment using a first enzyme to generate a protein containing a cleaved linker, wherein the at least one attachment comprises the cleaved linker; followed by subjecting the sample to a second enzyme to obtain a peptide mixture; and subjecting the peptide mixture to mass analysis to quantify or characterize the at least one specific conjugation site of the attachment based on quantifying the peptide containing the cleaved linker and/or the peptide which does not contain the cleaved linker. In one aspect, the at least one specific conjugation site is located within a lysine residue of the protein.

In one aspect, the at least one attachment comprises a linker and a payload, wherein the cleaved portion of the at least one attachment comprises the payload and wherein the linker comprises the cleaved linker. In one aspect, the mass analysis is conducted using a mass spectrometer, electrospray ionization mass spectrometer, nano-electrospray ionization mass spectrometer or a triple quadrupole mass spectrometer, wherein the mass spectrometer can be coupled to a liquid chromatography system and wherein the mass spectrometer is capable of performing a LC-MS (liquid chromatography-mass spectrometry), a LC-MRM-MS (liquid chromatography-multiple reaction monitoring-mass spectrometry) or a LC-MS/MS analyses. In one aspect, the method of the present application further comprises treating the peptide mixture with a third enzyme prior to subjecting the peptide mixture to the mass analysis. In one aspect, the first enzyme is papain, cathepsin B, or plasmin; and/or wherein the second enzyme is Glu-C or trypsin. In one aspect, the third enzyme is Asp-N or Glu-C.

In one aspect, the protein is an antibody, an antibody fragment, a Fab region of an antibody, a Fc region of an antibody, or a fusion protein. In one aspect, the linker comprises valine-alanine, phenylalanine-lysine, valine-citrulline, or derivatives thereof. In one aspect, the payload is a drug, a compound, a toxin, a cytotoxic agent, an antimitotic agent, a microtubule inhibitor, a DNA-damaging agent, a topoisomerase inhibitor, a RNA polymerase inhibitor, an amanitins analog, a tubu-lysin analog, a chemotherapeutic drug, a microtubule polymerization inhibitor, or a microtubule polymerization promoter.

These, and other, aspects of the invention will be better appreciated and understood when considered in conjunction with the following description and the accompanying drawings. The following description, while indicating various embodiments and numerous specific details thereof, is given by way of illustration and not of limitation. Many substitutions, modifications, additions, or rearrangements may be made within the scope of the invention.

BRIEF DESCRIPTION OF THE DRAWINGS

FIG. 6A shows an exemplary method of the present application comprising digesting ADCs with trypsin, digesting the tryptic peptide mixture with papain to remove payload; conjugating modified linkers to unconjugated sulfhydryl groups (e.g., labelling); digesting the peptide mixture with Glu-C; and subjecting the peptide mixture to LC-MS analysis according to an exemplary embodiment.

FIG. 13A shows the analysis results of tryptic hinge region peptide (TH-TCPPCPAPELLGGPSVFLFPPKPK (SEQ ID NO.: 1)) according to an exemplary embodiment.

FIG. 13B shows the analysis results of a peptide with amino acid sequence of CPPCPAPE (SEQ ID NO.: 2) (tryptic hinge region peptide digested with papain) according to an exemplary embodiment.

FIG. 13C shows the analysis results of a peptide with amino acid sequence of CPPCPAPELL (SEQ ID NO.: 3) (tryptic hinge region peptide digested with papain) according to an exemplary embodiment. These peptides may contain LK1 (designated as +1495.7, including payload) or cleaved LK1 (designated as +762.4).

FIG. 17 shows intra-day precision of the method of the present application regarding the analysis results of DAR of GEC peptide, SCDK (SEQ ID NO: 7) peptide, and hinge region peptides according to an exemplary embodiment.

FIG. 18A shows the results of conducting papain digestion followed by LK2 attachment as the method shown in FIG. 6A according to an exemplary embodiment.

FIG. 18B shows the results of conducting LK2 attachment followed by papain digestion as the method shown in FIG. 6B according to an exemplary embodiment. The MAB1-LK1 ADC samples with high DAR were analyzed. Cleaved LK1 is designated as +762.4. LK2 is designated as +592.3. (+592.3, +592.3) indicates zero conjugation. (+762.4, +592.3) indicates one drug conjugation. (+762.4, +762.4) indicates two drug conjugations according to an exemplary embodiment.

FIG. 25 shows intra-day and inter-day precision of the method of the present application regarding the analysis results of DAR of GEC, SCDK (SEQ ID NO: 7), and hinge region peptides according to an exemplary embodiment. Figure also discloses SEQ ID NO: 2.

DETAILED DESCRIPTION

Figure 1:
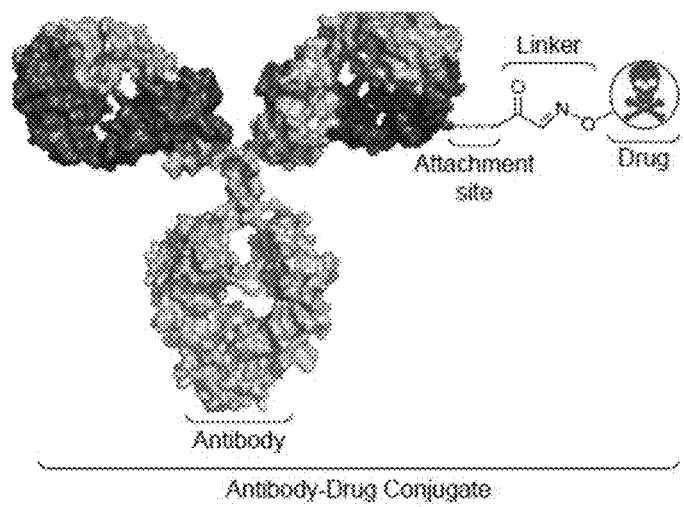
FIG. 1 shows an antibody-drug conjugate (ADC), wherein the drug is conjugated to an antibody through a linker. The antibody component of ADC binds to tumor antigen of target cell and subsequently the ADC-antigen complex undergoes receptor-mediated endocytosis. The drug components of ADCs can be released due to lysosomal degradation of ADC or cleavage of the linkers.
Figure 1:
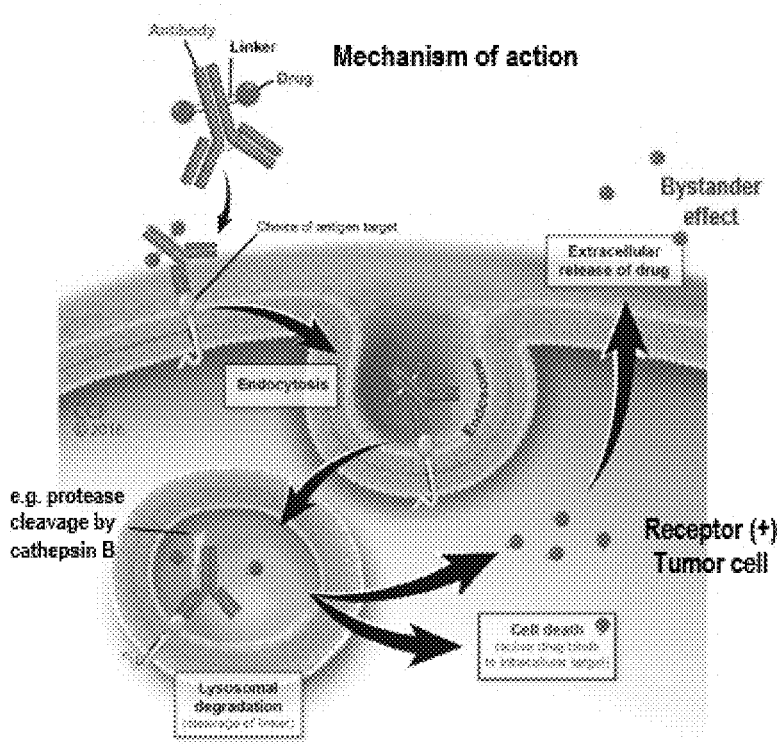

Antibody-drug conjugates (ADC) are therapeutics which utilize the specificity of antibodies to selectively deliver drugs, such as highly potent cytotoxic drugs or chemotherapeutic drugs, to target cells. ADCs can provide targeted delivery of cytotoxic agents for cancer treatment. Antibodies targeting specific tumor surface antigens can be conjugated to drugs through linkers to generate ADCs as effective therapeutics for cancer treatments. As shown in FIG. 1, the antibody component of ADCs binds to tumor antigen and subsequently the ADC-antigen complex undergoes receptor-mediated endocytosis. Since lysosomes contain proteases, such as cathepsin B and plasmin, the drug components of ADCs can be released due to lysosomal degradation of ADC or cleavage of the linkers. (Changshou Gao. 7th World ADC. 2016, San Diego, Instability of thiol/maleimide conjugation and strategies for mitigation; Jagadeesh et al., Antibody drug conjugates (ADCs): Changing the treatment landscape of lymphoma, Current Treatment Options in Oncology, 17, 55, 2016, https://doi.org/10.1007/s11864-016-0428-y). Preferable target antigens should display differential expression between tumor and normal tissues with increased expression in cancer cells. ADCs can increase efficacy and decrease toxicity by selectively delivering drugs to cancer cells, thus lowering the minimum effective dose in comparing to traditional chemotherapeutic cancer treatments. Since less drugs reach non-target tissue, e.g., normal tissue, due to targeted drug delivery by the antibody, the maximum tolerated drug dose is increased. (Panowski et al., Site-specific antibody drug conjugates for cancer therapy, mAbs, 6:1, 34-45, DOI: 10.4161/mabs.27022). The use of ADCs can improve the therapeutic window due to improved efficacy, reduced systemic toxicity, preferable pharmacokinetics, preferable pharmacodynamics, and preferable bio-distribution in comparing to traditional chemotherapy. (Tsuchikama et al., Protein Cell, 2018, 9(1), pages 33-46, Antibody-drug conjugates: recent advances in conjugation and linker chemistries)

Figure 2:
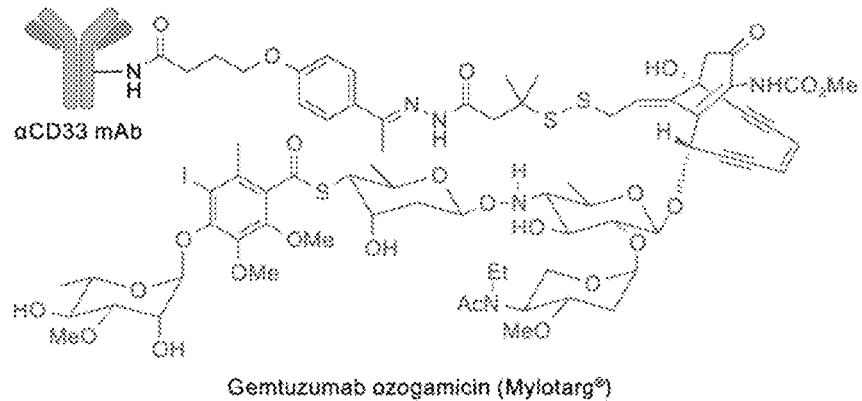
FIG. 2 shows the chemical structures of Mylotarg®, Adcetris®, and Kadcyla®.
Figure 2:
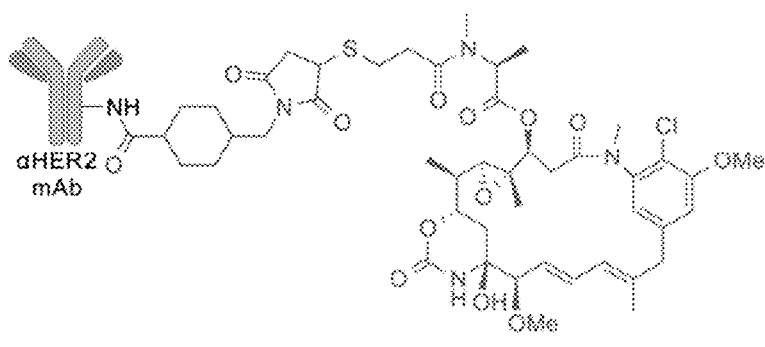
Figure 2:
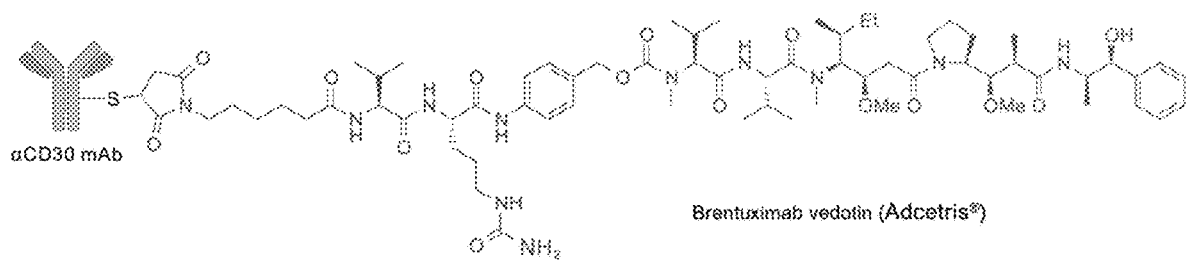

FDA-approved ADCs include gemtuzumab ozogamicin (Mylotarg®) in 2000 for CD33-positive acute myelogenous leukemia, brentuximab vedotin (Adcetris®) in 2011 for CD30-positive relapsed or refractory Hodgkin's lymphoma and systemic anaplastic large cell lymphoma, trastuzumab emtansine (Kadcyla®) in 2013 for HER2-positive breast cancer, inotuzumab ozogamicin (Besponsa®) targeting CD22 in 2017 for acute lymphoblastic leukemia, polatuzumab vedotin (Polivy®) targeting CD79b in 2019 for diffuse large B-cell lymphoma, Enfortumab vedotin (Padcev®) targeting Nectin-4 in 2019 for bladder cancer, and trastuzumab deruxtecan (Enhertu®) targeting HER2 in 2019 for breast cancer. However, Mylotarg® was withdrawn from the market in 2010 due to a lack of clinical benefit and high fatal toxicity rate compared to the standard chemotherapy. The chemical structures of Mylotarg®, Adcetris®, and Kadcyla® are shown in FIG. 2. (Tsuchikama et al.) A majority of the active ADC clinical trials are in Phase I for a diversity of target antigens. The examples of ADC target antigens include HER2, EGFR, CD19, CD33, CD70, cMet, BCMA, CD123, CD22, CD37, CD71, CD74, GC-C, FGFR, mesothelin, ENPP3, AXL receptor tyrosine kinase, CDH6, CEACAM4, DLL3, FLT3, folate receptor 1, PSMA, GPNMB, HER3, IGF-1R, SLC44A4, TAA, and so on. The development of ADC is challenging, since it was estimated that about 25% of the ADC developments were discontinued during clinical trials.

ADCs are constructed from an antibody targeting a specific antigen, a drug payload, and a linker which connects the drug payload and the antibody. The commonly used antibody isotypes for developing ADCs include IgG1, IgG2, and IgG4. There are various types of linkers available for conjugations including protease cleavable linkers, non-cleavable linkers, hydrazone linkers and disulfide bond linkers. The available conjugation sites in the antibody include lysine and cysteine residues. In addition, non-natural amino acids or engineered cysteine residues can be added to antibodies at specific sites. The available primary conjugate sites of an antibody include the amino groups of the lysine residues. There are about 80 lysine residues on a typical antibody and about 10 lysine residues are chemically accessible. The chemical conjugation of linkers to antibodies include lysine amide coupling using activated carboxylic acid esters.

Cysteine-based conjugation can also be used to construct ADCs. There are no free thiols in antibodies in general, since all cysteine residues form disulfide bonds. There are 4 inter-chain and 12 intra-chain disulfide bonds in antibodies, such as IgG1. The inter-chain disulfide bonds are generally not critical for the structure stability of IgG1. The sulfhydryl groups (—SH) of the cysteine residues of the antibody are available as primary conjugation sites, when the inter-chain disulfide bonds of the antibody are selectively reduced. Thus, cysteine conjugation may be limited to the eight exposed sulfhydryl groups after reduction of the inter-chain disulfide bonds. Linker-drugs per antibody for cysteine conjugation can range from 1-8, generating more than one hundred different ADC species. The diversity in heterogeneity of an ADC mixture is relatively high, because these ADC species differ in drug load and conjugation site. (Panowski et al.) Additional cysteine residues can be introduced to the antibodies through genetic engineering or other technologies.

Figure 3:
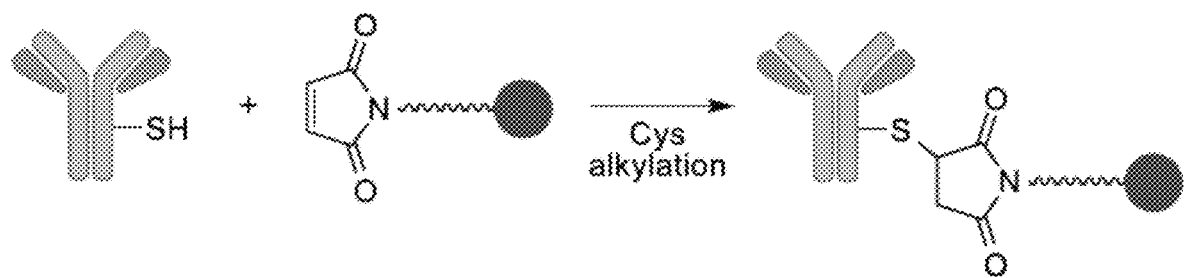
FIG. 3 shows cysteine coupling by conjugating a linker to an antibody through maleimide alkylation.

Commonly, ADCs have high degrees of structural heterogeneity including various DARs, conjugation sites and occupancy degrees. Payload occupancies can vary at different conjugation sites depending on the solvent-accessibility, local charge and steric effect. Locations and occupancies of specific conjugation sites can modulate ADC stability and efficacy. The lysine or cysteine conjugated ADCs are heterogenous including size variants and charge variants. The mass considerations of quality attributes of ADCs, such as the lysine or cysteine conjugated ADCs, include DAR, drug load distribution, presence of unconjugated antibodies and presence of residual drugs. The selection of conjugation sites can modulate the stability and efficacy of ADCs. Cysteine-based conjugation methods rely on a specific reaction between cysteine residues of the antibody and thiol-reactive functional groups. Maleimide can be used to conjugate the linker to the reduced antibody cysteine thiol through maleimide alkylation. FIG. 3 shows a maleimide moiety reacts with a reduced cysteine residue of an antibody (Tsuchikama et al.)

Figure 4:
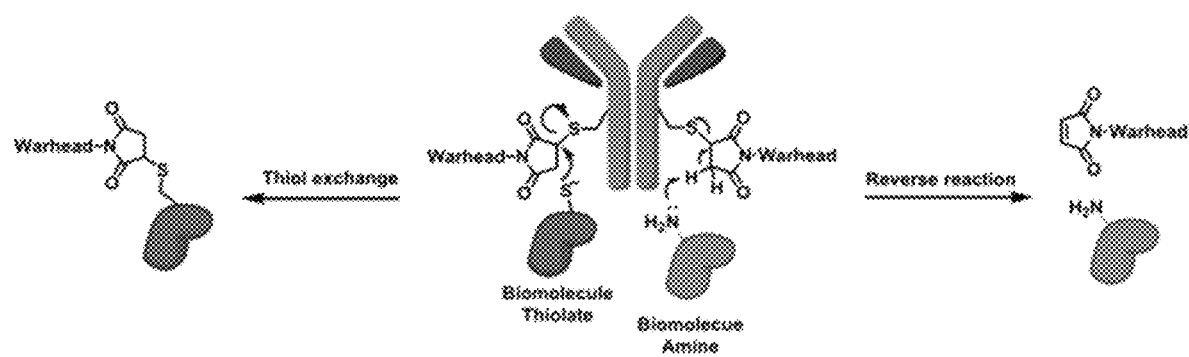
FIG. 4 shows de-conjugation associated with thiol-maleimide conjugation for cysteine conjugated ADCs by going through thiol exchange or reverse reaction.

There are issues regarding the linkage chemistries used for drug-antibody conjugation. If the resultant ADCs are unstable constructs, they may lead to premature drug release. Other problems are relevant to a wide variance in DAR and poor control of attachment location on the antibody. The variations and instabilities of ADCs contribute to variable pharmacokinetic profiles. The resultant ADC can be a highly heterogeneous mixture containing various ADC species. De-conjugation may occur to cysteine conjugated ADCs, such as going through thiol exchange or reverse reaction, as shown in FIG. 4 for the instability associated with thiol-maleimide conjugation for cysteine-based conjugation. When the conjugation of ADC is based on lysine residues in CH2 domain of the antibody, the CH2 domain may undergo destabilization triggering post-translation modification (PTM) degradation which has negative impact on the half-life of the antibody. The lysine-based conjugation may compromise the binding affinity of ADCs, such as directly altering the binding epitopes or indirectly causing structural changes. For example, the methionine 258 residue in ADC is more accessible to oxidation in comparison with unconjugated antibodies. (Luo et al., Structural Characterization of a Monoclonal Antibody-Maytansinoid Immunoconjugate, Anal Chem 2016 Jan. 5; 88(1):695-702. doi: 10.1021/acs.analchem.5b03709. Epub 2015 Dec. 14; Buecheler, J. W., et al. Journal of Pharmaceutical Sciences 109 (2020) 161-168162). The de-conjugation of payload can lead to reduced on-target efficacy, increased off-target toxicity, or uncontrolled distribution of drug. The DAR of ADCs may change over time in serum. The challenges remain in site-specific quantitation of drug conjugation and quantitation of the loss of drug conjugation at different sites. The analytical characterization of ADC includes molecular integrity, heterogeneity, degradation, stability and changes of DAR. The desirable ADC formulations should include well-defined DARs and degree of homogeneity by reducing the undesired ADC species to improve the safety and efficacy of the ADC formulations.

DAR represents an average number of drugs conjugated to an antibody, which can be directly linked to efficacy and safety of ADC. The characterization of DAR can be critical for controlling the critical quality attribute of ADC, since a well-defined DAR provides critical information regarding total drug load, drug load distribution, levels of unconjugated antibodies, levels of residual unconjugated drugs, and sites of conjugations. Low DAR represents low drug loading which contributes to reduced potency of ADCs. High DAR represents high drug loading which can alter pharmacokinetics and toxicity of ADCs. The major quality attributes of ADC include characterizations of DAR, drug load distribution, the levels of unconjugated antibody, the levels of residual unconjugated drug, size variants of ADC, and charge variants of ADC.

The characterization and quantitation of ADCs using mass spectrometry approaches can be challenging with run-to-run variations, since the conjugation of linker and payload significantly affects peptide ionization. Although mass spectrometry-based peptide mapping is powerful in characterizing therapeutic proteins, this general strategy usually cannot quantify site-specific conjugations for ADCs due to ionization discrepancy from significant molecular weight difference between wild-type peptides and conjugated peptides. In addition, tryptic digestion of ADCs yields short peptide containing conjugation sites, such as the inter-chain disulfide bond between heavy chain and light chain, which are difficult to be retained on Reversed Phase Liquid Chromatography (RPLC). Furthermore, the transformation of drug conjugated peptides during sample preparation, such as under high temperature and/or acidic condition, can cause the risks of analyte stability and reproducibility. When Capillary Electrophoresis-Mass Spectrometry (CE-MS) are used for characterizing ADCs, it allows retention of short peptides. However, there are issues regarding quantitative reproducibility.

The selection of linkers is important for the efficacy of ADCs, since an ideal linker should be stable in circulating blood, allowing rapid release of active free drugs inside tumor cells. The applicable linker formats can be non-cleavable or cleavable linkers. Cleavable linkers are designed to be cleaved by responding to an environmental difference between the extracellular and intracellular environments, such as pH or redox potential, or by specific lysosomal enzymes.

Examples of cleavable linkers are acid-labile linkers, protease-cleavable linkers, disulfide-containing linkers, or pyrophosphate-diester linkers. Hydrazone linker is an example of an acid-labile linker. Acid-labile linkers are designed to be stable at the pH levels of the blood, but the acid-labile linkers may become unstable and degradable in the low pH environment in lysosomes. The disulfide linker contains a disulfide linkage which can release free drugs inside the cell, when the level of intracellular reduced glutathione is high.

Protease-cleavable linkers are designed to be stable in blood, but the active free drugs can be released rapidly inside lysosomes in cells upon cleaving by lysosomal enzymes. The protease activity inside lysosomes is relatively high. Some specific peptide sequences can be recognized and cleaved by the lysosomal proteases, such as a dipeptide linkage that can be hydrolyzed by cathepsin B. Cathepsin B can recognize certain dipeptide sequences, such as valine-alanine, phenylalanine-lysine and valine-citrulline, and cleaves a peptide bond on the C-terminal side of such sequences. A spacer, such as para-aminobenzyloxycarbonyl (PABC) or para-aminobenzylalcohol (PABA), can be coupled to these dipeptides to construct cleavable dipeptide linkers. The presence of a spacer between the dipeptide moiety and the payload allows cathepsin B to exhibit its protease activity, when bulky payload molecules are used. (Tsuchikama et al.)

The selection of drug payloads can be critical to the therapeutic effects of ADC. It is preferable that the payload in ADC is a cytotoxic chemical agent that has high potency to cancer cells and low off-target cytotoxicity to normal cells. In some aspects, the payload is a cytotoxic agent or an anti-mitotic agent. In some aspects, the payload is a microtubule inhibitors, such as maytansines or auristatins. In some exemplary examples, the payload is a DNA-damaging agent, such as anthracyclines, calicheamicins, duocarmycins, pyrrolobenzodiazepines, or pyrrolobenzodiazepine dimers (PBDs). DNA-damaging agent functions by binding the minor groove of DNA to cause DNA strand scission, alkylation, or cross-linking. In some aspects, the payload is a topoisomerase inhibitor or a RNA polymerase inhibitor. In some aspects, the payload is amanitins or tubu-lysin analogs. In some aspects, the payload is a chemotherapeutic drug including the folate and purine analogs (methotrexate, 6-mercaptopurine), microtubule polymerization inhibitors/promoters (vinca alkaloids, taxanes) and DNA damaging agents (anthracyclines, nitrogen mustard).

In some aspects, an ADC comprises an antibody, a payload, and a linker, wherein the linker is loaded with the payload and attached to the antibody, wherein the linker comprises a cleavage site. In some aspects, the cleavage site can be cleaved by responding to an environmental difference between the extracellular and intracellular environments, such as pH or redox potential, or by specific lysosomal enzymes. In some aspects, the cleavage site is an acid-labile cleavage site, a protease cleavage site, a disulfide containing cleavage site, or a pyrophosphate-diester containing cleavage site.

In some aspects, an ADC comprises an antibody, a payload, and a linker, wherein the linker is loaded with the payload and attached to the antibody, wherein the linker comprises a spacer and a cleavage site, wherein the spacer is a PEG (polyethylene glycol) or PEG8.

In other aspects, an ADC comprises an antibody, a payload, and a linker, wherein the linker is loaded with the payload and attached to the antibody, wherein the linker comprises a first spacer, a cleavage site, and a second spacer, wherein the first space is a PEG or PEG8, and the second spacer is PABC or PABA.

Figure 5A:
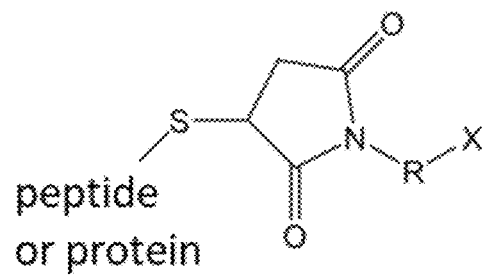
FIG. 5A shows the chemical structures of ADCs according to some aspects. Each ADC comprises an antibody and a payload connecting by linker, wherein the linker is attached to a sulfhydryl group of a cysteine residue of a peptide or protein using a maleimide attachment group according to some aspects.
Figure 5A:
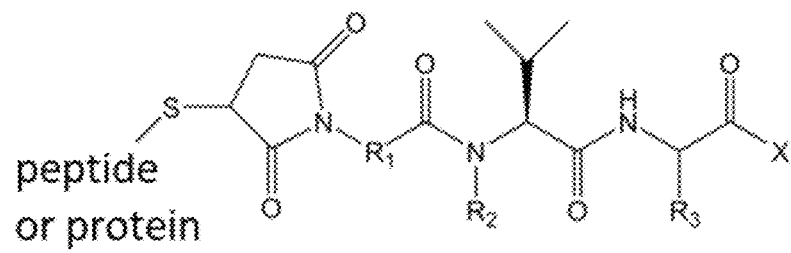
Figure 5A:
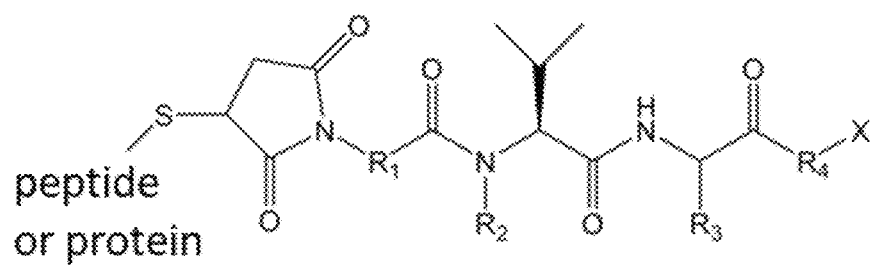

In yet other aspects, an ADC comprises an antibody, a payload, and a linker, wherein the linker is attached to a sulfhydryl group of a cysteine residue of an antibody using a maleimide attachment group as shown in formula I in FIG. 5A, wherein R is a linker, wherein X is a payload. In some embodiments, the linker comprises a PEG, and the payload is a drug, a compound, a toxin, a cytotoxic agent, an anti-mitotic agent, a microtubule inhibitor, a DNA-damaging agent, a topoisomerase inhibitor, a RNA polymerase inhibitor, an amanitins analog, a tubu-lysin analog, a chemotherapeutic drug, a microtubule polymerization inhibitor, or a microtubule polymerization promoter. In some aspects, the linker further comprises a cleavage site. In some aspects, the cleavage site is a dipeptide which can be recognized by a protease. In some aspects, the dipeptide is valine-alanine, phenylalanine-lysine, valine-citrulline, or derivatives thereof.

In some aspects, an ADC comprises an antibody, a payload, and a linker, wherein the linker is attached to a sulfhydryl group of a cysteine residue of an antibody using a maleimide attachment group as shown in formula II in FIG. 5A, wherein $R_1$ is a spacer (such as PEG or PEG8), wherein $R_2$ is —H or —$CH_3$, wherein $R_3$ represents a general structure of the side chain of alanine or citrulline, such as —$CH_3$, or —$(CH_2)_3NHC(O)NH_2$, wherein X is a payload. In some embodiments, the payload is a drug, a compound, a toxin, a cytotoxic agent, an anti-mitotic agent, a microtubule inhibitor, a DNA-damaging agent, a topoisomerase inhibitor, a RNA polymerase inhibitor, an amanitins analog, a tubu-lysin analog, a chemotherapeutic drug, a microtubule polymerization inhibitor, or a microtubule polymerization promoter.

In other aspects, an ADC comprises an antibody, a payload, and a linker, wherein the linker is attached to a sulfhydryl group of a cysteine residue of an antibody using a maleimide attachment group as shown in formula III in FIG. 5A, wherein $R_1$ is a first spacer (such as PEG or PEG8), wherein $R_2$ is —H or —$CH_3$, wherein $R_3$ represents a general structure of the side chain of alanine or citrulline, such as —$CH_3$, or —$(CH_2)_3NHC(O)NH_2$, wherein $R_4$ is a second spacer (such as PABC or PABA). In some embodiments, the payload is a drug, a compound, a toxin, a cytotoxic agent, an anti-mitotic agent, a microtubule inhibitor, a DNA-damaging agent, a topoisomerase inhibitor, a RNA polymerase inhibitor, an amanitins analog, a tubu-lysin analog, a chemotherapeutic drug, a microtubule polymerization inhibitor, or a microtubule polymerization promoter.

Figure 5B:
FIG. 5B shows the chemical structures of ADCs according to some aspects. Each ADC comprises an antibody and a payload connecting by linker, wherein the linker is attached to a lysine residue of a peptide or protein through lysine amide coupling using activated carboxylic acid ester or NHS ester according to some aspects.
Figure 5B:
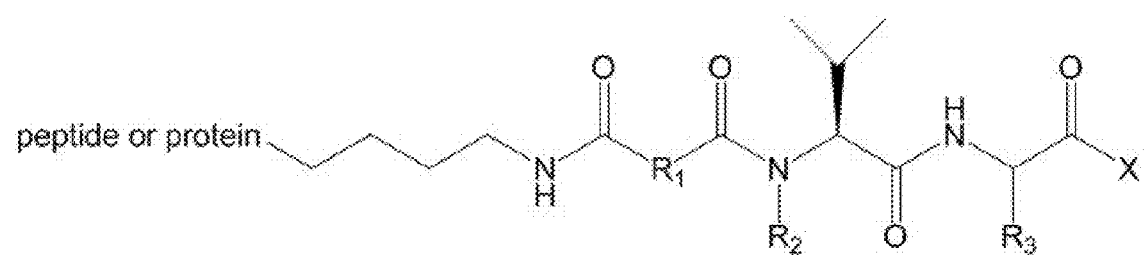
Figure 5B:
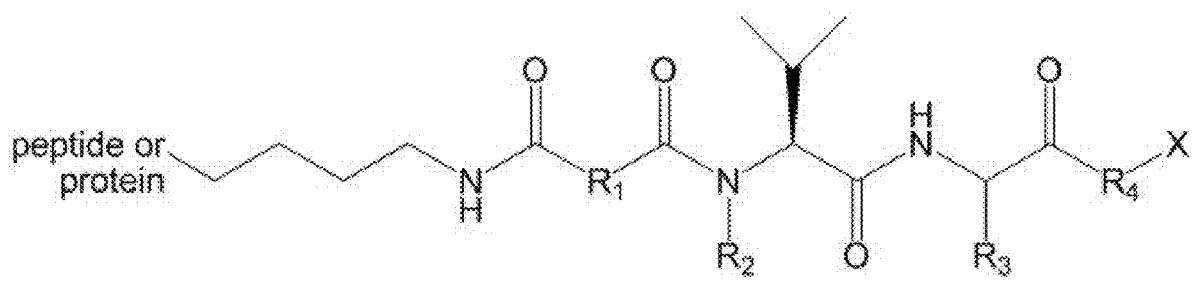

In yet other aspects, an ADC comprises an antibody, a payload, and a linker, wherein the linker is attached to a lysine residue of an antibody through lysine amide coupling using activated carboxylic acid ester or NHS ester as shown in formula IV in FIG. 5B, wherein R is a linker, wherein X is a payload. In some embodiments, the linker comprises a PEG, and the payload is a drug, a compound, a toxin, a cytotoxic agent, an anti-mitotic agent, a microtubule inhibitor, a DNA-damaging agent, a topoisomerase inhibitor, a RNA polymerase inhibitor, an amanitins analog, a tubu-lysin analog, a chemotherapeutic drug, a microtubule polymerization inhibitor, or a microtubule polymerization promoter. In some aspects, the linker further comprises a cleavage site. In some aspects, the cleavage site is a dipeptide which can be recognized by a protease. In some aspects, the dipeptide is valine-alanine, phenylalanine-lysine, valine-citrulline, or derivatives thereof.

In some aspects, an ADC comprises an antibody, a payload, and a linker, wherein the linker is attached to a lysine residue of an antibody through lysine amide coupling using activated carboxylic acid ester or NHS ester as shown in formula V in FIG. 5B, wherein $R_1$ is a spacer (such as PEG or PEG8), wherein $R_2$ is —H or —$CH_3$, wherein $R_3$ represents a general structure of the side chain of alanine or citrulline, such as —$CH_3$, or —$(CH_2)_3NHC(O)NH_2$, wherein X is a payload. In some embodiments, the payload is a drug, a compound, a toxin, a cytotoxic agent, an anti-mitotic agent, a microtubule inhibitor, a DNA-damaging agent, a topoisomerase inhibitor, a RNA polymerase inhibitor, an amanitins analog, a tubu-lysin analog, a chemotherapeutic drug, a microtubule polymerization inhibitor, or a microtubule polymerization promoter.

In some aspects, an ADC comprises an antibody, a payload, and a linker, wherein the linker is attached to a lysine residue of an antibody through lysine amide coupling using activated carboxylic acid ester or NHS ester as shown in formula VI in FIG. 5B, wherein $R_1$ is a first spacer (such as PEG or PEGS), wherein $R_2$ is —H or —$CH_3$, wherein $R_3$ represents a general structure of the side chain of alanine or citrulline, such as —$CH_3$, or —$(CH_2)_3NHC(O)NH_2$, wherein $R_4$ is a second spacer (such as PABC or PABA). In some embodiments, the payload is a drug, a compound, a toxin, a cytotoxic agent, an anti-mitotic agent, a microtubule inhibitor, a DNA-damaging agent, a topoisomerase inhibitor, a RNA polymerase inhibitor, an amanitins analog, a tubu-lysin analog, a chemotherapeutic drug, a microtubule polymerization inhibitor, or a microtubule polymerization promoter.

The present application provides an exemplary method for site-specific quantitation and/or characterization of drug conjugation of ADCs, wherein the ADCs comprises conjugated and unconjugated conjugation sites. The method of the present application comprises the steps of digesting ADCs with a protease to yield a peptide mixture, wherein the peptide may contain conjugated and/or unconjugated conjugation sites. Subsequently, the peptide mixture can be modified or labelled to obtain detectable differentiations between the conjugated and unconjugated conjugation sites. The present application provides a novel protease-assisted drug deconjugation and linker labelling (PADDLL) method to site-specifically quantify conjugations in ADCs. In some aspects, trypsin is used to digest the ADCs. In some aspects, LC-MS is used to detect the differentiations between the peptides containing conjugated and/or unconjugated conjugation sites.

In some aspects, the present application provides a method for quantifying or characterizing conjugation of at least one attachment linked to at least one specific conjugation site of a partially conjugated peptide or protein in a sample, comprising: cleaving a portion of the attachment to generate the peptide or protein containing a cleaved linker, wherein the attachment comprises the cleaved linker; adding a modified linker to an unconjugated conjugation site of the partially conjugated peptide or protein; subjecting the sample to mass analysis to identify the peptide or protein containing the cleaved linker and/or the modified linker; wherein the at least one attachment comprises a linker and a payload, wherein the cleaved portion of the attachment comprises the payload, and wherein the linker comprises the cleaved linker. In some aspects, the method further comprises quantifying or characterizing the site-specific conjugation of the attachment based on quantifying the cleaved linker and the modified linker. In some aspects, the mass analysis is a mass spectroscopy, or a liquid chromatography-mass spectroscopy. The site-specific payload (e.g., drug) conjugation can be calculated based on the quantitation of cleaved linker and modified linker, e.g., site-specific payload (e.g., drug) conjugation=(quantity of cleaved linker)/(quantity of modified linker+quantity of cleaved linker).

In other aspects, the method of the present application can be used to quantify various ADCs which contain cleavable linkers, such as protease cleavable dipeptide linkers, wherein the ADCs can have different antibody isotypes, linker structures and drug payloads, wherein the ADCs can include lysine conjugated and cysteine conjugated ADCs. In some aspects, the method of the present application includes incubating intact ADCs with activated papain at an optimized condition to completely deconjugate drug payload by minimizing non-specific cleavages, followed by conducting reduced peptide mapping procedures including reduction, denaturation and enzymatic digestion. Subsequently, unoccupied conjugation sites are labelled with modified linkers to provide comparable ionization efficiency. Subsequently, the method of the present application includes subjecting the ADC sample to mass analysis, such as LC-MS/MS (liquid chromatography coupled mass spectroscopy/mass spectroscopy), to identify the peptide or protein containing the cleaved linker and/or the modified linker. In some aspects, the modified linker and the cleavable linker of the ADCs have similar structures. In some aspects, the site-specific payload (e.g., drug) conjugation can be calculated based on the quantitation of cleaved linker and modified linker. The percentage of site-specific drug conjugation can be estimated using signal intensities of precursor ions of drug deconjugated peptide and linker labelled peptide, including:

$$\text{Site specific drug conjugation (\%)} = \frac{\text{Drug deconjugated peptide}}{\text{Drug deconjugated peptide} + \text{Linker labelled peptide}}$$

In some preferred aspects, the step of adding the modified linker to the unconjugated conjugation site is performed prior to conducting the step of cleaving the portion of the attachment. In some preferred aspects, the peptide or protein is an antibody, an antibody fragment, a Fab region of an antibody, a Fc region of an antibody, or a fusion protein. In some preferred aspects, a molecular weight of the modified linker is different from a molecular weight of the cleaved linker, wherein these molecular weights are differentiable in a mass analysis.

Figure 6B:
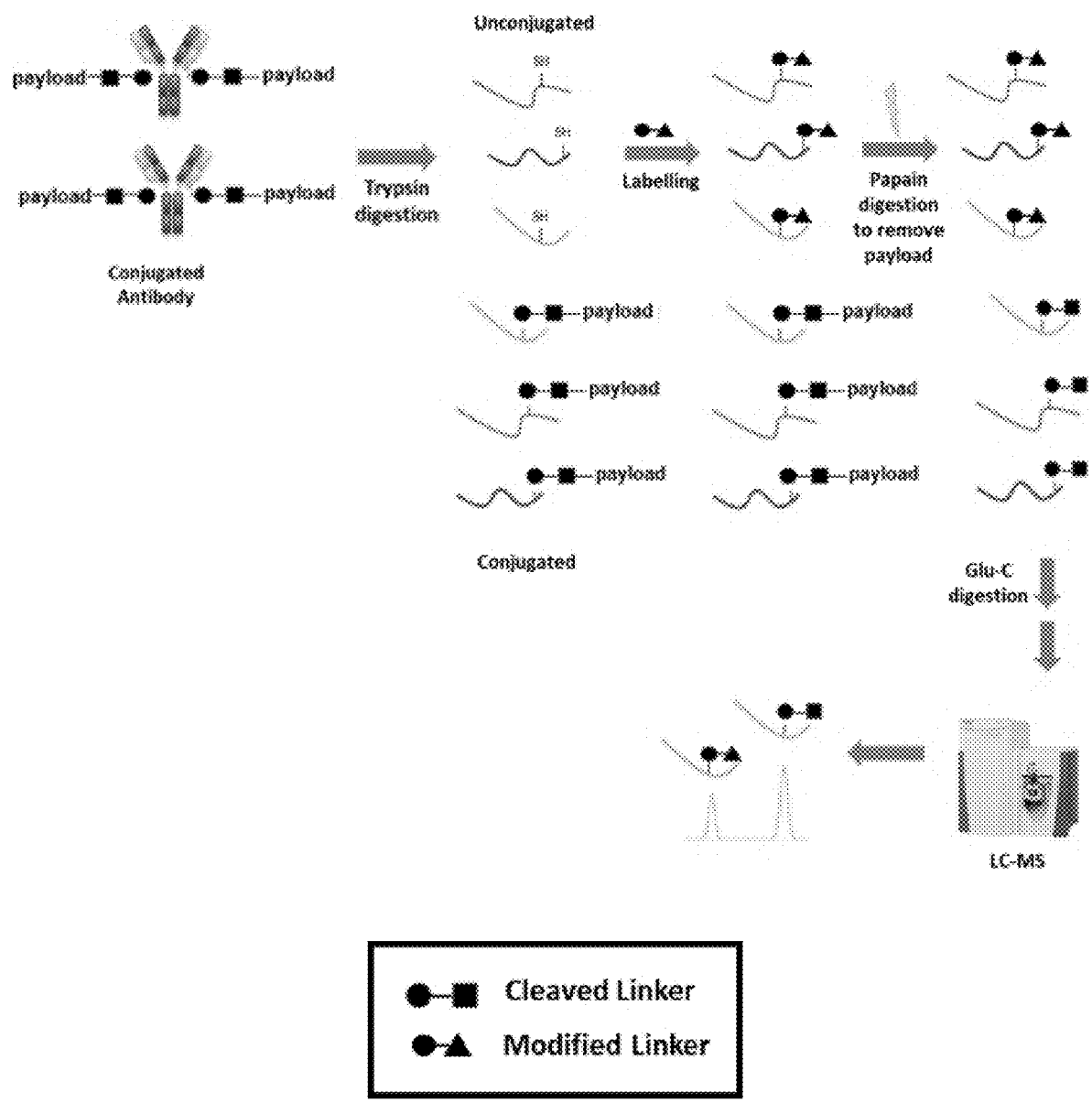
FIG. 6B shows an exemplary method of the present application comprising digesting ADCs with trypsin, conjugating modified linkers to unconjugated sulfhydryl groups (e.g., labelling); digesting the peptide mixture with papain to remove payload; digesting the peptide mixture with Glu-C; and subjecting the peptide mixture to LC-MS analysis according to an exemplary embodiment.

In some aspects, the method of the present application comprises digesting ADCs with trypsin, digesting the tryptic peptide mixture with papain to remove payloads; conjugating modified linkers to unconjugated sulfhydryl groups (e.g., labelling); subsequently digesting the peptide mixture with Glu-C; and subsequently subjecting the peptide mixture to LC-MS analysis as shown in FIG. 6A. In some aspects, the sequence of some steps may be reversed as shown in FIG. 6B. The step of conjugating modified linkers to unconjugated sulfhydryl groups of the peptides may be performed prior to performing the step of removing payload by digesting the peptide mixture with papain. Regarding the step of conjugating modified linkers to an unconjugated sulfhydryl groups of the peptides, generally only free sulfhydryl groups are capable of conjugating to the modified linker. In some aspects, the method of the present application comprises digesting ADCs with trypsin to yield a peptide mixture, conjugating modified linkers to unconjugated sulfhydryl groups (e.g., labelling) of the peptide mixture; digesting the peptide mixture with papain to remove payloads; digesting the peptide mixture with Glu-C; and subjecting the peptide mixture to LC-MS analysis as shown in FIG. 6B.

Figure 6C:
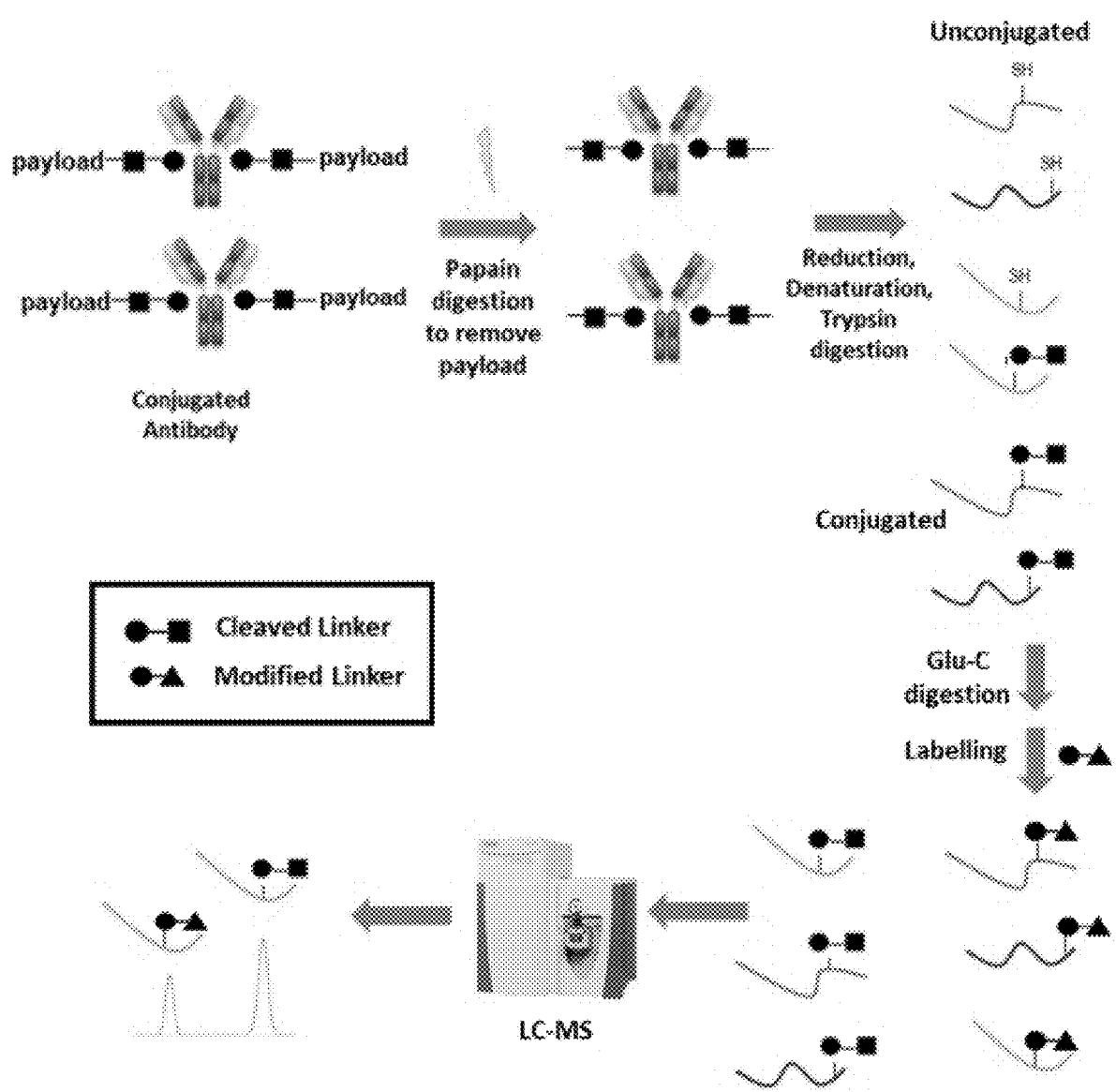
FIG. 6C shows an exemplary method of the present application comprising digesting ADC samples with papain to remove payloads, followed by reduction and denaturation, followed by digesting ADC samples with trypsin to obtain tryptic peptide mixture, digesting the tryptic peptide mixture with Glu-C, conjugating modified linkers to unconjugated sulfhydryl groups (e.g., labelling), and followed by subjecting the peptide mixture to LC-MS analysis according to an exemplary embodiment.

In other aspects, the sequence of the steps of the method of the present application may be rearranged as shown in FIG. 6C. The step of conjugating modified linkers to unconjugated sulfhydryl groups of the peptides may be performed after performing the step of removing payload by digesting the peptide mixture with papain and after performing the steps of trypsin and Glu-C digestions. In some aspects, papain digestion is performed prior to trypsin digestion to reduce non-specific digestion of papain on tryptic peptides. In some aspects, labelling step is performed after papain digestion to reduce the inhibition of papain (a cysteine protease) activity by maleimide linkers. In some preferred aspects, the method of the present application comprises digesting ADCs with papain to remove payloads, followed by reduction and denaturation, followed by digesting ADCs with trypsin to obtain tryptic peptide mixture, digesting the tryptic peptide mixture with Glu-C, followed by conjugating modified linkers to unconjugated sulfhydryl groups (e.g., labelling), and followed by subjecting the peptide mixture to LC-MS analysis as shown in FIG. 6C.

In some preferred aspects, in order to minimize the non-specific digestion of papain, the ADCs are initially digested with papain to remove payload prior to conducting other steps. In some aspects, the method of the present application comprises digesting ADC sample with papain to remove payloads, subsequently digesting the sample with trypsin, subsequently digesting the tryptic peptide mixture with Glu-C, subsequently conjugating modified linkers to unconjugated sulfhydryl groups (e.g., labelling), and subsequently subjecting the peptide mixture to LC-MS analysis.

In some aspects, the method of the present application comprises digesting ADCs with trypsin to obtain a tryptic peptide mixture, wherein the ADC comprises an antibody, at least one drug payload, and at least one cleavable linker containing a valine-alanine dipeptide, wherein the linker is attached to the sulfhydryl group of the cysteine residue of the antibody; digesting the tryptic peptide mixture with a papain to remove payload to obtain a papainic tryptic peptide mixture; conjugating modified linkers to unconjugated sulfhydryl groups of the papainic tryptic peptides; and subjecting the peptide mixture to mass analysis, such as LC-MS analysis. Optionally, the peptide mixture may subject to Glu-C protease digestion to reduce the number of hinge region peptides for simplified quantitation prior to conducting mass analysis.

In some aspects, the method of the present application comprises digesting a ADC mixture with a first enzyme to obtain a first peptide mixture, wherein the ADC comprises a peptide or protein, at least one payload, and at least one linker; digesting the first peptide mixture with a second enzyme to remove payload to obtain a second peptide mixture, wherein the second enzyme can also digest the peptides in the first peptide mixture; conjugating modified linkers to unconjugated conjugation sites in the peptides of the second peptide mixture to obtain a third peptide mixture; and analyzing the third peptide mixture using LC-MS. Optionally, the third peptide mixture may subject to a third enzyme digestion prior to LC-MS analysis to reduce the variable of the peptides for simplified LC-MS quantitation. In some preferred embodiments, the first enzyme is trypsin, the second enzyme is papain, and the third enzyme is Glu-C.

Figure 7:
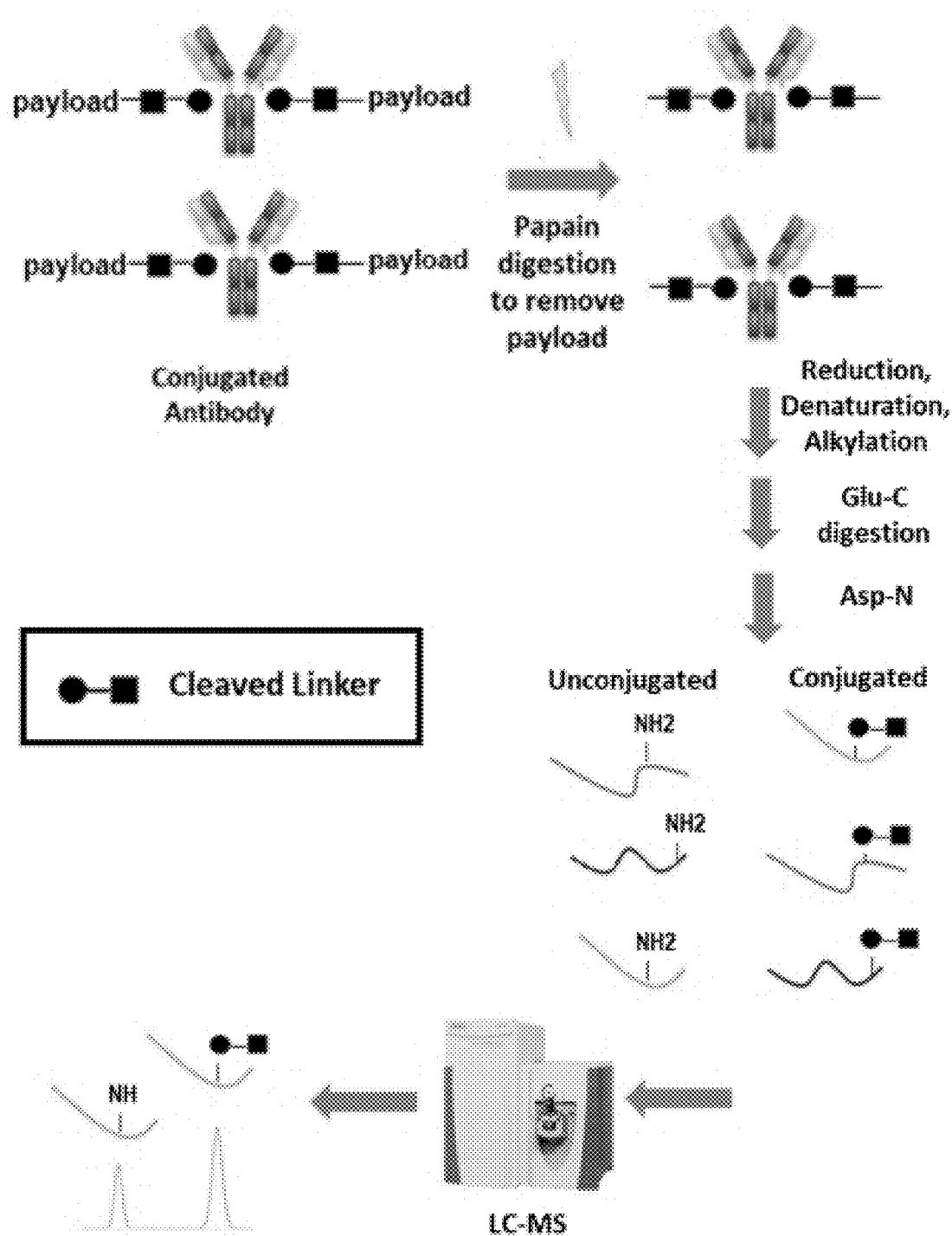
FIG. 7 shows an exemplary method of the present application comprising digesting ADC samples with papain to remove payloads, followed by reduction and denaturation, followed by alkylation, followed by digesting ADC samples with Glu-C to obtain Glu-C digested peptide mixture, digesting the peptide mixture with Asp-N, and followed by subjecting the peptide mixture to LC-MS analysis according to an exemplary embodiment.

In other aspects, the method of the present application comprises digesting lysine-linked ADCs with papain to remove payloads, followed by reduction and denaturation, followed by alkylation, followed by digesting ADC samples with Glu-C to obtain Glu-C digested peptide mixture, digesting the peptide mixture with Asp-N, and followed by subjecting the peptide mixture to LC-MS analysis as shown in FIG. 7. The site-specific payload (e.g., drug) conjugation can be calculated based on the quantitation of peptides containing cleaved linkers and native peptides which do not contain cleaved linkers, for example, site-specific payload (e.g., drug) conjugation=(quantity of peptides containing cleaved linker)/(quantity of peptides containing cleaved linkers+quantity of native peptides).

In yet other aspects, the present application provides a method to quantifying or characterizing drug conjugation of lysine-linked ADCs, the method comprising cleaving a drug payload using a first enzyme to generate an antibody containing a cleaved linker; followed by subjecting the sample to a second enzyme to obtain a peptide mixture; and subjecting the peptide mixture to mass analysis to quantify or characterize the specific lysine conjugation site based on quantifying the peptide containing the cleaved linker and/or the peptide which does not contain the cleaved linker.

The concerns of heterogeneity of ADC due to the presence of undesired ADC species have led to an increasing demand for quantitation and characterization of site-specific drug conjugations of ADC, such as site-specific quantitation of drug conjugation, to improve drug safety and efficacy. Exemplary embodiments disclosed herein satisfy the aforementioned demands. This disclosure provides methods to quantify or characterize conjugation of an attachment linked to a specific conjugation site of ADC to satisfy the aforementioned demands. They satisfy the long felt needs of site-specific quantitation or characterization of drug conjugations of ADCs to ensure the well-defined DARs and degree of homogeneity relevant to drug safety and efficacy.

Unless described otherwise, all technical and scientific terms used herein have the same meaning as commonly understood by one of ordinary skill in the art to which this invention belongs. Although any methods and materials similar or equivalent to those described herein can be used in the practice or testing, particular methods and materials are now described. Various publications, including patents, patent applications, published patent applications, technical articles and scholarly articles are cited throughout the specification. All of these cited references and mentioned publications are incorporated by reference, in their entireties and for all purposes, herein.

The term "a" should be understood to mean "at least one"; and the terms "about" and "approximately" should be understood to permit standard variation as would be understood by those of ordinary skill in the art; and where ranges are provided, endpoints are included. As used herein, the terms "include," "includes," and "including," are meant to be non-limiting and are understood to mean "comprise," "comprises," and "comprising," respectively.

In some aspects, the disclosure provides a method for quantifying or characterizing site-specific conjugation of at least one attachment linked to at least one specific conjugation site of a partially conjugated peptide or protein in a sample, comprising: cleaving a portion of the attachment to generate the peptide or protein containing a cleaved linker, wherein the attachment comprises the cleaved linker; adding a modified linker to an unconjugated conjugation site of the partially conjugated peptide or protein; and subjecting the sample to mass analysis to identify the peptide or protein containing the cleaved linker and/or the modified linker. In some aspects, in the method of the present application, the peptide or protein is an antibody, an antibody fragment, a Fab region of an antibody, a Fc region of an antibody, or a fusion protein.

As used herein, the term "conjugated peptide or protein" can refer to peptide or protein attached to biologically active drug(s) by linker(s) with labile bond(s) including "antibody-drug conjugate", or "ADC". A conjugated peptide, a conjugated protein, an antibody-drug conjugate, or an ADC can comprise several molecules of a biologically active drug (or the payload) which can be covalently linked to conjugation sites, such as side chains of amino acid residues of a conjugated peptide, a conjugated protein, or an antibody (Siler Panowski et al., *Site-specific antibody drug conjugates for cancer therapy*, 6 mAbs 34-45 (2013)). An antibody used for an ADC can be capable of binding with sufficient affinity for selective accumulation and durable retention at a target site. Most ADCs can have Kd values in the nanomolar range. The payload can have potency in the nanomolar/picomolar range and can be capable of reaching intracellular concentrations achievable following distribution of the ADC into target tissue. The linker that forms the connection between the payload and the antibody can be capable of being sufficiently stable in circulation to take advantage of the pharmacokinetic properties of the antibody moiety (e.g., long half-life) and to allow the payload to remain attached to the antibody as it distributes into tissues, yet should allow for efficient release of the biologically active drug once the ADC can be taken up into target cells. The linker can be: those that are non-cleavable during cellular processing and those that are cleavable once the ADC has reached the target site. With non-cleavable linkers, the biologically active drug released within the cell includes the payload and all elements of the linker still attached to an amino acid residue of the antibody, typically a lysine or cysteine residue, following complete proteolytic degradation of the ADC within the lysosome. Cleavable linkers are those whose structure includes a site of cleavage between the payload and the amino acid attachment site on the antibody. Cleavage mechanisms can include hydrolysis of acid-labile bonds in acidic intracellular compartments, enzymatic cleavage of amide or ester bonds by an intracellular protease or esterase, and reductive cleavage of disulfide bonds by the reducing environment inside cells.

As used herein, an "antibody" is intended to refer to immunoglobulin molecules consisting of four polypeptide chains, two heavy (H) chains and two light (L) chains inter-connected by disulfide bonds. Each heavy chain has a heavy chain variable region (HCVR or VH) and a heavy chain constant region. The heavy chain constant region contains three domains, CH1, CH2 and CH3. Each light chain has of a light chain variable region and a light chain constant region. The light chain constant region consists of one domain (CL). The VH and VL regions can be further subdivided into regions of hypervariability, termed complementarity determining regions (CDR), interspersed with regions that are more conserved, termed framework regions (FR). Each VH and VL can be composed of three CDRs and four FRs, arranged from amino-terminus to carboxy-terminus in the following order: FR1, CDR1, FR2, CDR2, FR3, CDR3, FR4. The term "antibody" includes reference to both glycosylated and non-glycosylated immunoglobulins of any isotype or subclass. The term "antibody" is inclusive of, but not limited to, those that are prepared, expressed, created or isolated by recombinant means, such as antibodies isolated from a host cell transfected to express the antibody. An IgG comprises a subset of antibodies.

As used herein, the term "peptide" or "protein" includes any amino acid polymer having covalently linked amide bonds. Proteins comprise one or more amino acid polymer chains, generally known in the art as "peptide" or "polypeptides". A protein may contain one or multiple polypeptides to form a single functioning biomolecule. In some aspects, the protein can be an antibody, a bispecific antibody, a multispecific antibody, antibody fragment, monoclonal antibody, host-cell protein or combinations thereof.

As used herein, the term an "antibody fragment" includes a portion of an intact antibody, such as, for example, the antigen-binding or variable region of an antibody. Examples of antibody fragments include, but are not limited to, a Fab fragment, a Fab' fragment, a F(ab')2 fragment, a Fc fragment, a scFv fragment, a Fv fragment, a dsFv diabody, a dAb fragment, a Fd' fragment, a Fd fragment, and an isolated complementarity determining region (CDR) region, as well as triabodies, tetrabodies, linear antibodies, single-chain antibody molecules, and multi specific antibodies formed from antibody fragments. Fv fragments are the combination of the variable regions of the immunoglobulin heavy and light chains, and ScFv proteins are recombinant single chain polypeptide molecules in which immunoglobulin light and heavy chain variable regions are connected by a peptide linker. An antibody fragment may be produced by various means. For example, an antibody fragment may be enzymatically or chemically produced by fragmentation of an intact antibody and/or it may be recombinantly produced from a gene encoding the partial antibody sequence. Alternatively or additionally, an antibody fragment may be wholly or partially synthetically produced. An antibody fragment may optionally comprise a single chain antibody fragment. Alternatively or additionally, an antibody fragment may comprise multiple chains that are linked together, for example, by disulfide linkages. An antibody fragment may optionally comprise a multi-molecular complex.

In some aspects, in the method of the present application, the sample is subjected to mass analysis to identify the peptide or protein containing the cleaved linker and/or the modified linker. In some aspects, the method of the present application further comprises quantifying or characterizing the site-specific conjugation of the attachment based on quantifying the cleaved linker and the modified linker. In some aspects, the mass analysis in the method of the present application is a mass spectroscopy or a liquid chromatography-mass spectroscopy. In some embodiment, the mass spectroscopy in the method of the present application can be conducted using an electrospray ionization mass spectrometer, nano-electrospray ionization mass spectrometer, or a triple quadrupole mass spectrometer, wherein the mass spectrometer can be coupled to a liquid chromatography system, wherein the mass spectrometer is capable of performing a LC-MS (liquid chromatography-mass spectrometry), a LC-MRM-MS (liquid chromatography-multiple reaction monitoring-mass spectrometry) or a LC-MS/MS analyses.

As used herein, a "mass spectrometer" includes a device capable of identifying specific molecular species and measuring their accurate masses. The term is meant to include any molecular detector into which a polypeptide or peptide may be eluted for detection and/or characterization. A mass spectrometer can include three major parts: the ion source, the mass analyzer, and the detector. The role of the ion source is to create gas phase ions. Analyte atoms, molecules, or clusters can be transferred into gas phase and ionized either concurrently (as in electrospray ionization). The choice of ion source depends heavily on the application.

As used herein, the term liquid "chromatography" refers to a process in which a chemical mixture carried by a liquid or gas can be separated into components as a result of differential distribution of the chemical entities as they flow around or over a stationary liquid or solid phase. Non-limiting examples of chromatography include traditional reversed-phased (RP), ion exchange (IEX), mixed mode chromatography and normal phase chromatography (NP).

As used herein, the term "electrospray ionization" or "ESI" refers to the process of spray ionization in which either cations or anions in solution are transferred to the gas phase via formation and desolvation at atmospheric pressure of a stream of highly charged droplets that result from applying a potential difference between the tip of the electrospray needle containing the solution and a counter electrode. There are generally three major steps in the production of gas-phase ions from electrolyte ions in solution. These are: (a) production of charged droplets at the ES infusion tip; (b) shrinkage of charged droplets by solvent evaporation and repeated droplet disintegrations leading to small highly charged droplets capable of producing gas-phase ions; and (c) the mechanism by which gas-phase ions are produced from very small and highly charged droplets. Stages (a)-(c) generally occur in the atmospheric pressure region of the apparatus. In some aspects, the electrospray ionization mass spectrometer can be a nano-electrospray ionization mass spectrometer.

As used herein, the term "triple quadruple mass spectrometer" refers to a tandem mass spectrometer consisting of two quadrupole mass analyzers in series, with a (non-mass-resolving) radio frequency (RF), only quadrupole between them to act as a cell for collision-induced dissociation. In a triple quadrupole mass spectrometer, a peptide sample is injected onto an LC coupled with a MS instrument. The first quadrupole can be used as a mass filter to isolate peptides with a targeted m/z. The second quadrupole serves as a collision cell to break the peptide into fragments. The third quadrupole serves as a second mass filter for specified m/z fragments from the initial parent peptide. As used herein, the term "tandem mass spectrometry" includes a technique where structural information on sample molecules can be obtained by using multiple stages of mass selection and mass separation. A prerequisite is that the sample molecules can be transferred into gas phase and ionized intact and that they can be induced to fall apart in some predictable and controllable fashion after the first mass selection step. Multistage MS/MS, or MS$^n$, can be performed by first selecting and isolating a precursor ion (MS$^2$), fragmenting it, isolating a primary fragment ion (MS$^3$), fragmenting it, isolating a secondary fragment (MS$^4$), and so on as long as one can obtain meaningful information or the fragment ion signal can be detectable. Tandem MS have been successfully performed with a wide variety of analyzer combinations. What analyzers to combine for a certain application can be determined by many different factors, such as sensitivity, selectivity, and speed, but also size, cost, and availability. The two major categories of tandem MS methods are tandem-in-space and tandem-in-time, but there are also hybrids where tandem-in-time analyzers are coupled in space or with tandem-in-space analyzers. A tandem-in-space mass spectrometer comprises an ion source, a precursor ion activation device, and at least two non-trapping mass analyzers. Specific m/z separation functions can be designed so that in one section of the instrument ions are selected, dissociated in an intermediate region, and the product ions are then transmitted to another analyzer for m/z separation and data acquisition. In tandem-in-time mass spectrometer ions produced in the ion source can be trapped, isolated, fragmented, and m/z separated in the same physical device.

EXEMPLARY EMBODIMENTS

Embodiments disclosed herein provide methods for quantifying or characterizing conjugation of at least one attachment linked to at least one specific conjugation site of a partially conjugated peptide or protein in a sample.

In some aspects, the disclosure provides a method for quantifying or characterizing conjugation of at least one attachment linked to at least one specific conjugation site of a partially conjugated peptide or protein in a sample, comprising: cleaving a portion of the attachment to generate the peptide or protein containing a cleaved linker, wherein the attachment comprises the cleaved linker; adding a modified linker to an unconjugated conjugation site of the partially conjugated peptide or protein; and subjecting the sample to mass analysis to identify the peptide or protein containing the cleaved linker and/or the modified linker.

In some aspects, the portion of the attachment is cleaved using an enzyme, such as papain, cathepsin B, or plasmin, wherein a ratio of enzyme to substrate is from about 1:0.1 to about 1:100, from about 1:10 to about 1:300, from about 1:10 to about 1:250, preferably about 1:20, preferably about 1:200, about 1:0.2, about 1:0.5, about 1:1, about 1:1.5, about 1:2, about 1:3, about 1:4, about 1:5, about 1:10, about 1:15, about 1:25, about 1:30, about 1:35, about 1:40, about 1:45, about 1:50, about 1:55, about 1:60, about 1:65, about 1:70, about 1:75, about 1:80, about 1:85, about 1:90, or about 1:95. The enzymatic digestion is conducted at about 25-45° C. for about from 1 min to overnight; at about 37° C. for about 0.5 hour, preferably about 1 hour, about 1.5 hour, about 2 hour, about 3 hour, or less than 4 hr.

In other aspects, a modified linker is added to an unconjugated conjugation site of the partially conjugated peptide or protein. The modified linker is incubated with peptides at room temperature for about 2 hr, or at about 18-37° C. for about 1 min to overnight, wherein the peptide to linker molar ratio is preferably about 1:500, about from 1:10 to about 1:2000, about 1:20, about 1:50, about 1:100, about 1:200, about 1:300, about 1:400, about 1:600, about 1:700, about 1:800, about 1:1000, about 1:1200, about 1:1500, or about 1:1800.

It is understood that the method is not limited to any of the aforesaid peptides, proteins, antibodies, anti-drug antibodies, antigen-antibody complex, protein pharmaceutical products, chromatography column, or mass spectrometer.

The consecutive labeling of method steps as provided herein with numbers and/or letters is not meant to limit the method or any embodiments thereof to the particular indicated order.

The disclosure will be more fully understood by reference to the following Examples, which are provided to describe the disclosure in greater detail. They are intended to illustrate and should not be construed as limiting the scope of the disclosure.

EXAMPLES

Material and Method
1. Cleavable and Modified Linkers

Figure 8A:
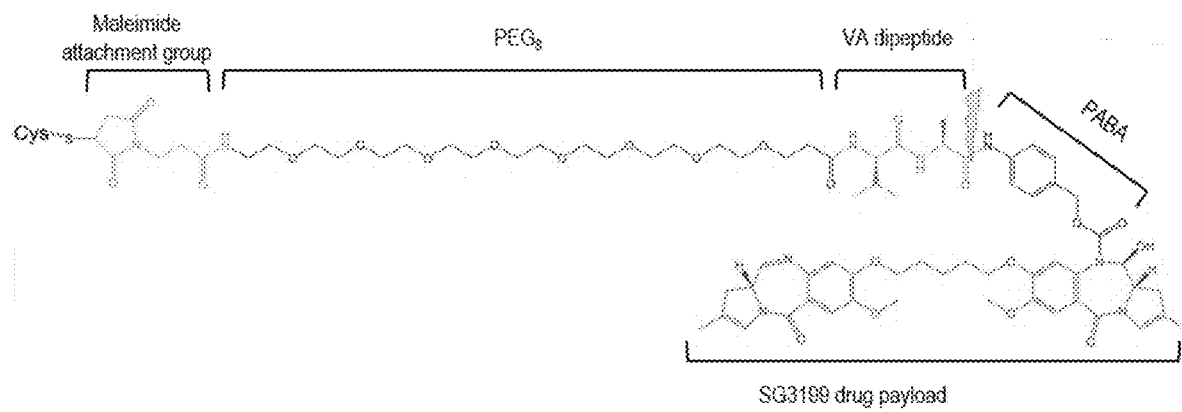
FIG. 8A shows an attachment of a linker, for example, LK1 linker, for connecting a protein and a payload through a maleimide attachment group according to an exemplary embodiment. The maleimide attachment group is attached to the sulfhydryl group (—SH) of the peptide or protein. The attachment of LK1 linker (mal-amido-PEG8-VA-PABA) includes a PEG8 (polyethylene glycol-8), a valine-alanine dipeptide (VA dipeptide), and a PABA. SG3199 is a drug payload.
Figure 8B:
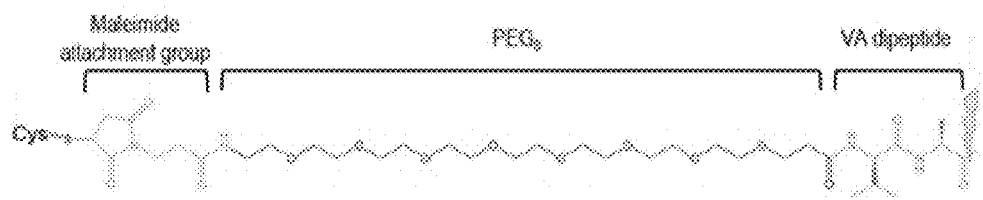
FIG. 8B shows an attachment of a cleaved linker (mal-amido-PEG8-VA), for example, the attachment of cleaved LK1, which is generated after protease digestion of LK1 to release payload by removing PABA and drug payload according to an exemplary embodiment.
Figure 8C:
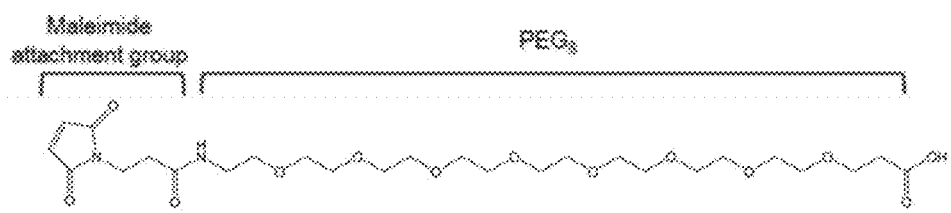
FIG. 8C shows an attachment of a modified linker of LK1 (mal-amido-PEG8—COOH), for example, the attachment of LK2, according to an exemplary embodiment.

LK1 is a cleavable linker for connecting a protein and a payload, as shown in FIG. 8A. LK1 contains a specific amino acid sequence as an enzymatic cleaving site, e.g., a valine-alanine dipeptide (VA dipeptide) which is recognizable by proteases, such as cathepsin B or papain. LK1 linker can be conjugated to a sulfhydryl group of a cysteine residue of a peptide or a protein through a maleimide attachment group (mal-amido). As shown in FIG. 8A, an attachment of LK1 linker, e.g., mal-amido-PEG8-VA-PABA, includes a PEG8 (polyethylene glycol-8) as a first spacer, a valine-alanine dipeptide as an enzymatic cleavage site, and a PABA as a second spacer. SG3199, a cytotoxic compound, is a drug payload which is loaded to LK1. FIG. 8B shows an attachment of a cleaved LK1, e.g., mal-amido-PEG8-VA, which is generated after protease digestion of LK1 to release payload, wherein PABA and payload are removed from the conjugate. LK1 including payload is designated as +1495.7 and cleaved LK1 is designated as +762.2 during mass analysis. LK2, e.g., modified linker of LK1 (modified LK1), is a linker containing a PEG8. FIG. 8C shows an attachment of LK2 linker. LK2 linker can be conjugated to a sulfhydryl group of a cysteine residue of a peptide or a protein through a maleimide attachment group (mal-amido). There is a mass difference between cleaved LK1 (FIG. 8B) and LK2 (FIG. 8C), since LK2 does not contain valine-alanine dipeptide. LK2 can be conjugated to a sulfhydryl group of a cysteine residue of a peptide or a protein through a maleimide attachment group, e.g., mal-amido-PEG8-COOH. LK2 is designated as +592.3 during mass analysis. LK1 including payload is designated as +1495.7 and cleaved LK1 is designated as +762.2 during mass analysis. The molecular weight of PABA (para-aminobenzylalcohol) is about 137.1 Da. The molecular weight of SG3199 (a drug payload) is about 584.7 Da.

Figure 8D:
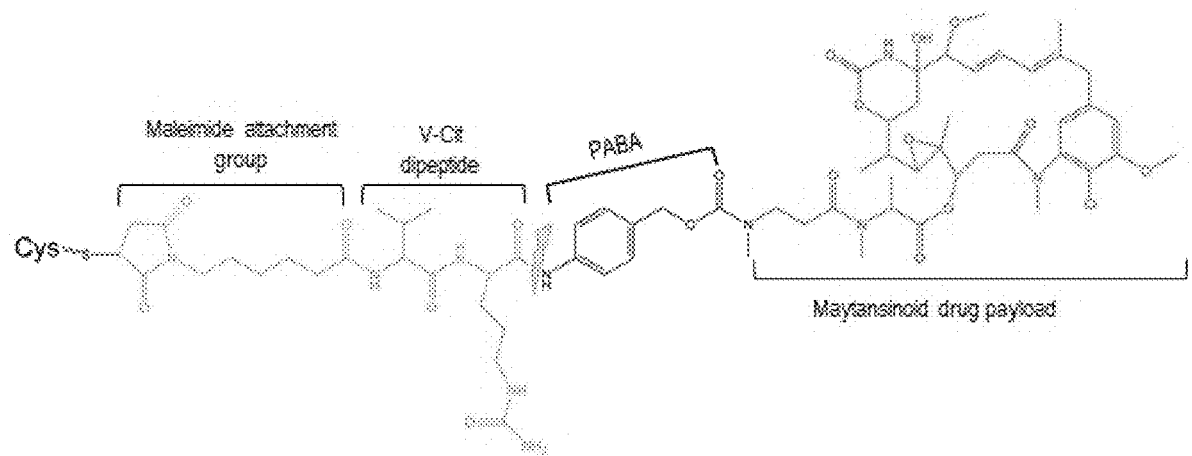
FIG. 8D shows an attachment of a linker, for example, LK3 linker, for connecting a protein and a payload through a maleimide attachment group according to an exemplary embodiment. The maleimide attachment group is attached to the sulfhydryl group (—SH) of the peptide or protein. The attachment of LK3 linker (mal-amido-Val-Cit-PABA) includes a valine-citrulline dipeptide (VCit dipeptide) and a PABA. Maytansinoid is a drug payload.
Figure 8E:
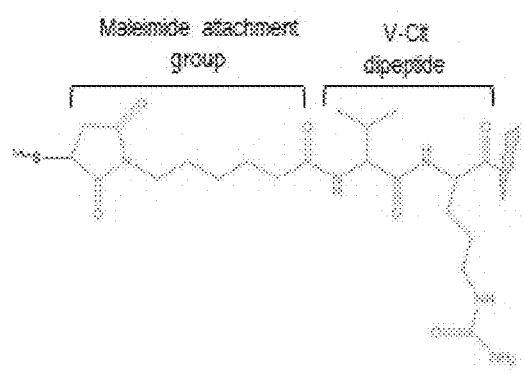
FIG. 8E shows an attachment of a cleaved linker (mal-amido-Val-Cit), for example, the attachment of cleaved LK3, which is generated after protease digestion of LK3 to release payload by removing PABA and drug payload according to an exemplary embodiment.
Figure 8F:
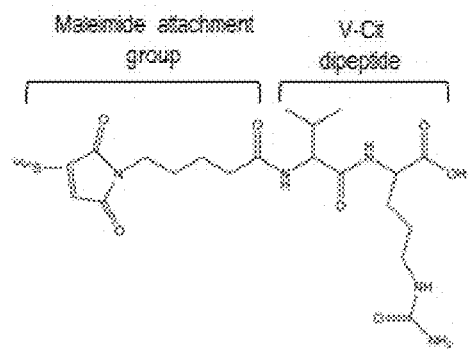
FIG. 8F shows an attachment of a modified linker of LK3 (mal-amido-Val-Cit), for example, the attachment of LK4, according to an exemplary embodiment.

LK3 is a cleavable linker for connecting a protein and a payload, as shown in FIG. 8D. LK3 contains a specific amino acid sequence as an enzymatic cleaving site, e.g., a valine-citrulline dipeptide (Val-Cit dipeptide) which is recognizable by proteases, such as cathepsin B or papain. LK3 linker can be conjugated to a sulfhydryl group of a cysteine residue of a peptide or a protein through a maleimide attachment group (mal-amido). As shown in FIG. 8D, an attachment of LK3 linker, e.g., mal-amido-Val-Cit-PABA, includes a valine-citrulline dipeptide as an enzymatic cleavage site and a PABA as a spacer. Maytansinoid (May), a cytotoxic compound, is a drug payload which is loaded to LK3. FIG. 8E shows an attachment of a cleaved LK3, e.g., mal-amido-Val-Cit, which is generated after protease digestion of LK3 to release payload, wherein PABA and payload are removed from the conjugate. LK3 including payload is designated as +1332.6 and cleaved LK3 is designated as +467.2 during mass analysis. LK4, e.g., modified linker of LK3 (modified LK3), is a linker containing a valine-citrulline dipeptide. FIG. 8F shows an attachment of LK4 linker. LK4 linker can be conjugated to a sulfhydryl group of a cysteine residue of a peptide or a protein through a maleimide attachment group (mal-amido), e.g., mal-amido-Val-Cit. LK4 is designated as +453.2 during mass analysis. LK3 including payload maytansinoid is designated as +1332.6 and cleaved LK3 is designated as +467.2 during mass analysis.

Figure 8G:
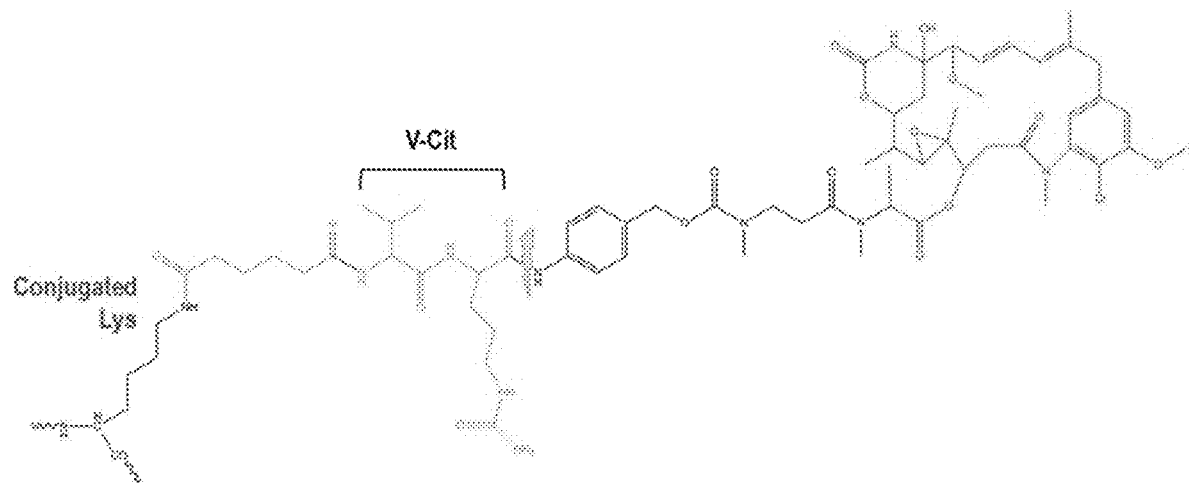
FIG. 8G shows an attachment of LK5 linker, for example, adip-Val-Cit-PAB-NMe, including a valine-citrulline dipeptide as an enzymatic cleavage site for connecting a protein and a payload according to an exemplary embodiment. Maytansinoid (May), a cytotoxic compound, is a drug payload which is loaded to LK5 according to an exemplary embodiment.
Figure 8H:
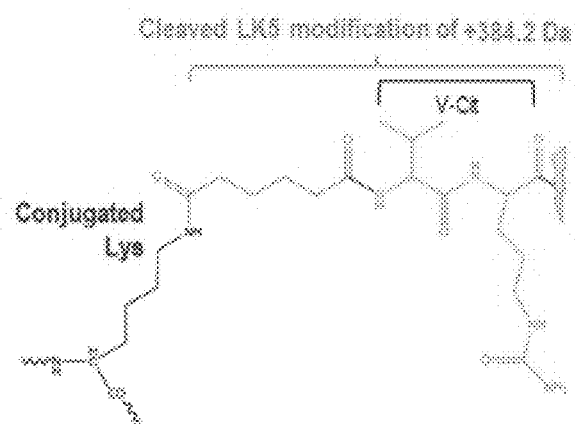
FIG. 8H shows an attachment of a cleaved LK5, for example, adip-Val-Cit, which is generated after protease digestion of LK5 to release payload according to an exemplary embodiment.
Figure 8I:
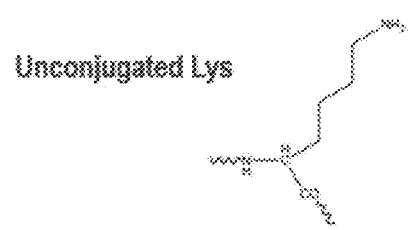
FIG. 8I shows a chemical structure of an unconjugated lysine residue of an antibody according to an exemplary embodiment.

LK5 is a cleavable linker for connecting a protein and a payload, as shown in FIG. 8G. LK5 contains a specific amino acid sequence as an enzymatic cleaving site, e.g., a valine-citrulline dipeptide (Val-Cit dipeptide) which is recognizable by proteases, such as cathepsin B or papain. LK5 linker can be conjugated to a lysine residue of a peptide or a protein through lysine amide coupling using activated carboxylic acid ester or NHS ester. As shown in FIG. 8G, an attachment of LK5 linker, e.g., adip-Val-Cit-PAB-NMe, includes a valine-citrulline dipeptide as an enzymatic cleavage site. Maytansinoid (May), a cytotoxic compound, is a drug payload which is loaded to LK5. FIG. 8H shows an attachment of a cleaved LK5, e.g., adip-Val-Cit, which is generated after protease digestion of LK5 to release payload. LK5 including payload is designated as +1249.6 and cleaved LK5 is designated as +384.2 during mass analysis. FIG. 8I shows a chemical structure of an unconjugated lysine residue of an antibody.

2. Preparation of Antibody-Drug Conjugates (ADC)

Figure 9A:
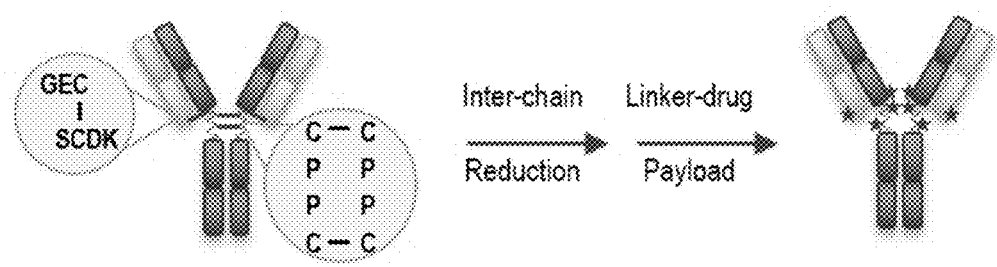
FIG. 9A shows the inter-chain disulfide bonds of the antibody, which were reduced to derive sulfhydryl groups (—SH). The sulfhydryl groups were subsequently used as conjugation sites for preparing ADC according to an exemplary embodiment. Figure discloses SEQ ID NOS 7, 13, and 13, respectively, in order of appearance.
Figure 9B:
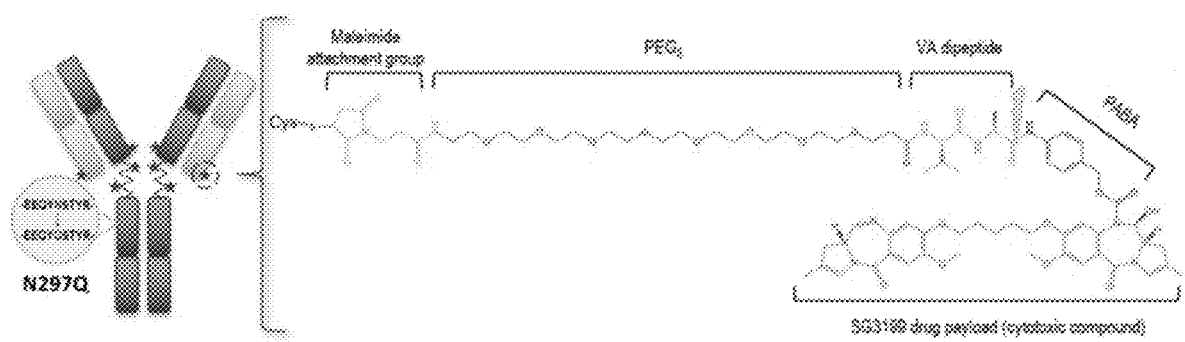
FIG. 9B shows an ADC containing LK1 linker and payload drug SG3199. The ADC, for example, Ab-mal-amido-PEGS-VA-PABA-SG3199, has a cleavage site for releasing drug payload according to an exemplary embodiment. Figure discloses SEQ ID NOS 14-15, respectively, in order of appearance.

MAB1, e.g., a monoclonal antibody (IgG1) with mutation in residue 297 (N297Q), was used to prepare ADCs. Due to the mutation in residue 297, MAB1 has loss of glycosylation site. As shown in FIG. 9A, the inter-chain disulfide bonds of the antibody were reduced to derive sulfhydryl groups (—SH) in the cysteine residues of the antibody. The sulfhydryl groups were subsequently used as conjugation sites for preparing ADC. ADC sample buffer contained PBS with 5% glycerol. As shown in FIG. 9B, LK1 linker which was loaded with payload drug SG3199 was conjugated to the cysteine residue of MAB1 through a maleimide attachment group to derive ADC. The derived MAB1-LK1 ADC, e.g., Ab-mal-amido-PEG8-VA-PABA-SG3199, has a cleavage site for releasing drug payloads. The DAR of MAB1-LK1-SG3199 ADC is about 3.6. The molecular weight of LK1 including payload SG3199 is about 1495.7 Da. The length of PEG spacer arm, e.g., PEG8, is about 30.8 Å. The protease cleavable site of MAB1-LK1-SG3199 ADC is a valine-alanine dipeptide (Val-Ala or VA).

Figure 9C:
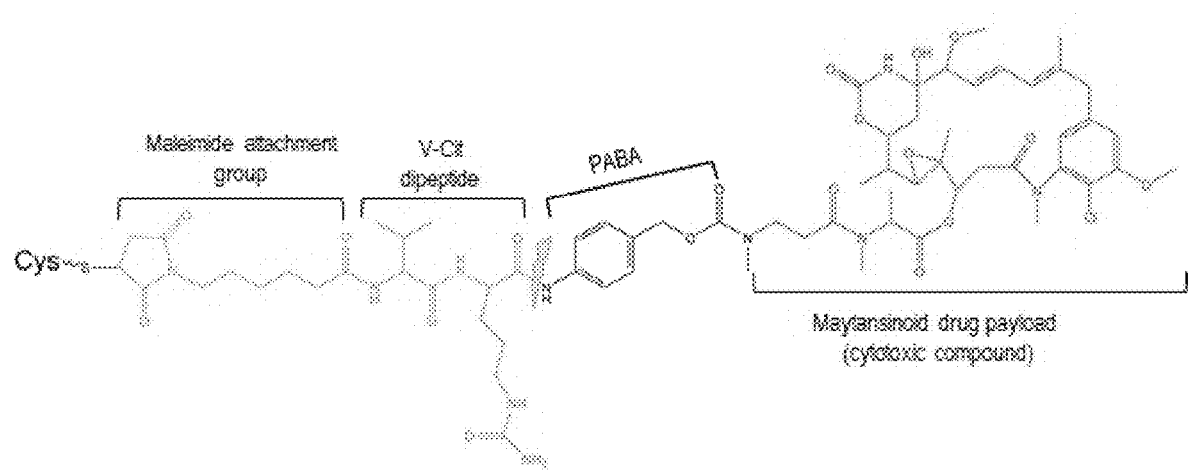
FIG. 9C shows an ADC containing LK3 linker and payload drug maytansinoid. The ADC, for example, Ab-mal-amido-Val-Cit-PABA-maytansinoid, has a cleavage site for releasing drug payload according to an exemplary embodiment.

As shown in FIG. 9C, LK3 linker which was loaded with payload drug maytansinoid (May) was conjugated to the cysteine residue of MAB1 through a maleimide attachment group to derive ADC. The derived MAB1-LK3-May ADC, e.g., Ab-mal-amido-Val-Cit-PABA-maytansinoid (Ab-MC-VCit-PABA-NME-May), has a cleavage site for releasing drug payload. The DAR of MAB1-LK3-May ADC is about 2.2. The molecular weight of LK3 including payload maytansinoid is about 1332.6 Da. The protease cleavable site of MAB1-LK3-May ADC is a valine-citrulline dipeptide (Val-Cit or VCit). L-citrulline (Cit) is a naturally occurring amino acid which can be converted to L-arginine and nitric oxide.

Lysine-linked antibody conjugates were prepared using MAB2 and LK5. LK5 linkers were conjugated to lysine residues of MAB2 through lysine amide coupling using activated carboxylic acid ester or NHS ester. There are about 25 lysine residues in each heavy chain and about 10 lysine residues in each light chain. MAB2 is a bispecific antibody which targets two distinct epitopes. Two different lots of MAB2-LK5 ADCs were prepared, which had DAR values of about 2.9 and 2.7 respectively.

3. Glu-C Digestion

Glu-C is a serine protease isolated from *Staphylococcus aureus*. Glu-C, e.g., V-8 protease, is an endoproteinase which specifically cleaves the carboxyl side of glutamic residues when reactions are carried out in ammonium bicarbonate and ammonium acetate buffers, generating a limited number of peptide fragments. Glu-C cleavage can also occur at both glutamic and aspartic residues in phosphate buffers. Glu-C is a highly specific endoproteinase for improving sequence coverage in mass spectrometry protein identification applications. Glu-C can be used alone or alongside trypsin or other proteases to produce complementary protein digests for peptide mapping and protein sequencing. Glu-C can reduce hinge region peptide C-terminal heterogeneities (TH↑T↑CPPCPAPE↑L (SEQ ID NO: 8)).

4. Asp-N Digestion

Asp-N is a zinc metalloproteinase which can be used alone or in parallel with trypsin or other proteases to produce protein digestions for peptide mapping and protein sequencing. Asp-N is an endoproteinase which cleaves primarily at amino side of aspartate residues and cysteic acid residues that result from the oxidization of cysteine residues, generating a limited number of peptide fragments. Asp-N cleavage can also occur at glutamic residues. AspN can efficiently digest protein in 2-20 hours at 37° C.

5. Experimental Reagent Preparation 4.1. Mobile Phase A (0.05% TFA in Milli-Q water) for mass spectrometry: Add 1 mL of TFA (trifluoroacetic acid) to 2 L of Milli-Q water in a 2 L Pyrex glass bottle. Invert the bottle 3-4 times to mix. Store at room temperature for up to 3 months.

4.2. Mobile Phase B (0.045% TFA in acetonitrile) for mass spectrometry: Add 0.45 mL of TFA to 1 L of acetonitrile in a 1 L Pyrex glass bottle. Invert the bottle 3-4 times to mix. Store at room temperature for up to 3 months.

4.3. 5 mM acetic acid solution: Dilute 14.3 µL of glacial acetic acid to 50 mL with Milli-Q water, and mix well. Store at 4° C. for up to 3 months.

4.4. 0.1 M TCEP stock solution: Dissolve 28.7 mg of TCEP-HCl (Tris(2-Carboxyethyl) phosphine Hydrochloride) in Milli-Q water, and adjust the final volume to 1 mL. Make aliquots of 50 µL, and store at −20° C. for up to 3 months.

4.5. 8 M urea in 100 mM Tris-HCl: Dissolve 0.48 g urea in 640 µL of 100 mM Tris-HCl, pH 7.5 to make the final volume to 1 mL. Vortex until completely dissolved, and centrifuge at 14,000 g for 3 minutes using a Microcentrifuge. Make fresh each time. 0.4829 g of urea was weighed for the experiment.

4.6. 5% TFA solution: Dilute 10 uL of TFA with 190 uL of Milli-Q water, mix well.

4.7. 0.1 mg/uL new label stock solutions: Dissolve 10 mg of each label in 100 uL of DMSO (dimethyl sulfoxide), making it 0.1 mg/uL stock solution. Prepare aliquot of 2 uL/EA 4.8. Papain activation buffer (1.1 mM EDTA, 0.067 mM mercaptoethanol and 5.5 mM cysteine): Add 4.4 uL of 0.5 M EDTA, 2.4 uL of 55 mM mercaptoethanol and 1.73 mg cysteine to 2 mL of water, mix well.

6. Method of Testing New Labels

According to the concentration of ADC samples, transfer 25 µg of each ADC sample to a new microcentrifuge tube and add water to a total volume of 10 µL. Dilute 20 uL of papain suspension (10 mg/mL) with 180 uL of papain digestion buffer, incubate at 37° C. for 30 min. Dilute 30 uL of papain (nominal concentration of 1 mg/mL) with 120 uL of activation buffer to a nominal concentration of 0.2 mg/mL. Measure papain concentration with UV (ultraviolate) measurement at 280 nm and 320 nm using papain activation buffer as the blank buffer. Dilute activated papain to a final concentration of 0.1 mg/mL with papain activation buffer. Add 1.25 uL of 0.1 mg/mL papain solution (enzyme: substrate ratio is 1:200) to intact ADC, incubate at 37° C. for 1 h. Add 0.5 µL of 0.1 M TCEP-HCl to each sample. Vortex the samples for 3 seconds, and then spin down the samples using a Minicentrifuge for 3 seconds. Incubate samples at 95° C. for 20 minutes with shaking at 800 rpm in a thermomixer. Following incubation, cool down the samples to room temperature for 5 minutes. Spin down the condensation using a Minicentrifuge for 3 seconds. Add 6 µL of 8 M urea in 1 M Tris-HCl, pH 7.5 to each sample. Reconstitute sequencing grade modified trypsin (20 µg/vial) in 520 µL of Milli-Q water to a final concentration of 0.038 µg/µL. If multiple vials of trypsin are needed, combine the trypsin solutions from different vials. Add 32.5 µL of 0.038 µg/µL trypsin solution to each sample. Incubate the samples at 37° C. in the dark for 3 hours with shaking at 800 rpm in a ThermoMixer. Dilute 0.1 M TCEP to 0.05 M TCEP with water. Transfer 0.8 uL of 0.05 M TCEP to each sample. Reconstitute sequencing grade Glu-C (10 ug/vial) in 40 uL of Milli-Q water to a final concentration of 0.25 ug/uL. Add 5 uL of 0.25 ug/uL Glu-C solution to each sample. Incubate the samples at 37° C. in the dark for 1.5 h with shaking at 800 rpm in a ThermoMixer. Dilute the labeling linker with DMSO or water, transfer the labeling linker (based on the linker structures of different ADCs) to each sample to make an excessive of linker compared to free sulfhydryl groups of the ADC. Incubate at room temperature for 2 h. Acidify the digestion mixtures with 0.6 uL of 5% TFA. Inject 10 µL of each sample onto a Waters Acquity I-Class UPLC coupled to a Thermo Scientific Q Exactive or Q Exactive Plus Hybrid Quadrupole-Orbitrap Mass Spectrometer. Store the rest of digested samples in a −80° C. freezer. Freeze the rest of solution for enzyme labeling optimization experiment.

Example 1. Identification of Drug-Antibody Ratio of MAB1-LK1 ADC

Figure 10:
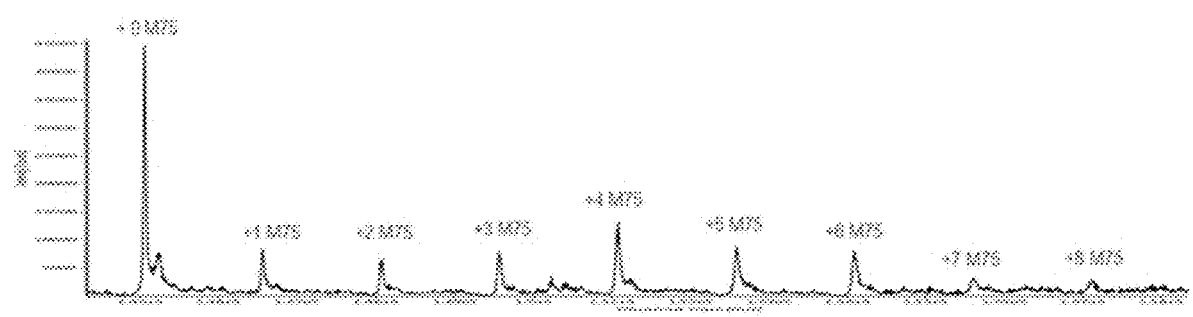
FIG. 10 shows the determination of drug-antibody ratio of MAB1-LK1 ADC using intact mass according to an exemplary embodiment. (X axis: intensity/[counts]; Y axis: observed mass [m/z] from 1.45 e5 to 1.58 e5).

The drug-antibody ratio (DAR) of MAB1-LK1 ADC was determined using intact mass. The average DAR was calculated and estimated as 2.34 as shown in FIG. 10 (X axis: intensity/[counts]; Y axis: observed mass [m/z] from 1.45 e5 to 1.58 e5). The MAB1-LK1 ADC are heterogenous and have various variants, such as size variants and charge variants.

Example 2. Removing Payloads from ADCs

Figure 11:
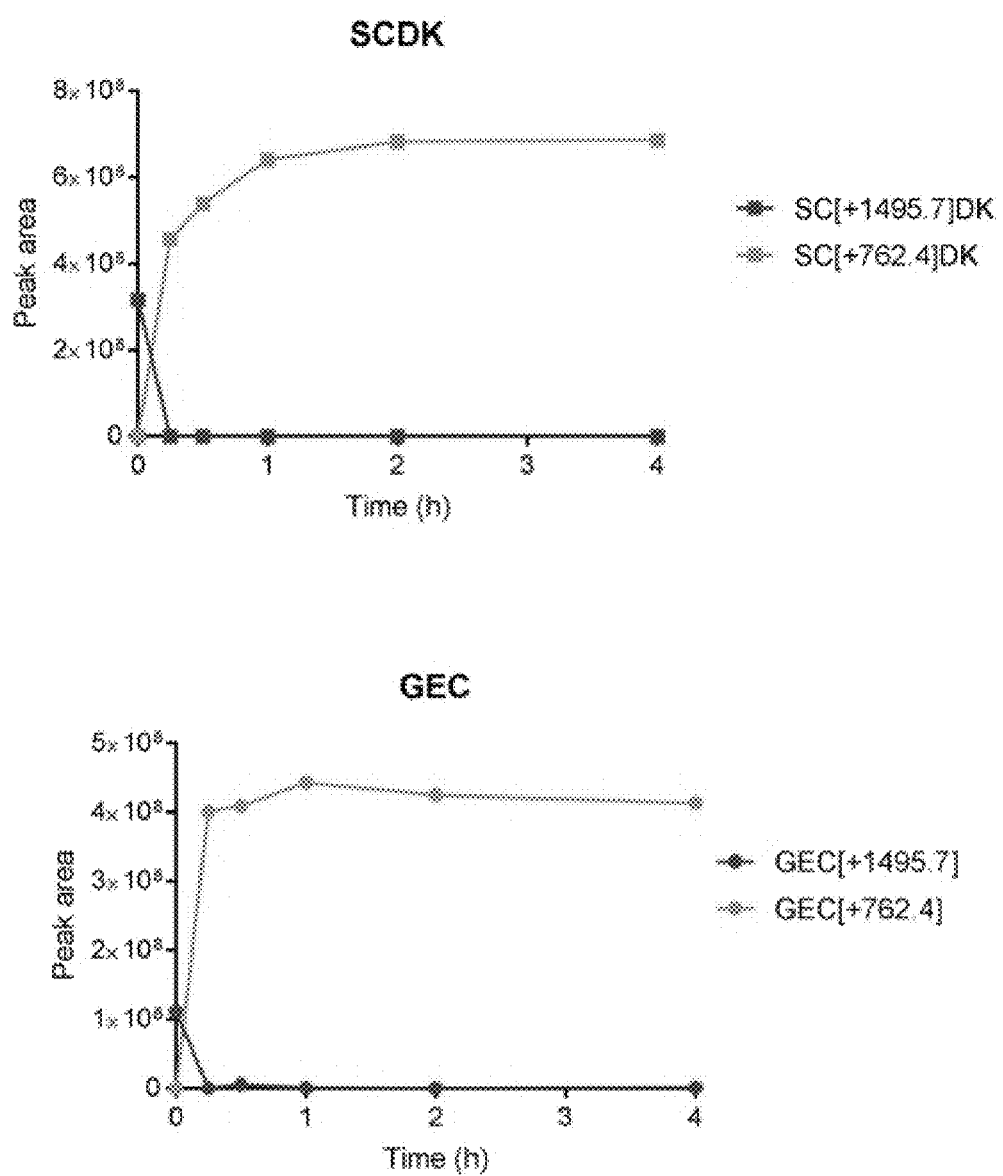
FIG. 11 shows the removal of drug payloads using papain from MAB1-LK1 ADCs according to an exemplary embodiment. MAB1-LK1 ADCs were digested with trypsin to obtain a tryptic peptide mixture. Two tryptic peptides, e.g., SCDK (serine-cysteine-aspartic acid-lysine) (SEQ ID NO: 7) and GEC (glycine-glutamic acid-cysteine), were analyzed using LC-MS according to an exemplary embodiment. LK1 is designated as +1495.7 (including payload) and cleaved LK1 is designated as +762.2 during mass analysis.

Papain was used to remove the payloads of MAB1-LK1 ADCs. Papain (1 mg/mL) was activated in papain activation buffer (1.1 mM EDTA, 0.067 mM mercaptoethanol and 5.5 mM cysteine) at 37° C. for 30 minutes. MAB1-LK1 ADCs were digested with trypsin to obtain a tryptic peptide mixture. Subsequently, the tryptic peptide mixture was digested using activated papain at 37° C. for about or less than 4 hr to remove payloads, e.g., SG3199. The ratio of enzyme to substrate is 1:20. The inter-chain disulfide bonds between heavy chain and light chain were reduced. Two tryptic peptides, e.g., SCDK (serine-cysteine-aspartic acid-lysine) (SEQ ID NO: 7) and GEC (glycine-glutamic acid-cysteine), were analyzed using LC-MS. The payloads were removed completely within 1 hr as shown in FIG. 11. Papain can recognize valine-alanine dipeptide in LK1 linker. The cleavage site of papain is between valine-alanine dipeptide and PABA as shown in FIG. 9B. PABA and SG3199 were removed from the attachment of LK1 linker after papain digestion resulting the mass loss. The tryptic peptide contains LK1 is labelled as +1495.7 (including payload) in FIG. 11. The tryptic peptide contains cleaved LK1 is labelled as +762.4 in FIG. 11.

The complete cleavage of removing payloads using papain digestion was reached at enzyme to substrate ratio of 1:20 for 1 hour at 37° C. The papain activity was quenched using a reversible papain inhibitor (such as GGYR (SEQ ID NO: 9)) or an irreversible papain inhibitor (such as chyomstatin) in combination with a heating step at 95° C. for 20 minutes to end the digestion reaction.

Example 3. Digesting Tryptic Hinge Region Peptide Using Papain

Figures 12A, 12B:
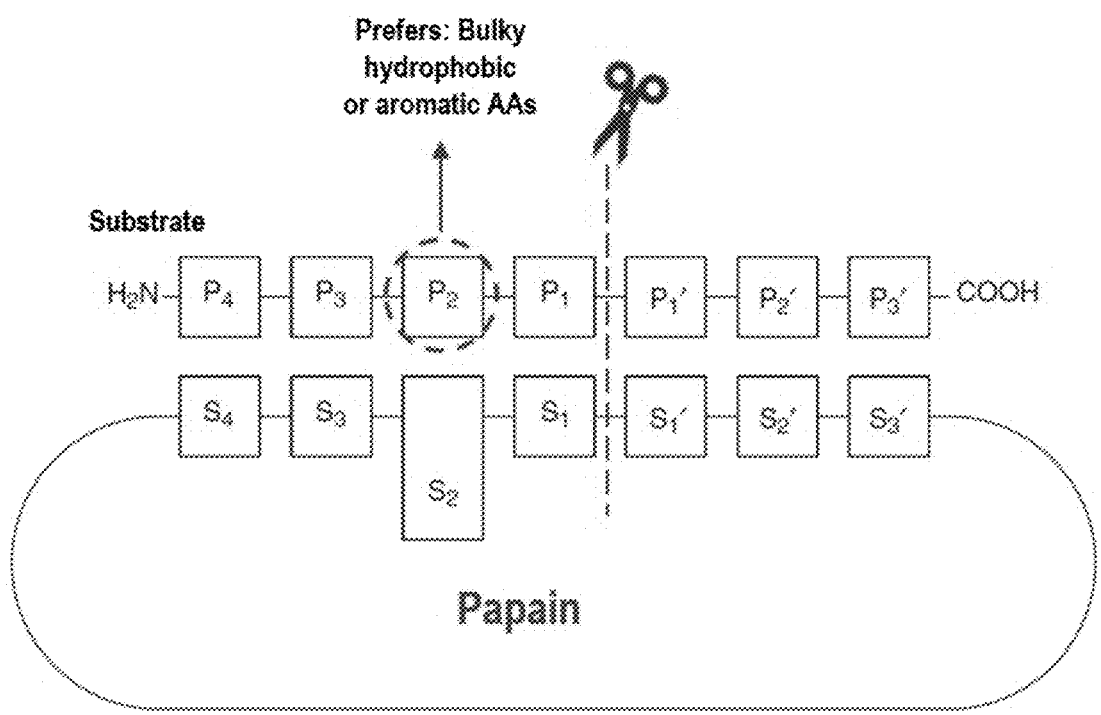
FIG. 12A shows that papain is a protease preferentially cleaving a site close to bulky hydrophobic or aromatic amino acids.
FIG. 12B shows the amino acid sequence of a tryptic peptide originally located in the hinge region of the antibody. This tryptic hinge region peptide (THTCPPCPA-PELLGGPSVFLFPPKPK (SEQ ID NO.: 1)) contains multiple papain cleavage sites. The papain cleavage sites are indicated as arrow signs.

MAB1-LK1 ADCs were digested by trypsin and subsequently by papain to obtain peptides for LC-MS analysis. Papain was used to remove payload through the recognition of valine-alanine dipeptide in LK1. As shown in FIG. 9B, a papain cleavage site is located between valine-alanine dipeptide and PABA in LK1 linker. Papain is a protease which preferentially cleaves a site close to bulky hydrophobic or aromatic amino acids as shown in FIG. 12A. Therefore, papain can also digest tryptic peptides into smaller fragments. When an antibody is digested by trypsin to generate tryptic peptides, a tryptic peptide originally located in the hinge region of the antibody is generated having the amino acid sequence of THTCPPCPAPELLGGPSVFLFPPKPK (SEQ ID NO.: 1). This tryptic hinge region peptide contains two cysteine residues (C) which are conjugation sites for attaching linker-payload through maleimide attachment group. This tryptic hinge region peptide also contains multiple papain cleavage sites as shown in FIG. 12B. The papain cleavage sites are indicated as arrow signs in FIG. 12B.

Figure 13A:
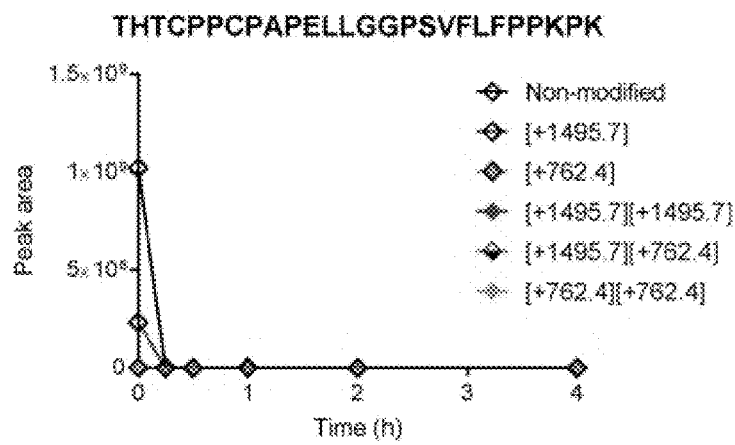
FIG. 13A-13C show the analysis results of the tryptic hinge region peptide which was digested with papain according to an exemplary embodiment.
Figure 13B:
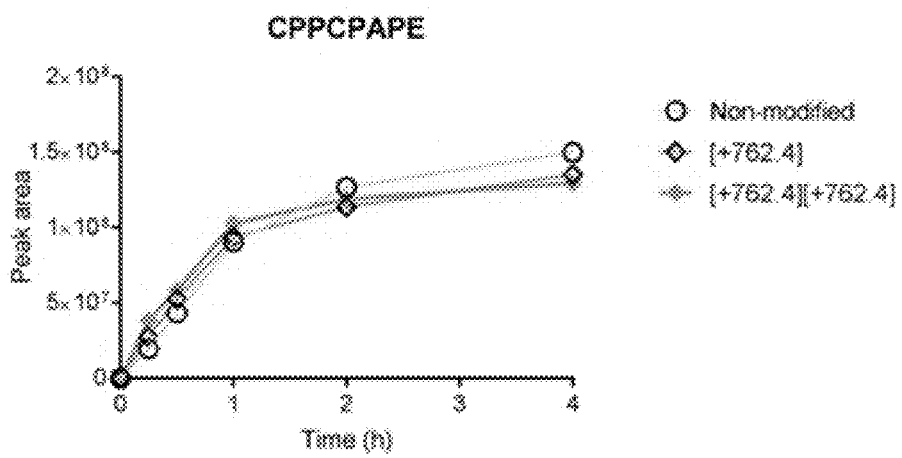
Figure 13C:
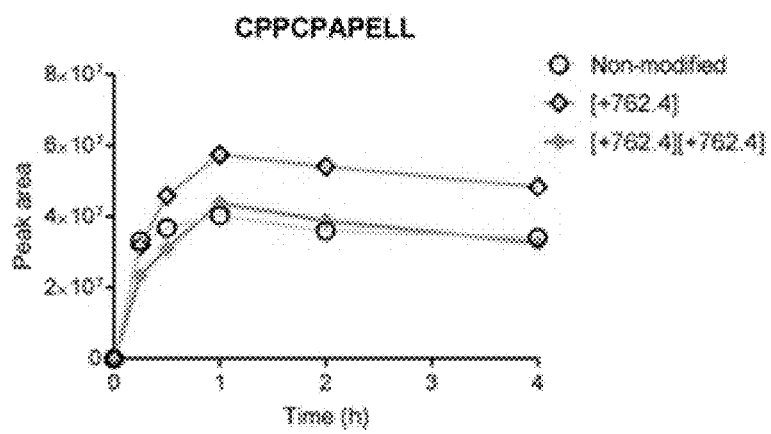

MAB1-LK1 ADCs were digested with trypsin to obtain a tryptic peptide mixture. Subsequently, the tryptic peptide mixture was digested using activated papain. The tryptic hinge region peptide which was digested with papain was analyzed using LC-MS as shown in FIG. 13A-13C. The peptide contains LK1 is designated as the mass of +1495.7 (including payload) in FIG. 13A. The peptide contains cleaved LK1 is designated as mass of +762.4 in FIG. 13A-13C. FIG. 13A-13C shows the analysis results of the tryptic hinge region peptide (FIG. 13A, amino acid sequence of THTCPPCPAPELLGGPSVFLFPPKPK (SEQ ID NO.: 1)), the peptide with amino acid sequence of CPPCPAPE (SEQ ID NO.: 2) (FIG. 13B, tryptic hinge region peptide digested with papain) and the peptide with amino acid sequence of CPPCPAPELL (SEQ ID NO.: 3) (FIG. 13C, tryptic hinge region peptide digested with papain). These peptides may contain LK1 (designated as +1495.7, including payload) or cleaved LK1 (designated as +762.4).

Example 4. Attaching Modified Linkers to Unconjugated Cysteine Residues

Figure 14:
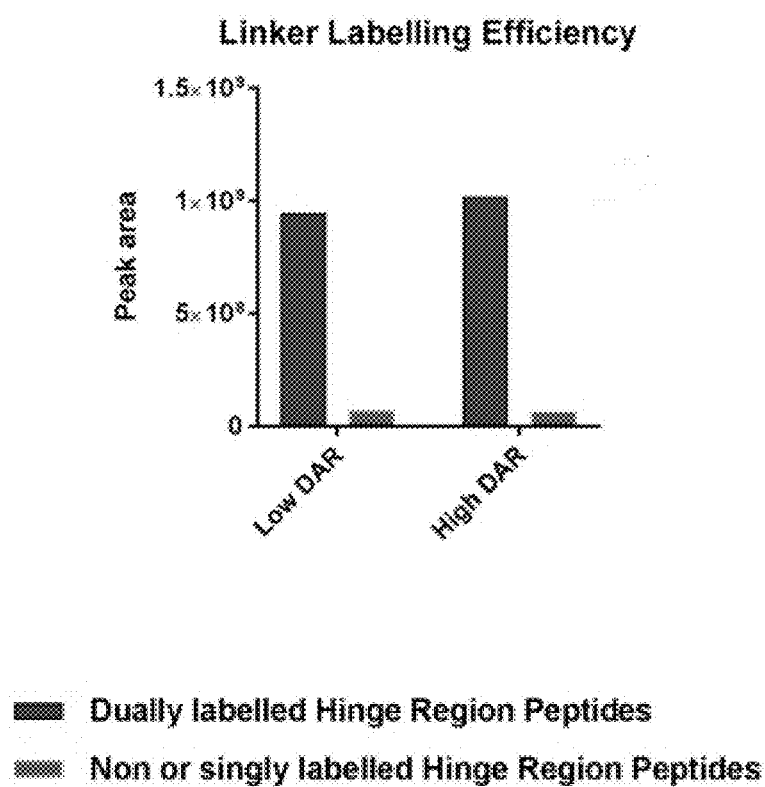
FIG. 14 shows the efficiency of linker labelling for the hinge region peptide according to an exemplary embodiment. The hinge region peptide contains two cysteine residues. The majority of the hinge region peptides have dual labels.

MAB1-LK1 ADCs with high or low DAR were digested by trypsin to generate tryptic peptide mixture. Papain was used to remove payload through the recognition of valine-alanine dipeptide in LK1. Papain can also digest tryptic peptides into smaller fragments. The tryptic peptide mixture was digested by papain, and subsequently a modified linker was used to label the papainic tryptic peptides. The modified linker containing PEG8-COOH (shown in FIG. 8C) was incubated with the peptides in 2 mM TCEP (tris(2-carboxyethyl)phosphine) at room temperature for about 2 hr with peptide to linker molar ratio of 1:500. The modified linkers were attached to unconjugated cysteine residues through maleimide attachment group to increase the mass of the peptides. Therefore, the mass of the peptide containing unconjugated cysteine is compensated for the mass difference in comparing to the conjugated peptide containing cleaved LK1. FIG. 14 shows the efficiency of linker labelling for the hinge region peptide. The hinge region peptide contains two cysteine residues. As shown in FIG. 14, the majority of the hinge region peptides have dual labels, it indicates the completion in attaching the modified linker, LK2, to unconjugated cysteine residues. Due to the completion of linker attachment, it enables the calculation of site-specific drug conjugation based on the quantitation of the labels of cleaved LK1 and LK2, e.g., site-specific drug conjugation=(cleaved LK1 labelled)/(LK2 labelled+cleaved LK1 labelled).

Example 5. Glu-C Digestion Prior to LC-MS Analysis

Figure 15:
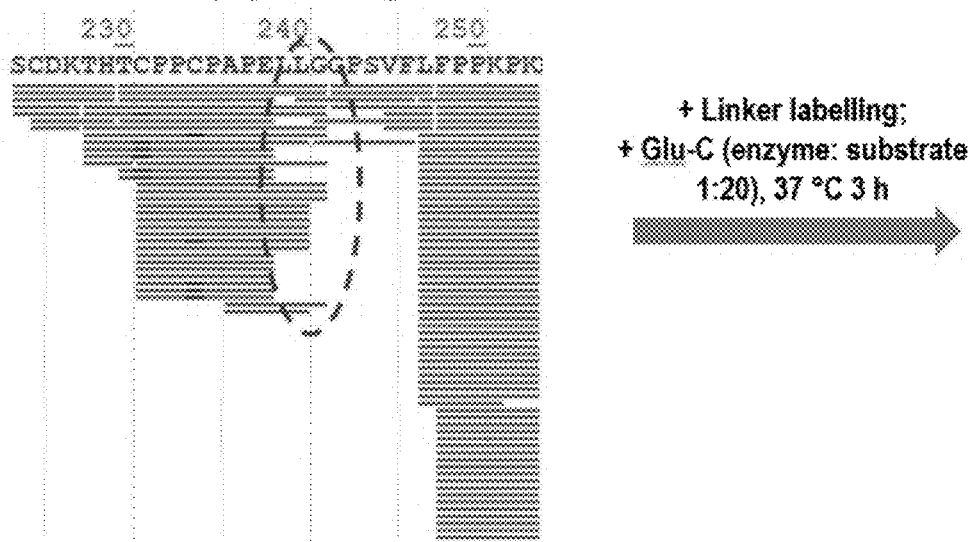
FIG. 15 shows the analysis results of Glu-C digestion of the sample prior to subjecting to LC-MS according to an exemplary embodiment. The profile of hinge region peptides was significantly reduced, which significantly simplified the quantitation using LC-MS. Figure discloses SEQ ID NOS 16 and 16, respectively, in order of appearance.
Figure 15:
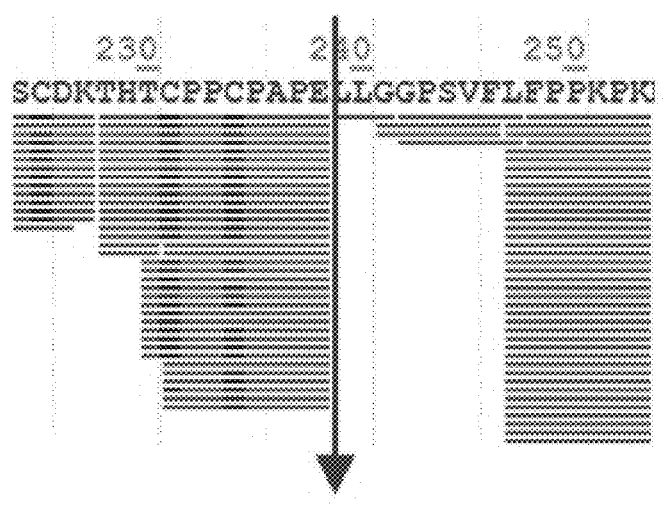

MAB1-LK1 ADCs were digested by trypsin to generate tryptic peptide mixture. Papain was used to remove payload through the recognition of valine-alanine dipeptide in LK1. Papain can also digest tryptic peptides into smaller fragments. The tryptic peptide mixture was digested by papain (about 30 minutes), and subsequently a modified linker, e.g., LK2, was used to label the unconjugated conjugation sites in the papainic tryptic peptides. After the LK2 labelling prior to conducting LC-MS analysis, the peptide mixture was digested with Glu-C. More than 9 hinge region peptides were obtained after papain digestion. Due to the use of Glu-C, the profile of hinge region peptides was reduced to three peptides (amino acid sequences of THTCPPCPAPE, (SEQ ID NO.: 6), TCPPCPAPE, (SEQ ID NO.: 5) and CPPCPAPE (SEQ ID NO.: 4)) which significantly simplified the quantitation using LC-MS as shown in FIG. 15. For Glu-C digestion, the enzyme to substrate ratio is 1:20 at 37° C. for about 3 hr.

Example 6. Site-Specific Quantitation of Drug Conjugations of MAB1-LK1 ADC

Figure 16:
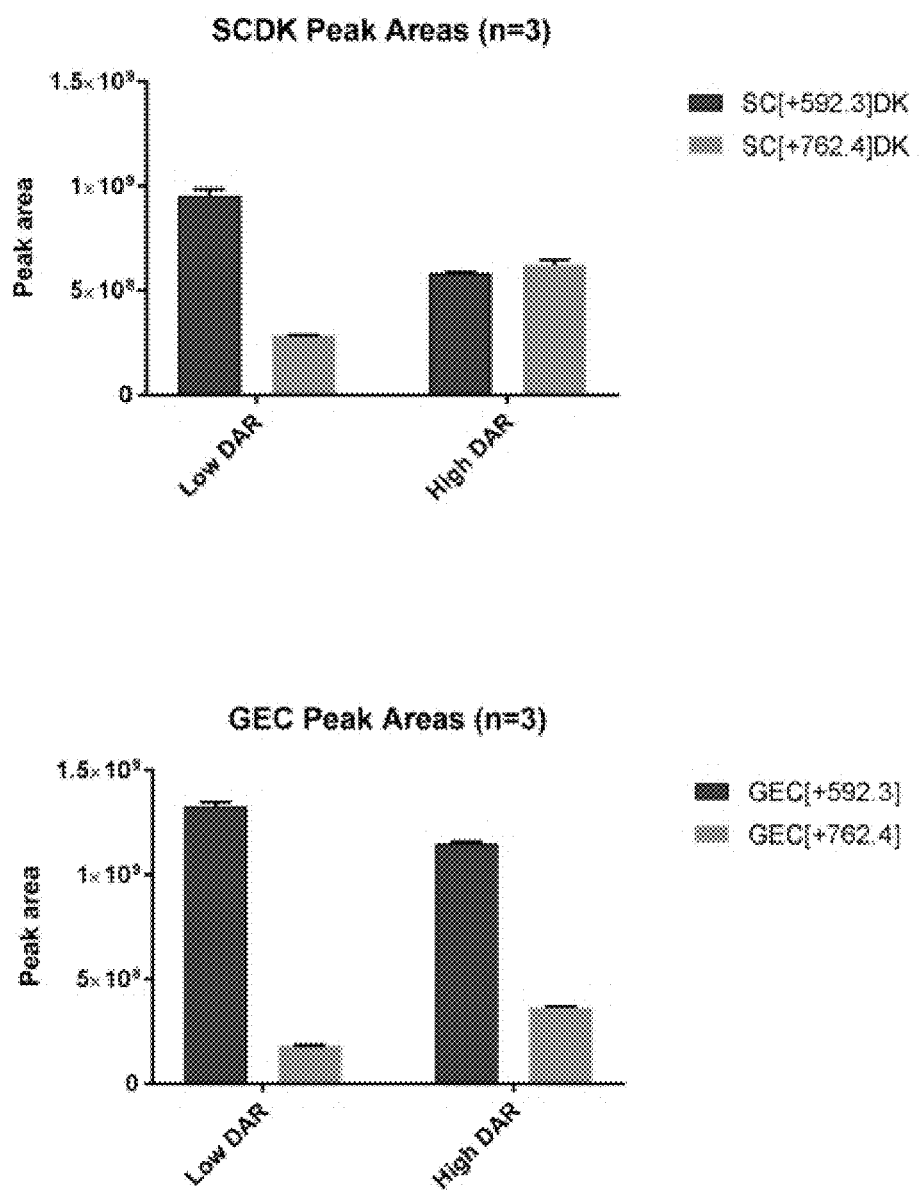
FIG. 16 shows the site-specific quantitation of drug conjugation of MAB1-LK1 ADCs according to an exemplary embodiment. The peak area of two peptides, e.g., the peptides with amino acid sequences of SCDK (SEQ ID NO: 7) or GEC, were shown. These peptides may contain cleaved LK1 (designated as +762.4) and/or LK2 (designated as +592.3).

Two MAB1-LK1 ADC samples, e.g., one with low DAR and the other one with high DAR, were analyzed by the method of the present application as shown in FIG. 6A, wherein the step of removing payload using papain was performed prior to conducting the step of adding the modified linker to unconjugated conjugation site. Two MAB1-LK1 ADC samples were digested by trypsin to generate tryptic peptide mixture and subsequently digested by papain to remove payload through the recognition of valine-alanine dipeptide in LK1. Then, a modified linker, e.g., LK2, was used to label the unconjugated conjugation sites in the papainic tryptic peptides. After the LK2 labelling, the peptides were digested by Glu-C, followed by LC-MS analysis. The MAB1-LK1 ADC sample with low DAR, e.g., MAB1-LK1-L19, has estimated DAR of 1.9 (intact, ESI). The MAB1-LK1 ADC sample with high DAR, e.g., MAB1-LK1-L8, has estimated DAR of 3.6 (intact, ESI). Each of the MAB1-LK1 ADC sample has triplicate preparations (n=3). FIG. 16 shows the site-specific quantitation of drug conjugation of MAB1-LK1 ADCs. The peak area of two peptides, e.g., the peptides with amino acid sequences of SCDK (SEQ ID NO: 7) or GEC, were shown. These peptides may contain cleaved LK1 (designated as +762.4) and/or LK2 (designated as +592.3). The peak area of the peptide containing LK2 (+592.3) indicates the quantitation of the conjugation site which was originally unconjugated. The peak area of the peptide containing cleaved LK1 (+762.4) indicates the quantitation of the conjugation site which was originally conjugated with one drug payload. In addition, the method of the present application, e.g., the method of FIG. 6A, showed good intra-day precision as shown in FIG. 17, since the calculated DAR values according to the method of the present application were comparable to intact mass method. FIG. 17 shows the analysis results of GEC peptide, SCDK (SEQ ID NO: 7) peptide, and hinge region peptides.

Example 7. Label with Modified Linker Prior to Removing the Payload

Two methods were compared side by side, e.g., the methods shown in FIGS. 6A and 6B. One method as shown in FIG. 6A was conducted to analyze MAB1-LK1 ADC samples, wherein the step of removing the payload using papain was performed prior to the step of labeling with modified linker (LK2). The MAB1-LK1 ADC sample with high DAR was digested by trypsin to generate tryptic peptides. Subsequently, the tryptic peptides were digested by papain to remove payload through the recognition of valine-alanine dipeptide in LK1. Subsequently, a modified linker, e.g., LK2, was used to label the unconjugated conjugation sites of the peptides. Then, the peptides was digested by Glu-C, followed by LC-MS analysis. The analysis results are showed in FIG. 18A.

The other method as shown in FIG. 6B was conducted to analyze MAB1-LK1 ADC samples, wherein the step of labeling with modified linker (LK2) was performed prior to the step of removing the payload using papain. The MAB1-LK1 ADC sample with high DAR was digested by trypsin to generate tryptic peptides. Subsequently, a modified linker, e.g., LK2, was used to label the unconjugated conjugation sites of the tryptic peptides. Subsequently, the peptides were digested by papain to remove payload through the recognition of valine-alanine dipeptide in LK1. Then, the peptides were digested by Glu-C, followed by LC-MS analysis. The analysis results are showed in FIG. 18B.

Figure 18A:
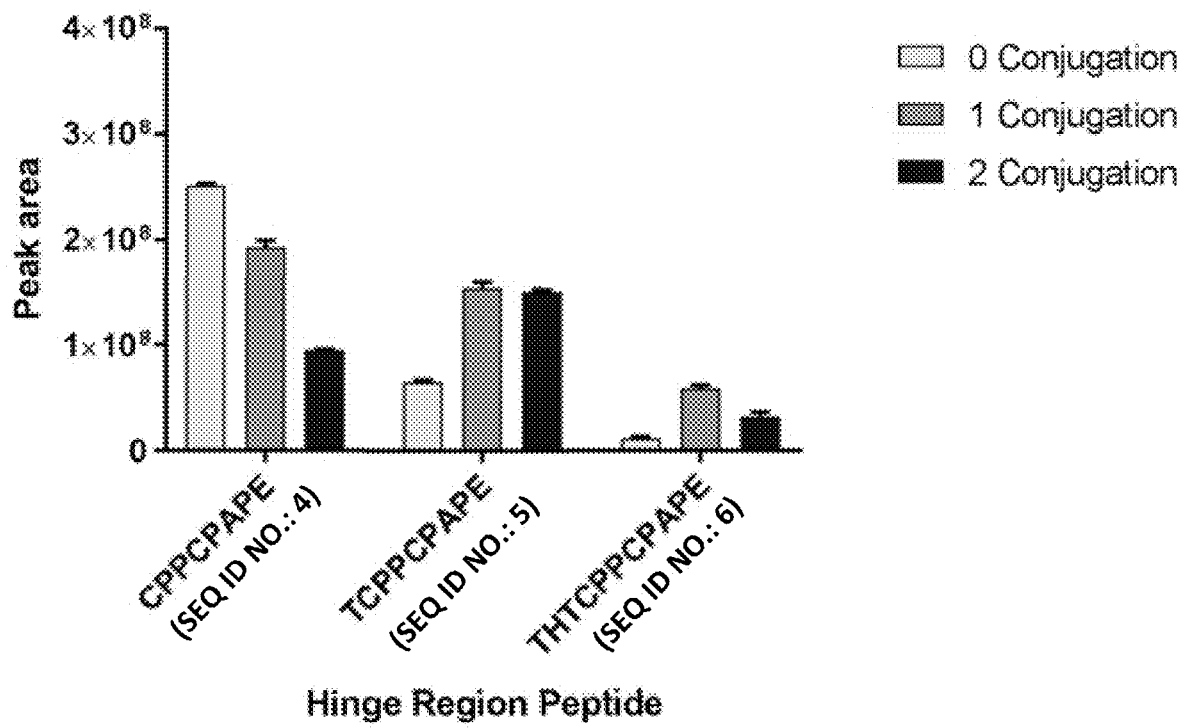
FIGS. 18A and 18B show the comparison results of two methods according to an exemplary embodiment.
Figure 18B:
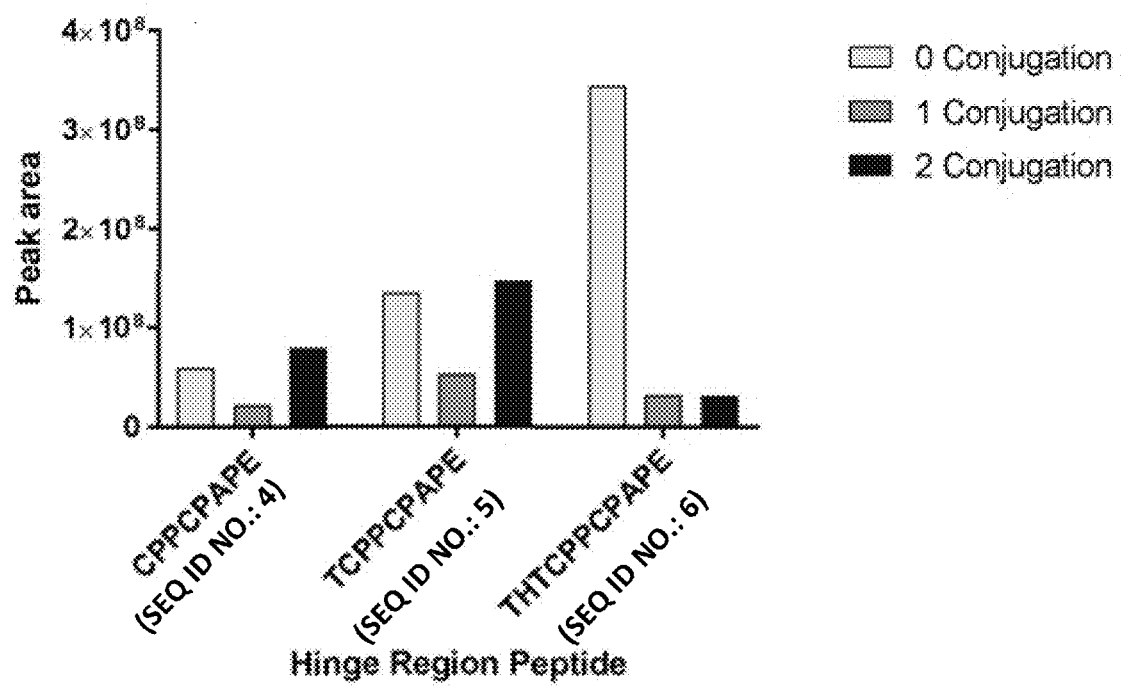

The comparison results are shown in FIGS. 18A and 18B. FIG. 18A shows the results of conducting papain digestion followed by LK2 attachment according to the method shown in FIG. 6A. FIG. 18B shows the results of conducting LK2 attachment followed by papain digestion according to the method shown in FIG. 6B. The MAB1-LK1 ADC samples with high DAR were analyzed. (+592.3, +592.3) indicates zero conjugation. (+762.4, +592.3) indicates one drug conjugation. (+762.4, +762.4) indicates two drug conjugations. The presence of conjugated drug payloads may result in preferential papain cleavage sites within the hinge region peptides. The preferential papain cleavage may cause steric hindrance effects, such as bystander effects. When the step of labeling with modified linker (LK2) was performed prior to the step of removing the payload using papain, the preferential papain cleavage was reduced.

Example 8. Papain Digestion as the Initial Step

Due to the considerations of non-specific digestion of papain of ADCs, multiple steps in various sequences were tested to minimize the non-specific digestion. Several ADCs were initially digested with papain to remove payload prior to conducting other steps, such as prior to digesting the sample with trypsin, digesting the sample with Glu-C, or conjugating modified linkers to unconjugated sulfhydryl groups (e.g., labelling).

It was found that the preferred sequence of the multiple steps was initially digesting ADC sample with papain to remove payloads, followed by reduction and denaturation, subsequently digesting the sample with trypsin, subsequently digesting the tryptic peptide mixture with Glu-C, subsequently conjugating modified linkers to unconjugated sulfhydryl groups (e.g., labelling), and subsequently subjecting the peptide mixture to LC-MS analysis as shown in FIG. 6C.

Figure 19A:
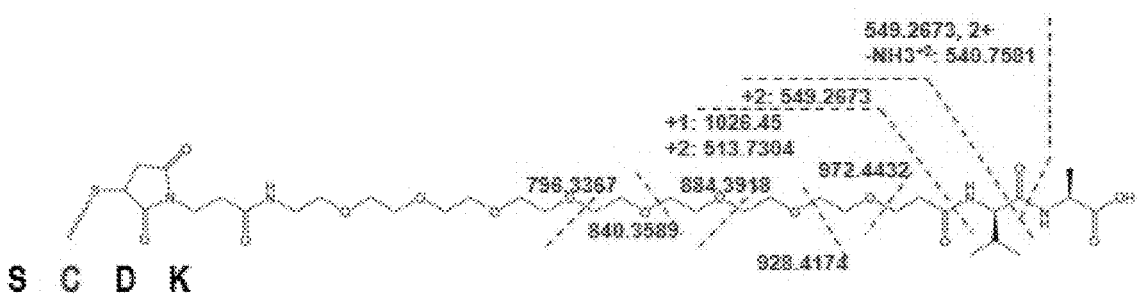
FIG. 19A shows the mass analysis of intensive fragmentation of linker dipeptide structures for tryptic peptide SCDK (SEQ ID NO: 7) containing cleaved LK1 (mal-amido-PEG8-Val-Ala) according to an exemplary embodiment.
Figure 19A:
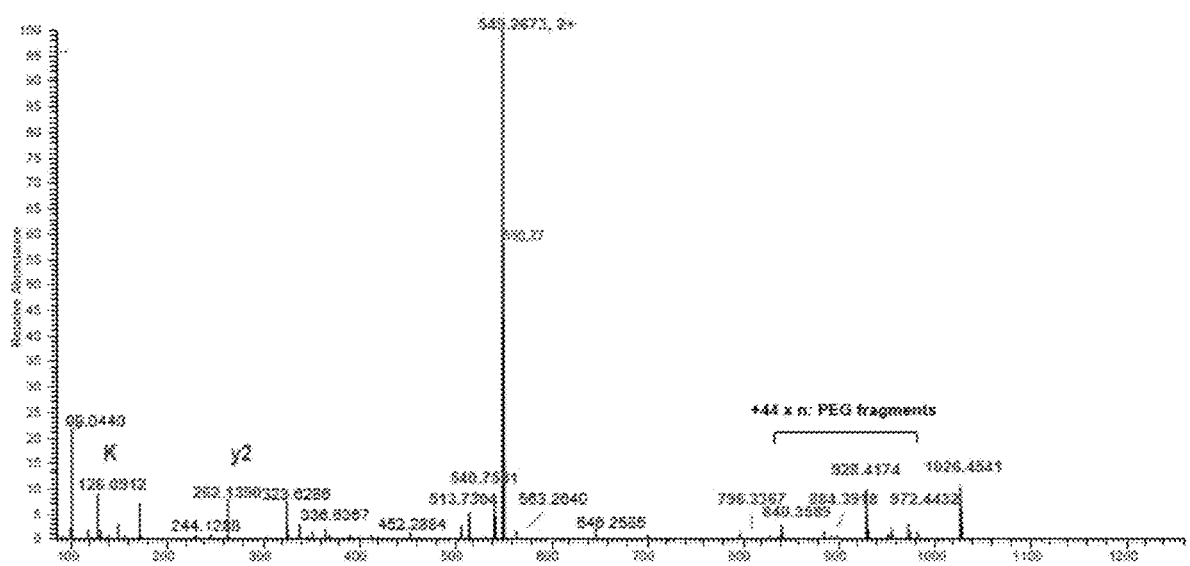
Figure 19B:
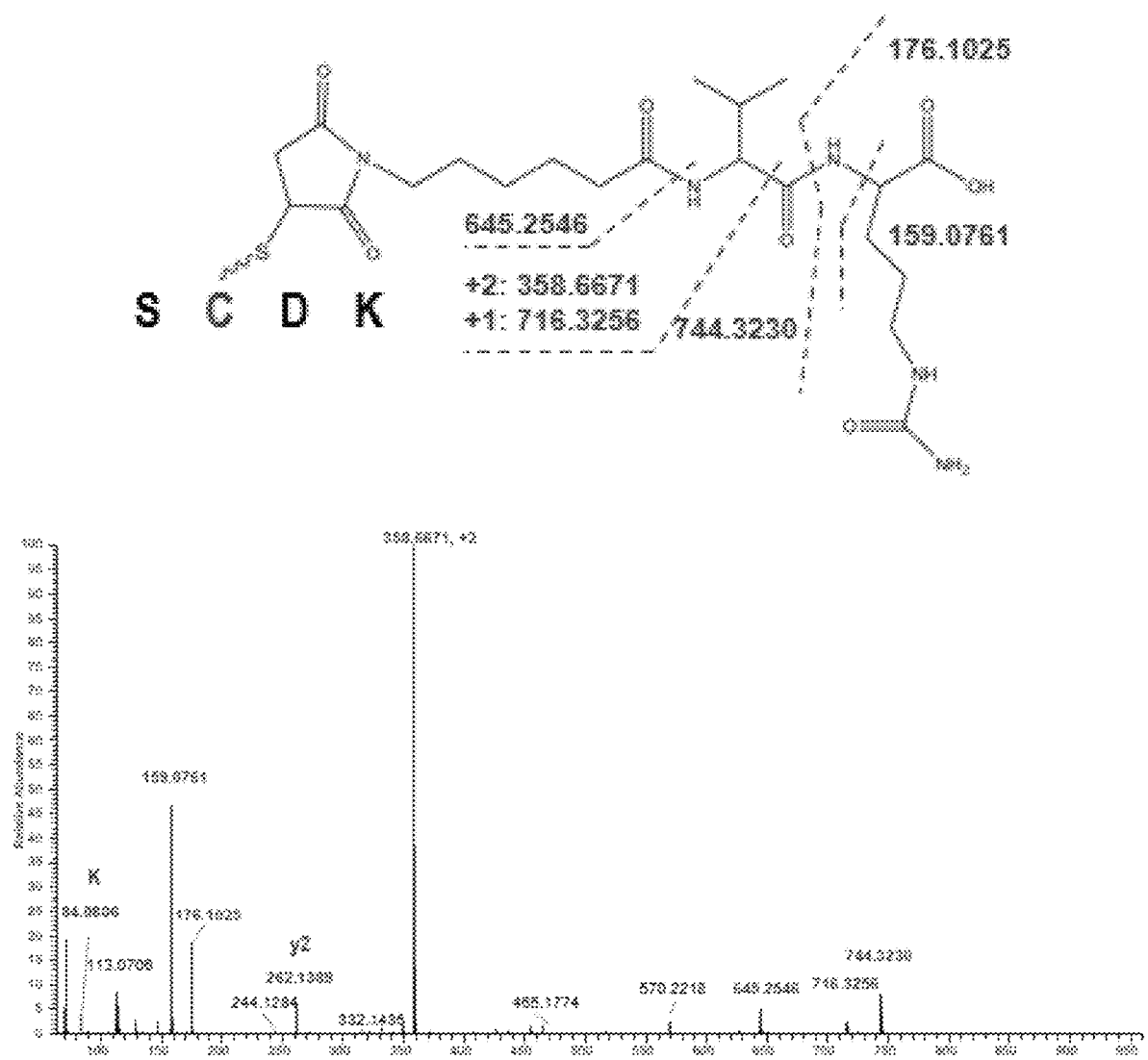
FIG. 19B shows the mass analysis of intensive fragmentation of linker dipeptide structures for tryptic peptide SCDK (SEQ ID NO: 7) containing cleaved LK3 (mal-amido-Val-Cit) according to an exemplary embodiment.

The tryptic peptides obtained from analysis of ADCs were further investigated regarding fragmentation. Some peptide identification (ID) were modified due to intensive fragmentation on linker dipeptide structures. Tryptic peptide SCDK (SEQ ID NO: 7) containing cleaved LK1 (mal-amido-PEG8-Val-Ala) or cleaved LK3 (mal-amido-Val-Cit) was analyzed for observing the intensive fragmentation which resulted small components. FIG. 19A shows the mass analysis of intensive fragmentation of linker dipeptide structures for tryptic peptide SCDK (SEQ ID NO: 7) containing cleaved LK1 (mal-amido-PEG8-Val-Ala). FIG. 19B shows the mass analysis of intensive fragmentation of linker dipeptide structures for tryptic peptide SCDK (SEQ ID NO: 7) containing cleaved LK3 (mal-amido-Val-Cit).

Figure 20A:
FIG. 20A shows the percentages of specific surrogate peptides in all peptides identified for MAB1-LK1 ADC samples according to an exemplary embodiment. 0
Figure 20A:
Figure 20A:
Figure 20A:
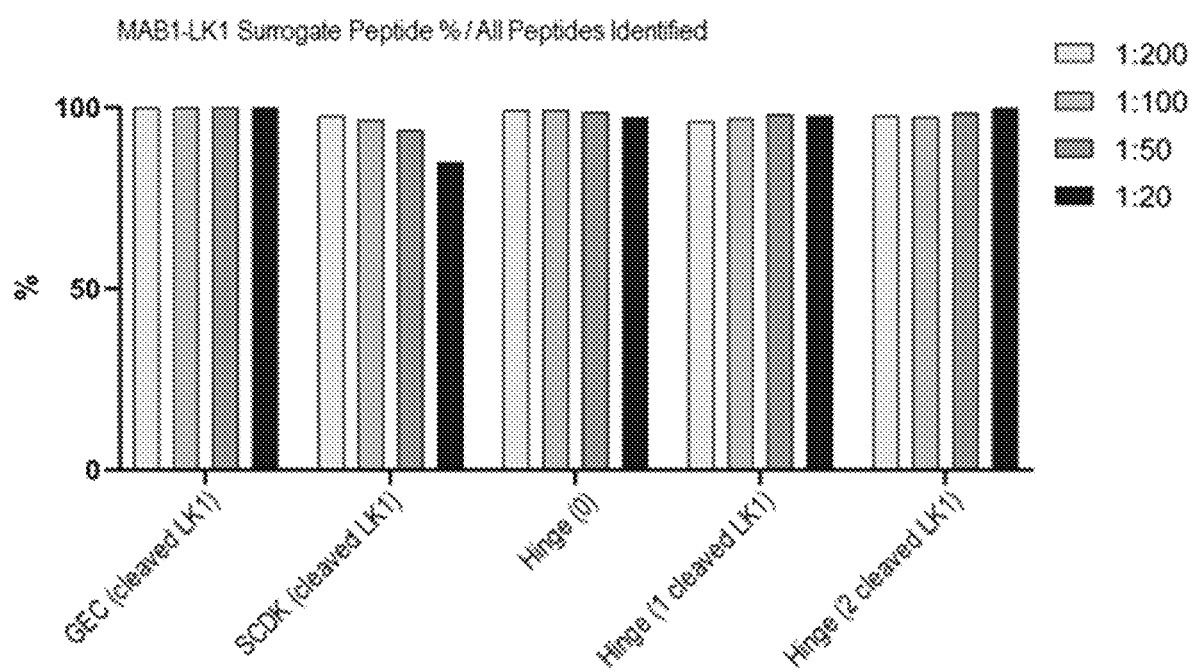
Figure 20B:
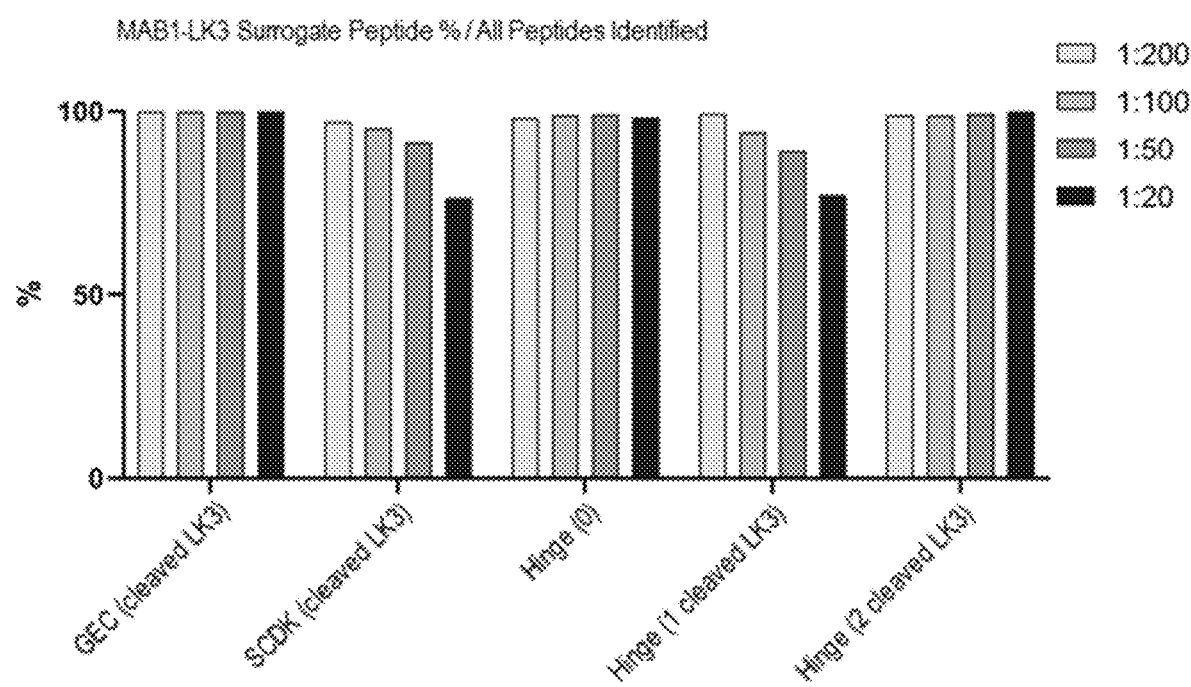
FIG. 20B shows the percentages of specific surrogate peptides in all peptides identified for MAB1-LK3 ADC samples according to an exemplary embodiment. Figure discloses SEQ ID NO: 7.

Some peptides containing conjugation sites were selected as surrogate peptides. As shown in Table 1, some peptides containing cleaved LK1 or LK3 were selected as surrogate peptides including GEC peptides, SCDK (SEQ ID NO: 7) peptides, and hinge region peptides. These surrogate peptides encompassed greater than 95% of related peptides. FIG. 20A shows the percentages of specific surrogate peptides in all peptides identified for MAB1-LK1 ADC samples. FIG. 20B shows the percentages of specific surrogate peptides in all peptides identified for MAB1-LK3 ADC samples.

TABLE 1

| Surrogate peptides | |
|---|---|
| Conjugation site | Surrogate peptides with cleaved LK1 or LK3 |
| GEC (1 drug) | GEC, SFNRGEC (SEQ ID NO: 10) |
| SCDK (SEQ ID NO: 7) (1 drug) | SCDK (SEQ ID NO: 7), SCDKTHT (SEQ ID NO: 11) |
| Hinge region (0 drug) | THTCPPCPAPE (SEQ ID NO: 6), TCPPCPAPEL (SEQ ID NO: 12), TCPPCPAPE (SEQ ID NO: 5) |
| Hinge region (1 drug) | THTCPPCPAPE (SEQ ID NO: 6), TCPPCPAPEL (SEQ ID NO: 12), TCPPCPAPE (SEQ ID NO: 5), CPPCPAPE (SEQ ID NO: 2) |
| Hinge region (2 drug) | TCPPCPAPEL (SEQ ID NO: 12), TCPPCPAPE (SEQ ID NO: 5), CPPCPAPE (SEQ ID NO: 2) |

Figure 21A:
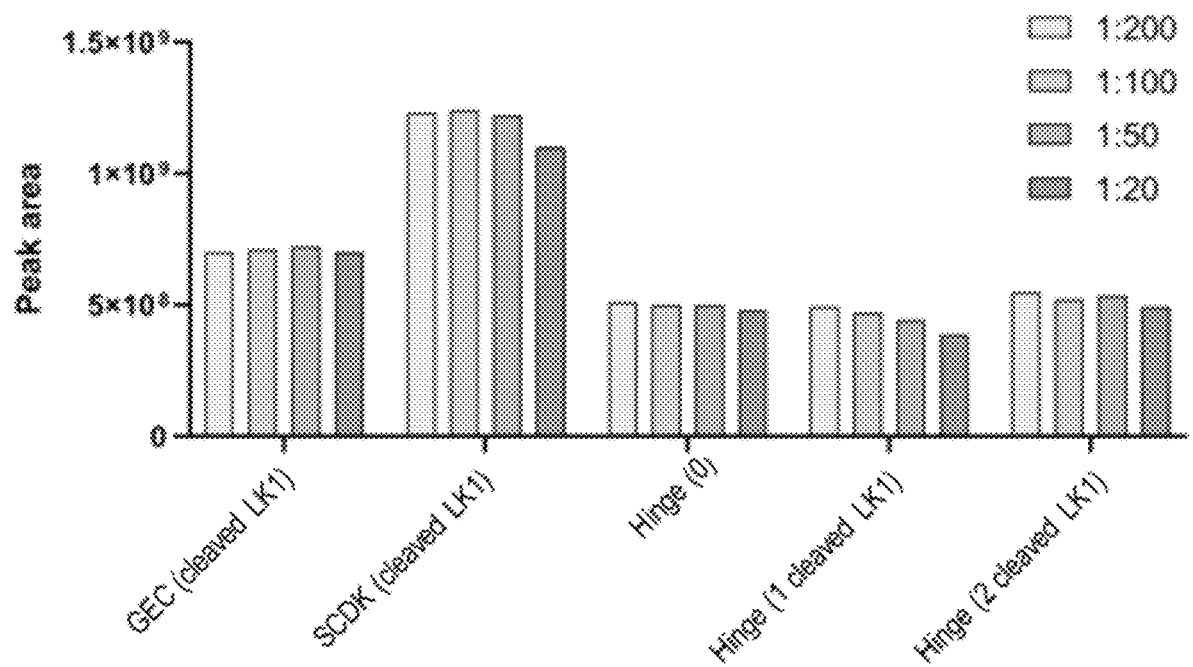
FIG. 21A shows peak areas of surrogate peptides at different papain to substrate ratios for analyzing MAB1-LK1 ADC samples according to an exemplary embodiment. Figure discloses SEQ ID NO: 7.
Figure 21:
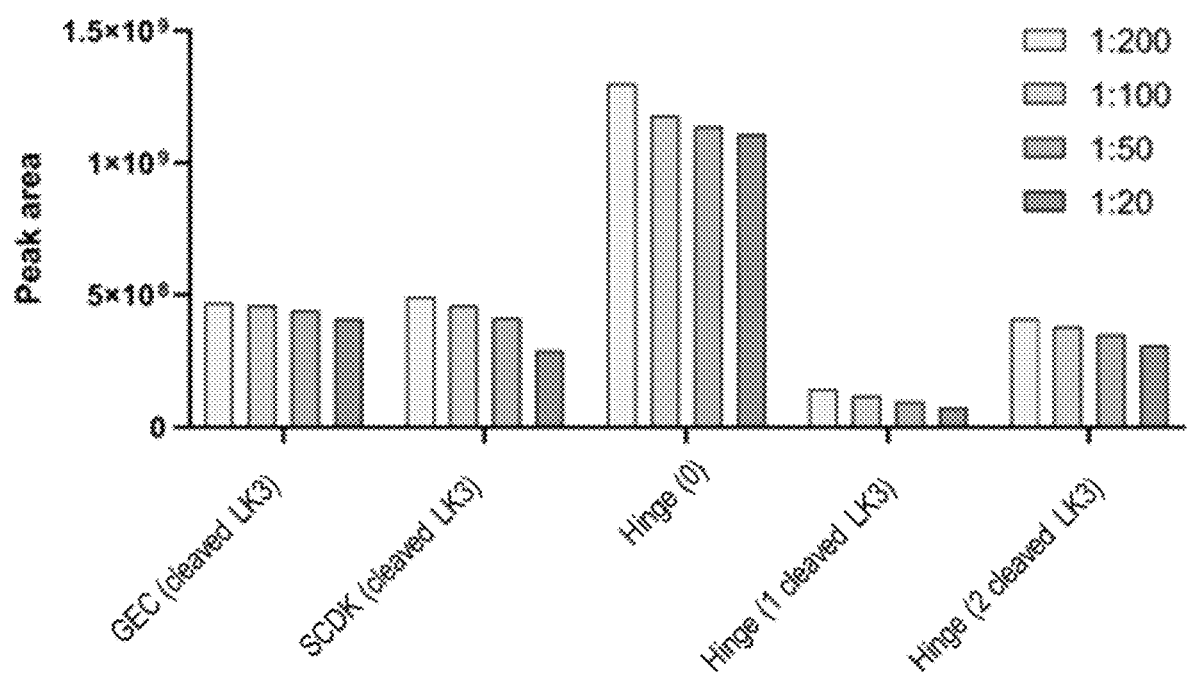
FIG. 21B shows peak areas of surrogate peptides at different papain to substrate ratios for analyzing MAB1-LK3 ADC samples according to an exemplary embodiment. Figure discloses SEQ ID NO: 7.

Papain digestion conditions were optimized by monitoring the peak areas of surrogate peptides. Different papain to substrate ratios were tested, such as 1:20, 1:50, 1:100 and 1:200 for analyzing MAB1-LK1 and MAB1-LK3 ADC samples. Total peak areas of surrogate peptides decreased at higher papain concentrations. FIG. 21A shows peak areas of surrogate peptides at different papain to substrate ratios for analyzing MAB1-LK1 ADC samples. FIG. 21B shows peak areas of surrogate peptides at different papain to substrate ratios for analyzing MAB1-LK3 ADC samples. The results indicated that the papain to substrate ratio at 1:200 was preferable for both MAB1-LK1 ADCs and MAB1-LK3 ADCs.

Figure 22:
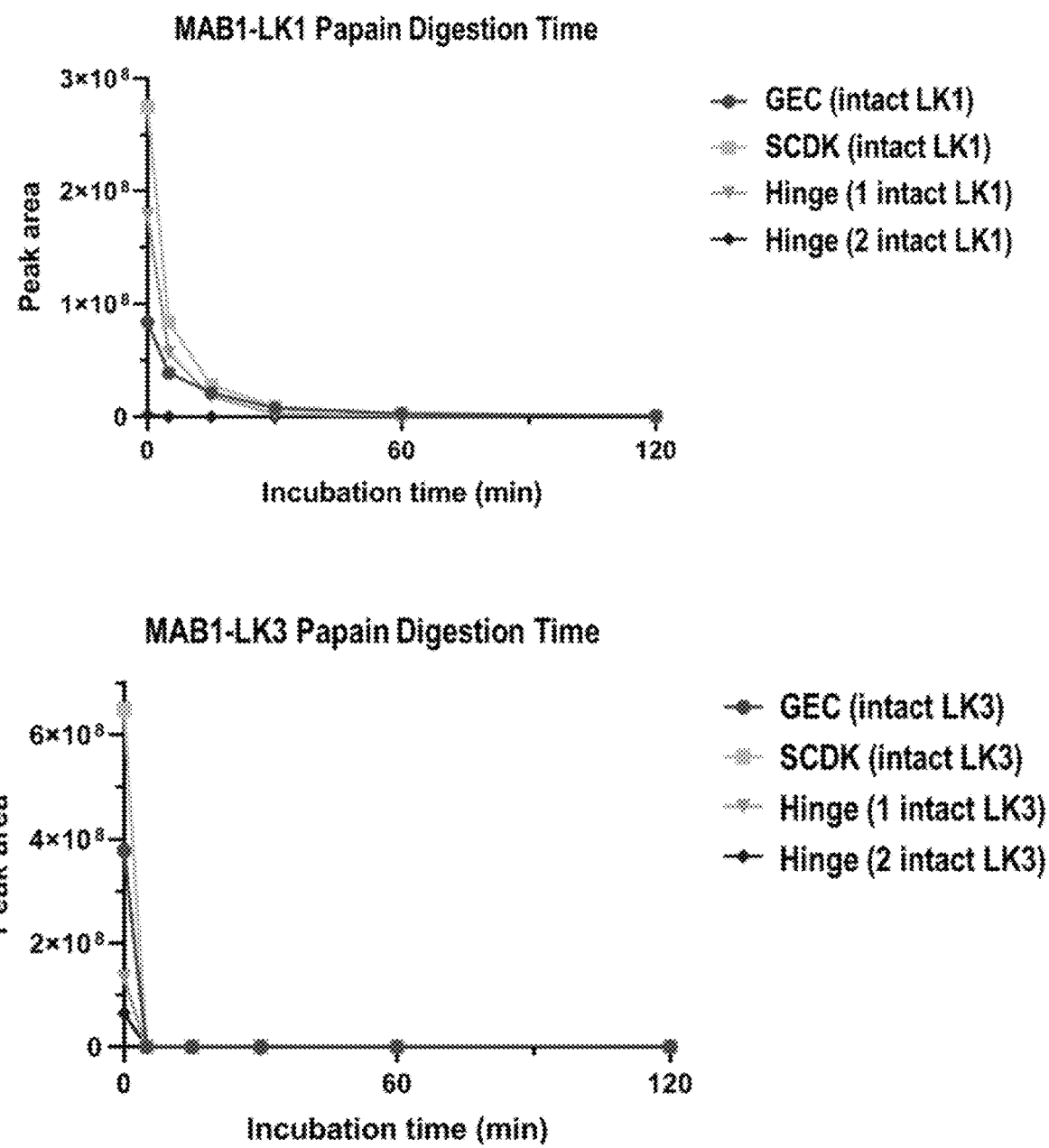
FIG. 22 shows the peak areas of surrogate peptides containing LK1 or LK3, such as GEC, SCDK (SEQ ID NO: 7), or hinge peptide containing one or two intact LK1 or LK3, at different incubation time according to an exemplary embodiment.

Papain digestion conditions were further optimized for selecting preferable digestion time period. The presence of intact linker payloads was detected at different incubation time during papain digestion by monitoring the peak areas of peptides containing intact LK1 or LK3. FIG. 22 shows the peak areas of surrogate peptides containing LK1 or LK3, such as GEC, SCDK (SEQ ID NO: 7), or hinge peptide containing one or two intact LK1 or LK3, at different incubation time. Regarding the papain digestion of MAB1-LK1, intact linker payloads of LK1 (containing Val-Ala dipeptide) were undetectable after one hour of papain digestion. Regarding the papain digestion of MAB1-LK3, intact linker payloads of LK3 (containing Val-Cit dipeptide) were undetectable after five minutes of papain digestion. The results indicated that the preferable papain digestion time was one hour. The time period for reaching completion of papain digestion to remove payloads for LK3, e.g., a substrate containing a Val-Cit dipeptide, was shorter in comparison with LK1, e.g., a substrate containing a Val-Ala dipeptide.

Figure 23:
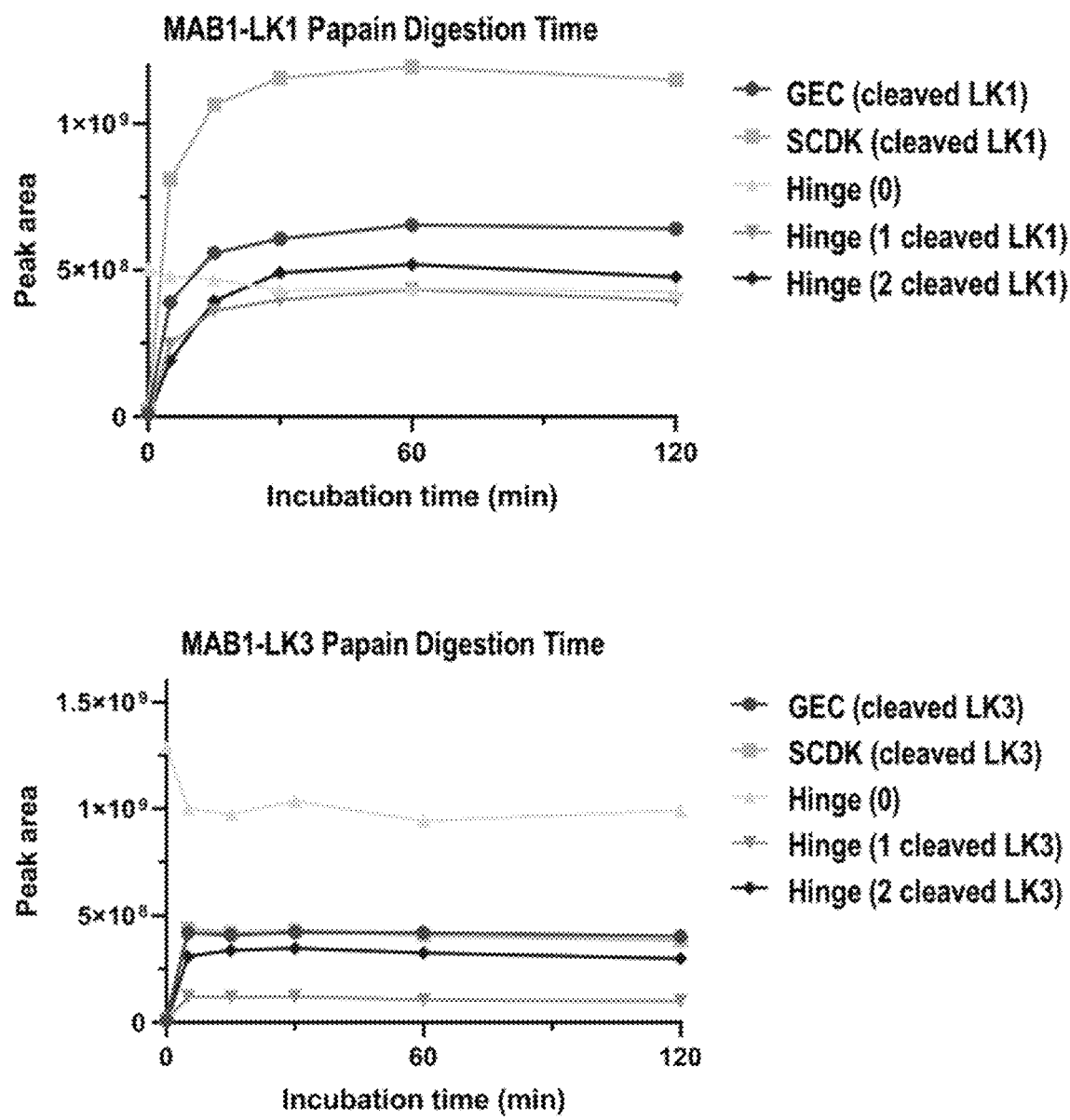
FIG. 23 shows the peak areas of surrogate peptides containing LK1 or LK3, such as GEC, SCDK (SEQ ID NO: 7), or hinge peptide containing one or two cleaved LK1 or LK3, at different incubation time according to an exemplary embodiment. The peak areas of hinge peptides which did not contain cleaved linker were also monitored according to an exemplary embodiment.

Papain digestion conditions were further optimized for selecting preferable digestion time period by monitoring cleaved linker payload. The presence of cleaved linker payloads was detected at different incubation time during papain digestion by monitoring the peak areas of peptides containing cleaved LK1 or LK3. FIG. 23 shows the peak areas of surrogate peptides containing LK1 or LK3, such as GEC, SCDK (SEQ ID NO: 7), or hinge peptide containing one or two cleaved LK1 or LK3, at different incubation times. The peak areas of hinge peptides which did not contain cleaved linker were also monitored. The completion of papain digestion to remove drug payloads for both LK1 and LK3 were achieved within one hour incubation. The results indicated that the preferable papain digestion time was one hour under the condition of papain to substrate ratio at 1:200.

Figure 24A:
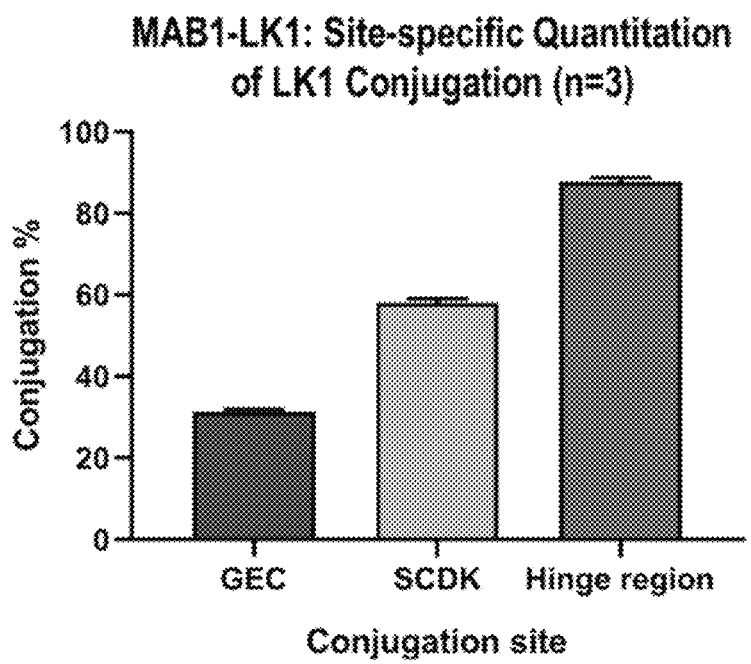
FIG. 24A shows the site-specific quantitation of LK1 conjugation for MAB1-LK1 ADC by analyzing the conjugation sites at GEC, SCDK (SEQ ID NO: 7) and hinge region peptides according to an exemplary embodiment.
Figure 24B:
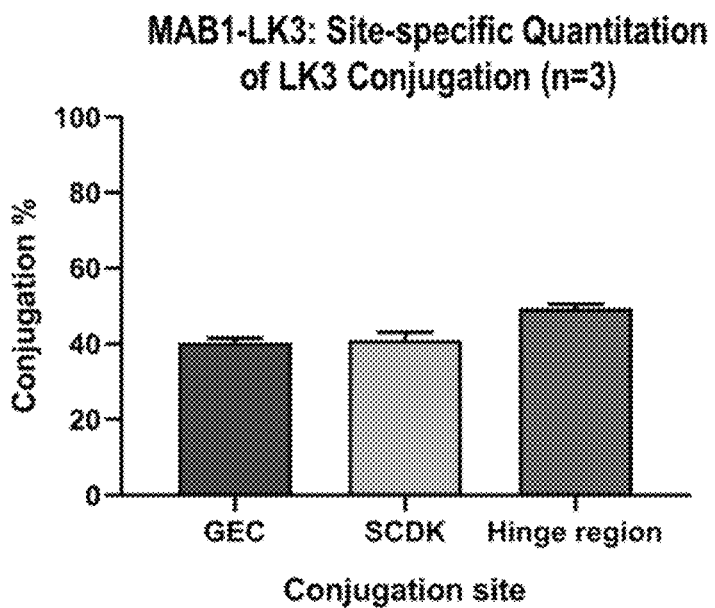
FIG. 24B shows the site-specific quantitation of LK3 conjugation for MAB1-LK3 ADC by analyzing the conjugation sites at GEC, SCDK (SEQ ID NO: 7) and hinge region peptides according to an exemplary embodiment.

Site-specific quantitation of LK1 conjugation for MAB1-LK1 ADC was estimated by analyzing the conjugation sites at GEC, SCDK (SEQ ID NO: 7) and hinge region peptides as shown in FIG. 24A. Site-specific quantitation of LK3 conjugation for MAB1-LK3 ADC was estimated by analyzing the conjugation sites at GEC, SCDK (SEQ ID NO: 7) and hinge region peptides as shown in FIG. 24B. The conjugation percentage was estimated based on percentage of conjugated drugs located on specific peptide. For example, conjugation percentage of hinge region can be estimated based on the formulation of:

Conjugation percentage(hinge region)=0×(percentage of 0 drug)+1×(percentage of 1 drug)+2×(percentage of 2 drug)

In addition, the method of the present application, e.g., the method of FIG. 6C, showed good intra-day and inter-day precision, since the calculated DAR values according to the method of the present application were comparable to intact mass method. FIG. 25 shows intra-day and inter-day precision of the method of the present application regarding the analysis results of DAR of GEC peptide, SCDK (SEQ ID NO: 7) peptide, and hinge region peptides. Good intra-day and inter-day precision was demonstrated in the site-specific quantitation of linker-drug conjugation for analyzing MAB1-LK1 ADCs and MAB1-LK3 ADCs, since the calculated total DAR values were comparable to intact mass method. DAR values were calculated based on the formulation of:

DAR=[conjugation ratio(hinge region)+conjugation ratio(GEC)+conjugation ratio(SCDK(SEQ ID NO: 7))]×2.

Figure 26:
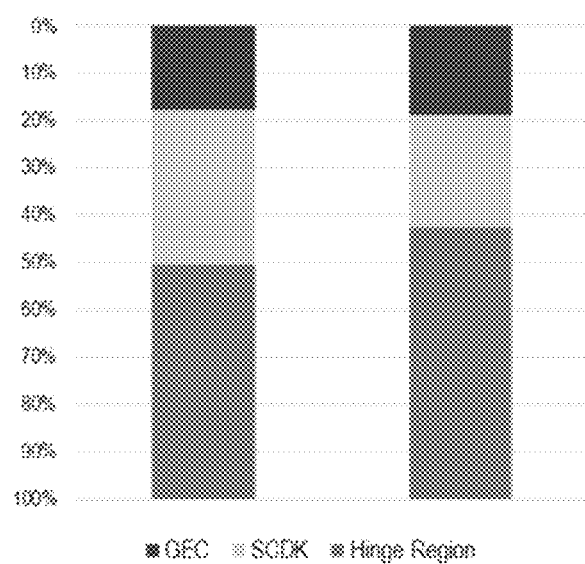
FIG. 26 shows lot-to-lot variation in drug conjugation distribution for MAB1-LK1-L8 and MAB1-LK1-L22 by analyzing conjugation sites on GEC, SCDK (SEQ ID NO: 7) and hinge region peptides according to an exemplary embodiment.

MAB1-LK1 ADCs were tested regarding lot-to-lot variation and conjugation stability on different conjugation sites as shown in Table 2. Two different lots of MAB1-LK1 ADCs, e.g., MAB1-LK1-L8 and MAB1-LK1-L22 were tested to observe the distribution of drug conjugation. The DAR value of MAB1-LK1-L8 was 3.6. The DAR value of MAB1-LK1-L22 was 3.65. FIG. 26 shows lot-to-lot variation in drug conjugation distribution for MAB1-LK1-L8 and MAB1-LK1-L22 by analyzing conjugation sites on GEC, SCDK (SEQ ID NO: 7) and hinge region peptides.

TABLE 2

Lot-to-lot variation and conjugation stability

| Samples | Lot | Stressed Conditions | Concentration (mg/ml) | Volume (μL) | Buffer |
|---|---|---|---|---|---|
| 1 | MAB1-LK1-L8 (ESI: DAR 3.6) | / | 5 | 400 | PBS-G |
| 2 | MAB1-LK1-L22 (ESI: DAR 3.65) | / | 4 | 100 | 10 mM histidine, pH 5.5 |
| 3 | MAB1-LK1-L22 | 40° C., 28 d | 4 | 100 | 10 mM histidine, pH 5.5 |
| 4 | MAB1-LK1-L22 | 40° C., 28 d | 4 | 100 | 10 mM histidine, pH 6.0 |
| 5 | MAB1-LK1-L22 | 40° C., 28 d | 4 | 100 | 10 mM histidine, pH 6.5 |

Example 9. Conjugation Stability on SCDK (SEQ ID NO: 7) Peptide

Figure 27:
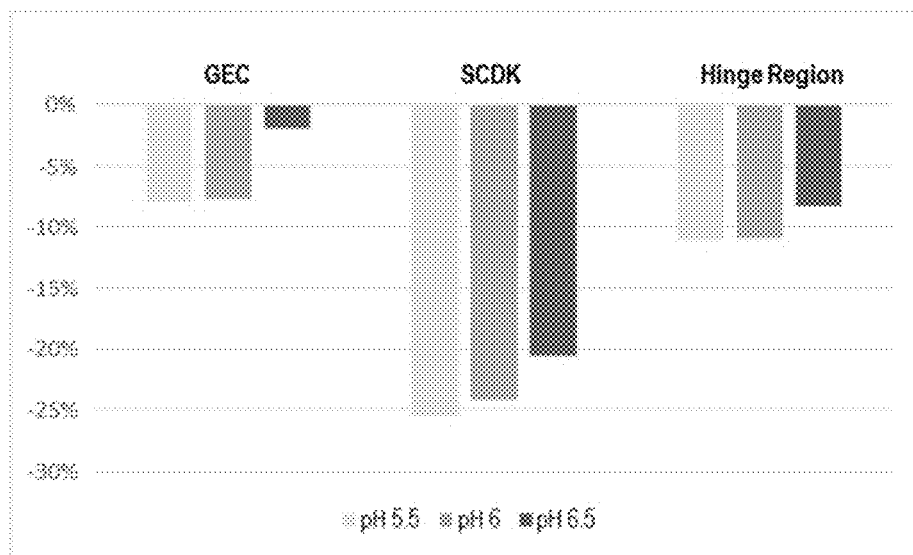
FIG. 27 shows the loss percentage of LK1 conjugation for MAB1-LK1 ADCs under thermal stress at 40° C. for 28 days by analyzing GEC, SCDK (SEQ ID NO: 7) and hinge region peptides at different pH conditions including pH 5.5, pH 6 and pH 6.5 according to an exemplary embodiment.

The conjugation stability of cysteine-linked ADCs was analyzed, since Sanderson et al. showed that an anti-CD30 cysteine linked ADC had poor conjugation stability on heavy chains of antibodies (Sanderson et al., In vivo drug-linker stability of an anti-CD30 dipeptide-linked auristatin immunoconjugate, Clin Cancer Res. 2005 Jan. 15; 11:843-852). MAB1-LK1 ADCs were analyzed under thermal stress by analyzing the loss of LK1 conjugation. FIG. 27 shows the loss percentage of LK1 conjugation for MAB1-LK1 ADCs under thermal stress at 40° C. for 28 days by analyzing GEC, SCDK (SEQ ID NO: 7) and hinge region peptides at different pH conditions, such as pH 5.5, pH 6 and pH 6.5. The results indicated that greater than 20% loss of LK1 conjugation was observed from SCDK (SEQ ID NO: 7) peptide. The loss percentage increased at lower pH conditions.

Figure 28:
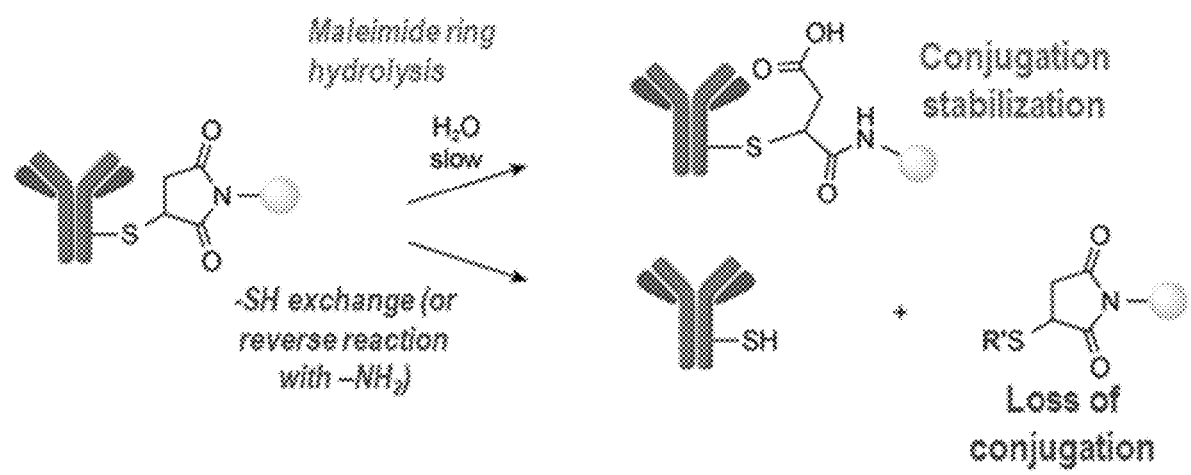
FIG. 28 shows the chemical mechanism of maleimide ring hydrolysis according to an exemplary embodiment.
Figure 29A:
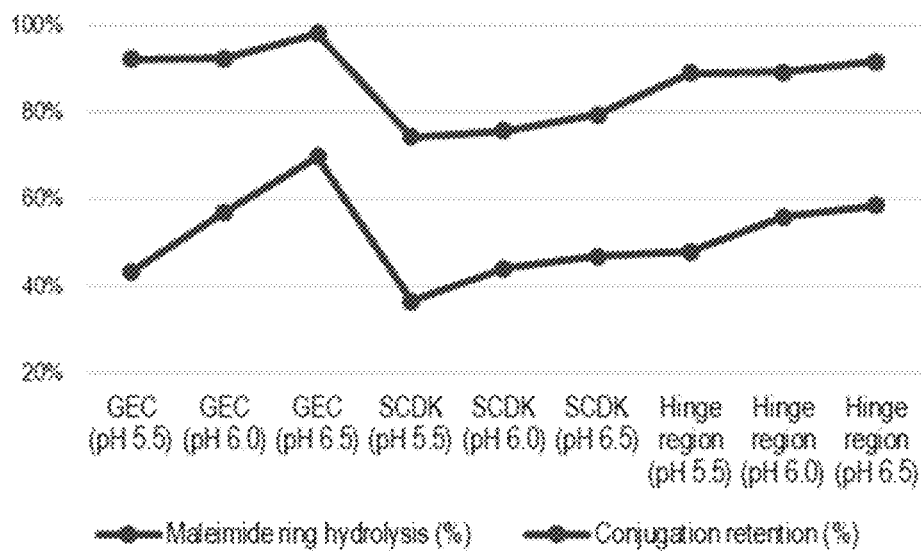
FIG. 29A shows the percentages of maleimide ring hydrolysis and conjugation retention by analyzing GEC, SCDK (SEQ ID NO: 7) and hinge peptides under different pH conditions including pH 5.5, pH 6.0 and pH 6.5 according to an exemplary embodiment.
Figure 29B:
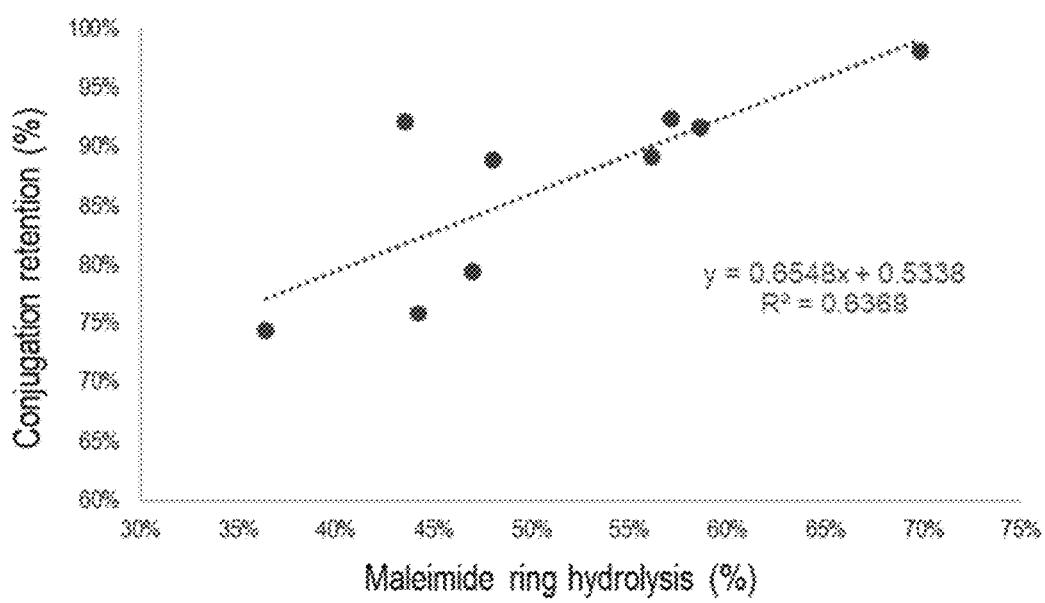
FIG. 29B shows the correlation analysis between conjugation retention and maleimide ring hydrolysis according to an exemplary embodiment.

The correlation of conjugation retention with maleimide ring hydrolysis was investigated. The chemical mechanism of maleimide ring hydrolysis is shown in FIG. 28. FIG. 29A shows the percentages of maleimide ring hydrolysis and conjugation retention by analyzing GEC, SCDK (SEQ ID NO: 7) and hinge peptides under different pH conditions including pH 5.5, pH 6.0 and pH 6.5. FIG. 29B shows the correlation analysis between conjugation retention and maleimide ring hydrolysis. The results indicated that a lower tendency of maleimide ring hydrolysis at SCDK (SEQ ID NO: 7) (C at 225 residue) of heavy chain may be attributed to inferior conjugation stability.

Example 10. Site-Specific Quantitation of Drug Conjugations of Lysine-Linked ADCs MAB2-LK5 ADCs, e.g., lysine-linked ADCs, were analyzed to quantitate site-specific drug conjugation. MAB2-LK5 ADCs were digested with papain to remove payloads, followed by reduction and denaturation, followed by alkylation, followed by digesting ADC samples with Glu-C to obtain Glu-C digested peptide mixture, digesting the peptide mixture with Asp-N, and followed by subjecting the peptide mixture to LC-MS analysis as shown in FIG. 7. The site-specific drug conjugations were estimated based on the quantitation of peptides containing cleaved linkers and native peptides which do not contain cleaved linkers, e.g., site-specific drug conjugation=(quantity of peptides containing cleaved linker)/(quantity of peptides containing cleaved linkers+quantity of native peptides).

Figure 30A:
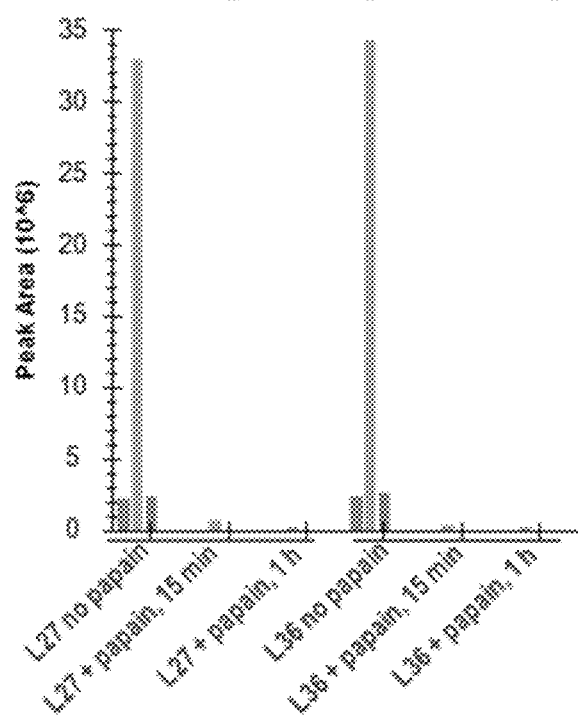
FIGS. 30A-30C show the analysis of drug conjugation on lysine 208 residue in light chain of the antibody using papain digestion according to an exemplary embodiment. Figure discloses SEQ ID NOS 17, 17, and 17, respectively, in order of appearance.
Figure 30B:
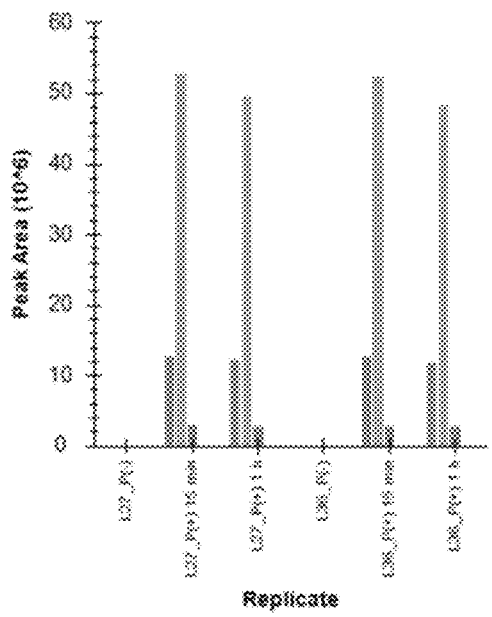
Figure 30:
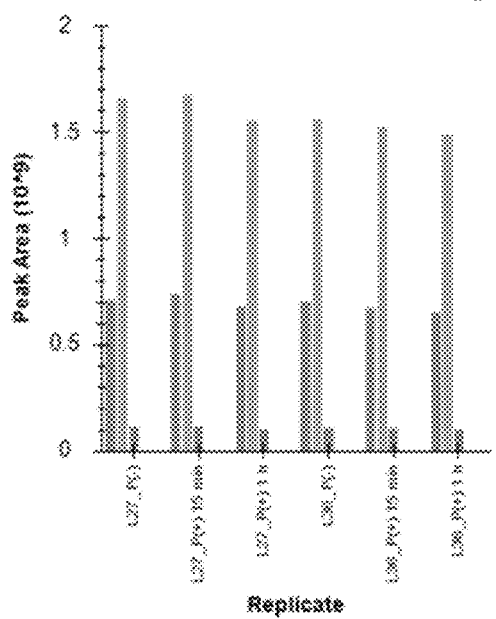
Figure 31A:
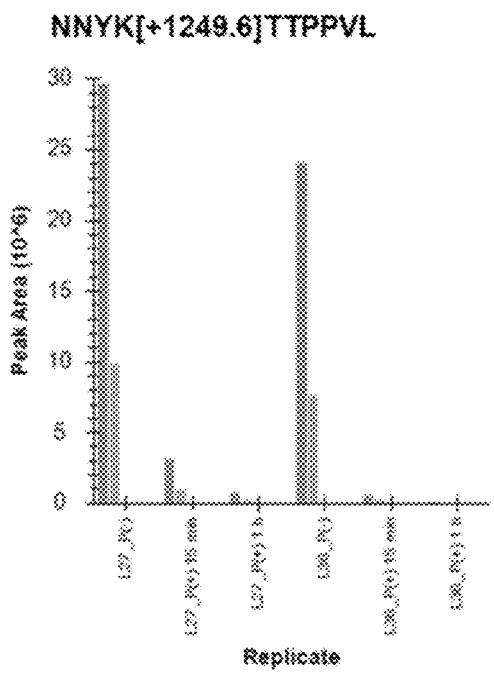
FIGS. 31A-31C show the analysis of drug conjugations on lysine 393 and lysine 389 residues in heavy chain of the antibody (HC Lys393/HC*Lys389) using papain digestion according to an exemplary embodiment. Figure discloses SEQ ID NOS 18, 18, and 18, respectively, in order of appearance.
Figure 31B:
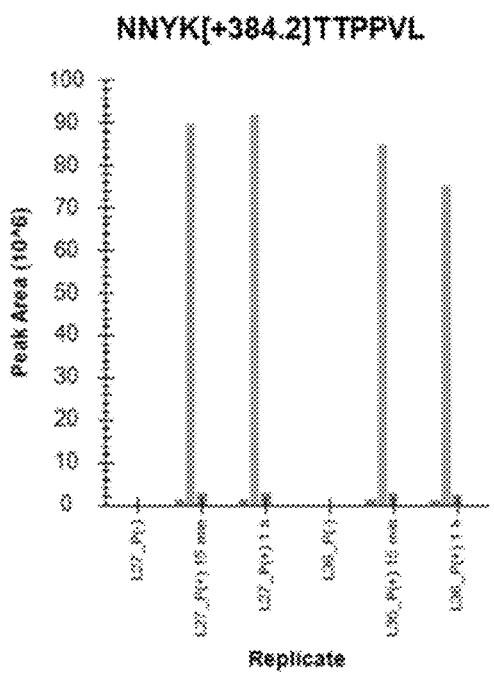
Figure 31C:
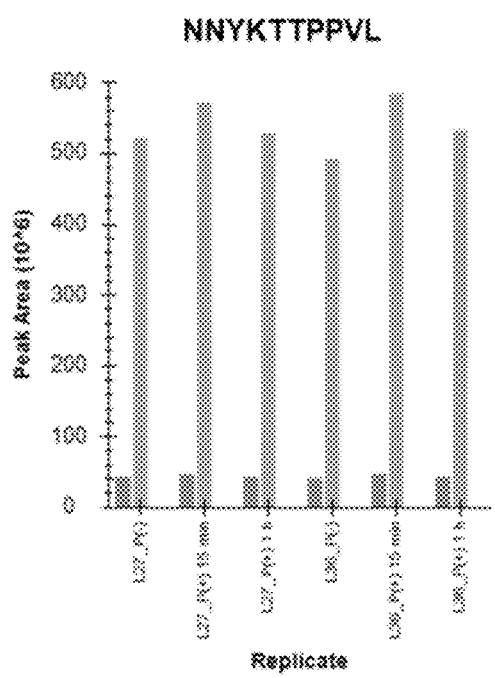
Figure 32A:
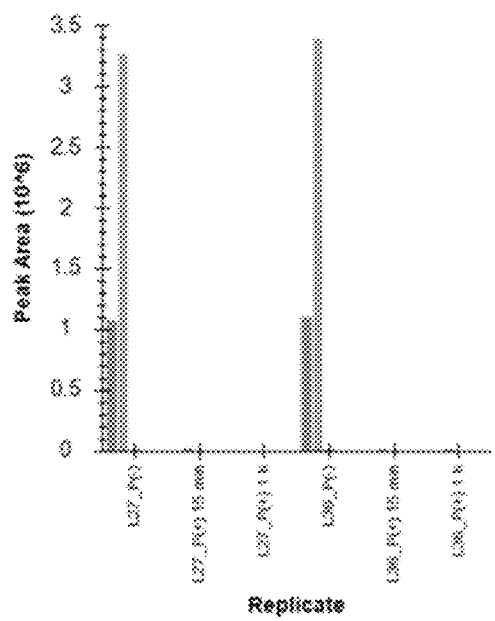
FIGS. 32A-32C show the analysis of drug conjugation on lysine 65 residue in light chain of the antibody using papain digestion according to an exemplary embodiment. Figure discloses SEQ ID NOS 19, 19, and 19, respectively, in order of appearance.
Figure 32B:
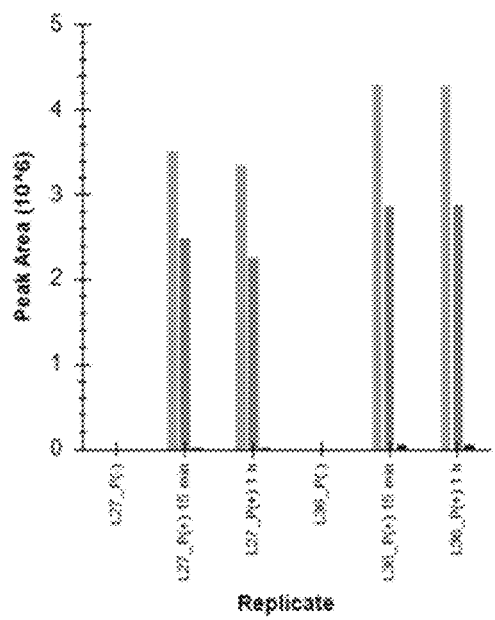
Figure 32C:
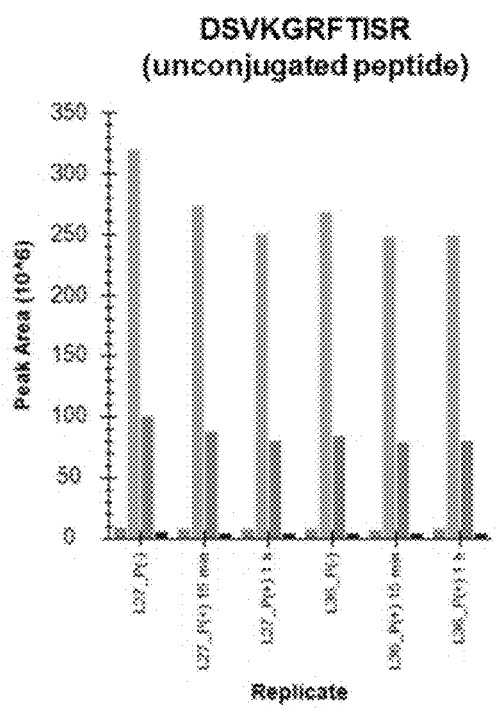
Figure 33A:
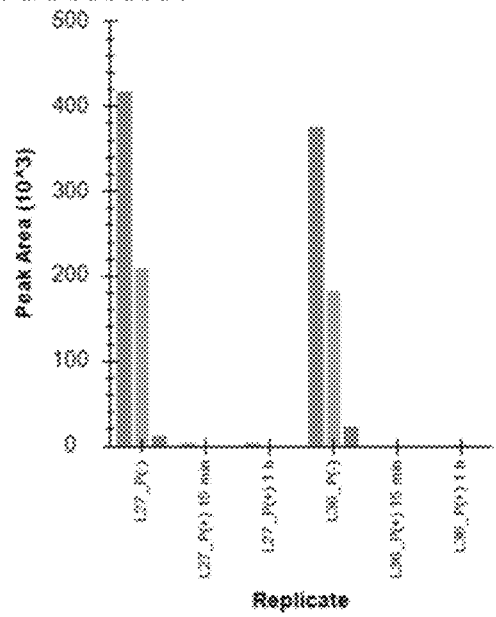
FIGS. 33A-33C show the analysis of drug conjugation on lysine 39, 42 or 45 residue in light chain of the antibody using papain digestion by analyzing a peptide containing 55 amino acids according to an exemplary embodiment. Figure discloses SEQ ID NOS 20, 20, and 20, respectively, in order of appearance.
Figure 33B:
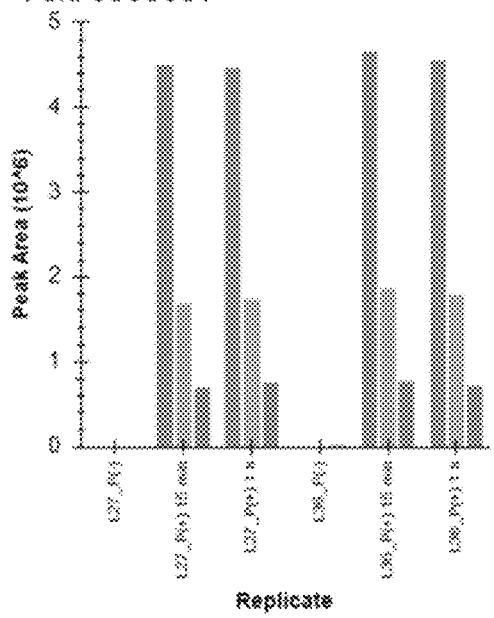
Figure 33C:
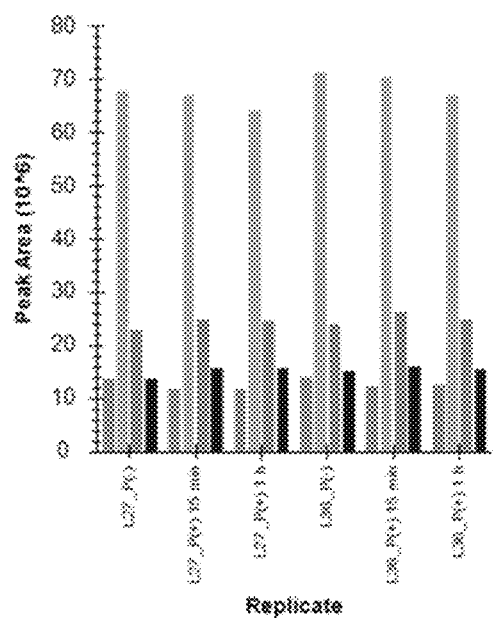
Figure 34A:
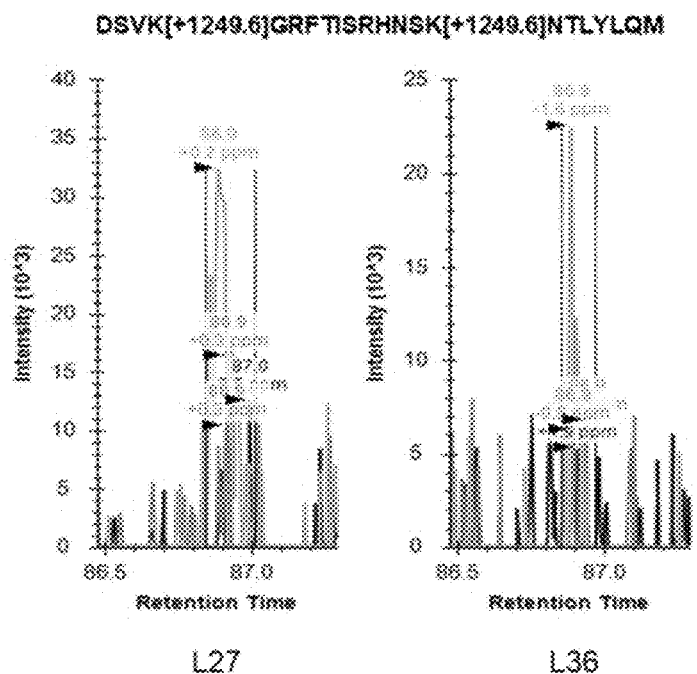
FIGS. 34A-34B show the analysis of drug conjugations on lysine 64 and 75 residues in heavy chain of the antibody (HC*Lys 64 and Lys75) for dual conjugations using papain digestion according to an exemplary embodiment. Figure discloses SEQ ID NOS 21 and 21, respectively, in order of appearance.
Figure 34B:
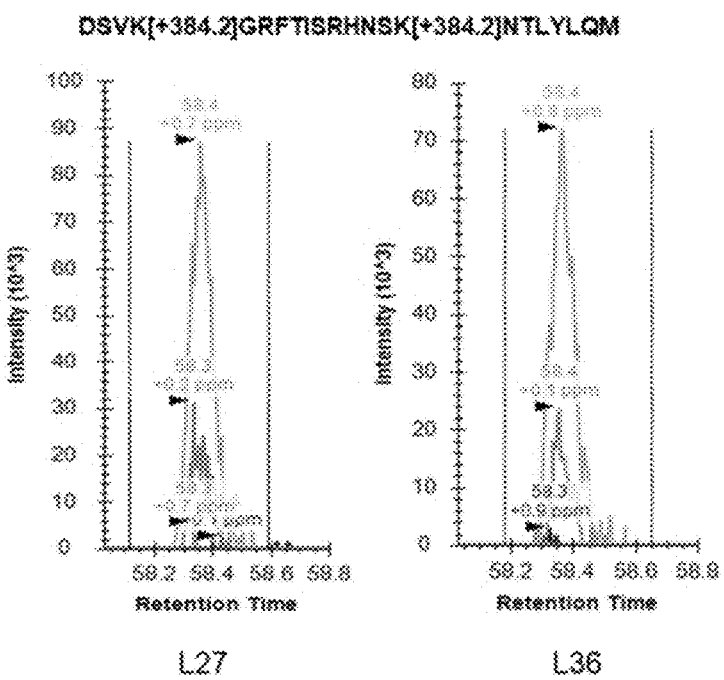
Figure 35A:
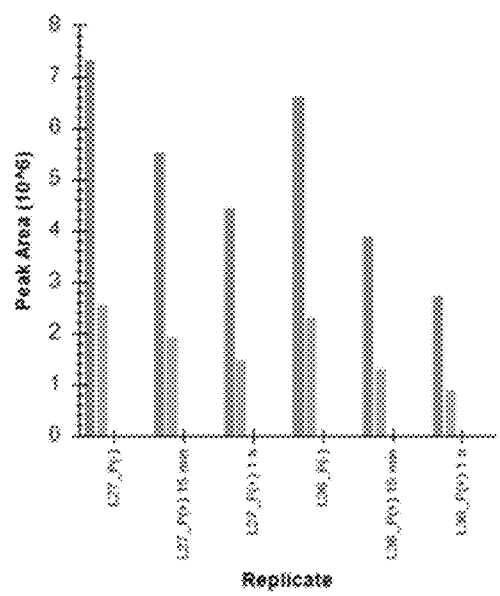
FIGS. 35A-35C show the analysis of drug conjugations on lysine 151 and 147 residues in heavy chain of the antibody (HC Lys151/HC*Lys147) using papain digestion according to an exemplary embodiment. Figure discloses SEQ ID NOS 22, 22, and 22, respectively, in order of appearance.
Figure 35B:
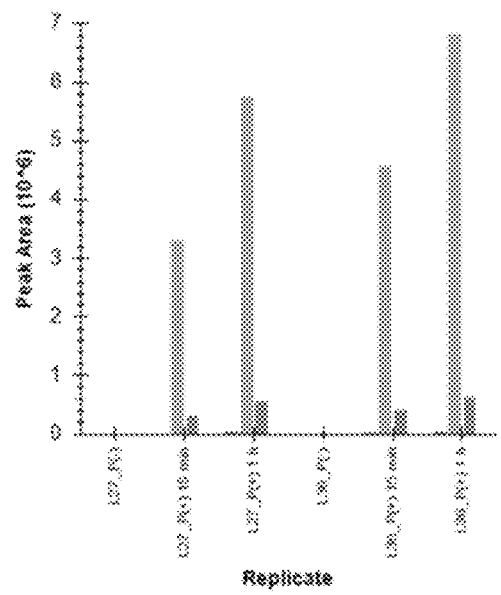
Figure 35C:
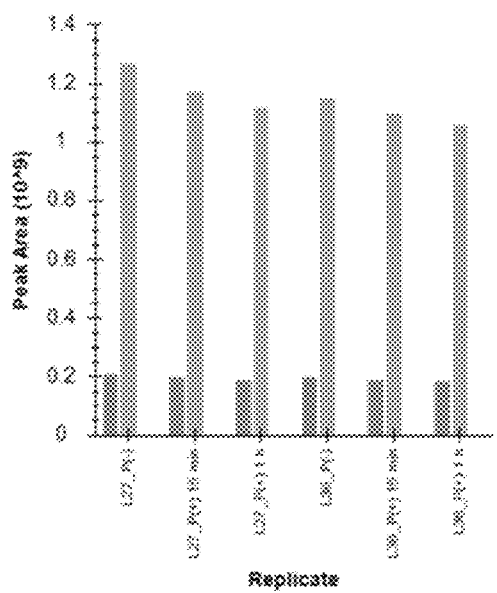

The drug conjugation on lysine 208 residue in light chain of the antibody was analyzed using papain digestion as shown in FIG. 30A, FIG. 30B and FIG. 30C. The results indicated that the completion of drug deconjugation was achieved with slight non-specific cleavage. The drug conjugations on lysine 393 and lysine 389 residues in heavy chain of the antibody (HC Lys393/HC*Lys389) were analyzed using papain digestion as shown in FIG. 31A, FIG. 31B and FIG. 31C. The results indicated that the completion of drug deconjugation was achieved with slight non-specific cleavage. The drug conjugation on lysine 65 residue in light chain of the antibody was analyzed using papain digestion as shown in FIG. 32A, FIG. 32B and FIG. 32C. The results indicated that the completion of drug deconjugation was achieved with slight non-specific cleavage. The drug conjugation on lysine 39, 42 or 45 residue in light chain of the antibody was analyzed using papain digestion by analyzing a peptide containing 55 amino acids as shown in FIG. 33A, FIG. 33B and FIG. 33C. The results indicated that the completion of drug deconjugation was achieved with slight non-specific cleavage. The drug conjugations on lysine 64 and 75 residues in heavy chain of the antibody (HC*Lys 64 and Lys75) for dual conjugations were analyzed using papain digestion as shown in FIG. 34A and FIG. 34B. The results indicated that drug deconjugation can increase the sensitivities of low abundant peptide species. The peak areas of the low abundant peptide species increased greater than 20 fold. The drug conjugations on lysine 151 and 147 residues in heavy chain of the antibody (HC Lys151/HC*Lys147) were analyzed using papain digestion as shown in FIG. 35A, FIG. 35B and FIG. 35C. The results indicated that the drug deconjugation did not reach completion for one peptide.

Figure 36:
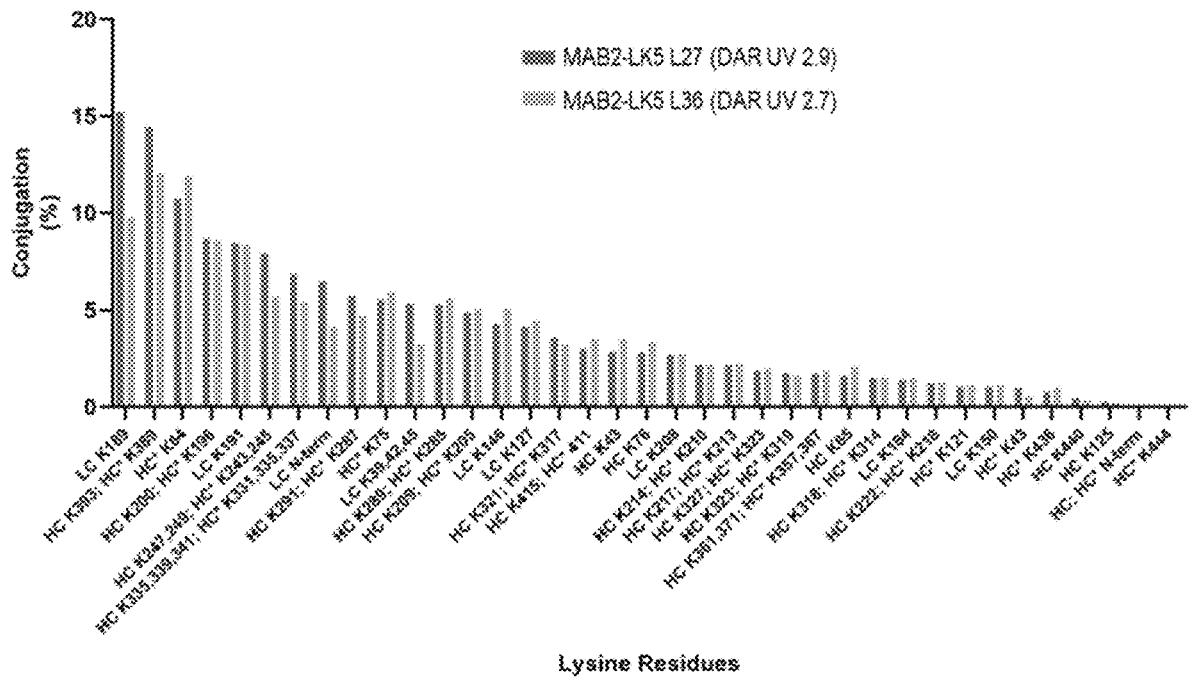
FIG. 36 shows the site-specific quantitation of drug conjugation on various lysine residues for MAB2-LK5 according to an exemplary embodiment.

The drug conjugations were quantitated on 73/79 lysine residues for four chains. The quantitation result of 73/79 lysine residues was about 92.4%. The site-specific quantitation of drug conjugation on various lysine residues for MAB2-LK5 were performed as shown in FIG. 36. The protease-assisted drug deconjugation (PADD) method of the present application allowed efficient and reliable site-specific quantitation of drug conjugation on various lysine residues of lysine-linked ADCs. Average DAR=Sum [conjugation % by unique peptides in HC]+Sum [conjugation % by unique peptides in HC*]+2×Sum [conjugation % in LC+conjugation % in constant peptides in HC and HC*].

What is claimed is:

1. A method for quantifying or characterizing conjugation of at least one attachment linked to at least one specific conjugation site of a partially conjugated antibody or antibody fragment in a sample, comprising:
   obtaining a sample including an antibody or antibody fragment partially conjugated to at least one attachment, wherein the at least one attachment comprises a linker;
   cleaving a portion of the linker to generate an antibody or antibody fragment containing a cleaved linker;
   subjecting the sample to at least one protease to obtain a peptide mixture;
   adding a modified linker to the peptide mixture to obtain a modified peptide mixture, wherein the modified linker labels an unconjugated conjugation site of the partially conjugated antibody or antibody fragment corresponding to the conjugation site of the at least one attachment, and the modified linker is modified to have a molecular weight that is distinguishable from the corresponding cleaved linker using mass analysis;
   subjecting the modified peptide mixture to mass analysis to quantify or characterize the cleaved linker and the modified linker; and
   comparing the quantification or characterization of the cleaved linker to the quantification or characterization of the modified linker to quantify or characterize the conjugation of the at least one attachment.

2. The method of claim 1, wherein the at least one attachment comprises a linker and a payload, wherein the cleaved portion of the attachment comprises the payload and wherein the linker comprises the cleaved linker.

3. The method of claim 1, wherein the mass analysis is conducted using a mass spectrometer, electrospray ionization mass spectrometer, nano-electrospray ionization mass spectrometer or a triple quadrupole mass spectrometer, wherein the mass spectrometer can be coupled to a liquid chromatography system and wherein the mass spectrometer is capable of performing a LC-MS (liquid chromatography-mass spectrometry), a LC-MRM-MS (liquid chromatography-multiple reaction monitoring-mass spectrometry) or a LC-MS/MS analyses.

4. The method of claim 1, further comprising treating the antibody or antibody fragment with an enzyme prior to cleaving the portion of the attachment.

5. The method of claim 1, wherein the portion of the attachment is cleaved using an enzyme, a protease, a chemical, an acid, a base, or a reducing agent.

6. The method of claim 1, wherein the at least one protease is trypsin.

7. The method of claim 1, wherein the portion of the attachment is cleaved using papain, cathepsin B, or plasmin.

8. The method of claim 1, wherein the at least one protease is Glu-C.

9. The method of claim 1, wherein the conjugation site is located within a cysteine residue of the antibody or antibody fragment.

10. The method of claim 1, wherein the attachment is linked to the at least one specific conjugation site through a maleimide attachment group.

11. The method of claim 1, wherein the antibody fragment is a Fab region of an antibody or a Fc region of an antibody.

12. The method of claim 2, wherein the linker is an acid-labile linker, a protease-cleavable linker, a disulfide-containing linker, a pyrophosphate-diester linker, or a hydrazone linker.

13. The method of claim 2, wherein the linker comprises a peptide.

14. The method of claim 2, wherein the linker comprises valine-alanine, phenylalanine-lysine, valine-citrulline, or derivatives thereof.

15. The method of claim 2, wherein the linker comprises polyethylene glycol.

16. The method of claim 2, wherein the linker comprises para-aminobenzyloxycarbonyl (PABC) or para-aminobenzylalcohol (PABA).

17. The method of claim 1, wherein the modified linker comprises polyethylene glycol.

18. The method of claim 1, wherein the modified linker is added to the unconjugated conjugation site through a maleimide attachment group.

19. The method of claim 2, wherein the payload is a drug, a compound, a toxin, a cytotoxic agent, an anti-mitotic agent, a microtubule inhibitor, a DNA-damaging agent, a topoisomerase inhibitor, a RNA polymerase inhibitor, an amanitins analog, a tubu-lysin analog, a chemotherapeutic drug, a microtubule polymerization inhibitor, or a microtubule polymerization promoter.

20. The method of claim 1, wherein the partially conjugated antibody or antibody fragment is selected from the group consisting of a conjugated antibody or antibody fragment of formula I,

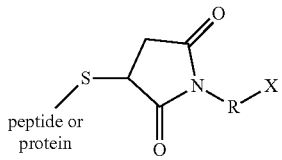

wherein R is a linker, wherein X is a payload.

21. The method of claim 20, wherein the linker comprises polyethylene glycol and wherein the payload is a drug, a compound, a toxin, a cytotoxic agent, an anti-mitotic agent, a microtubule inhibitor, a DNA-damaging agent, a topoisomerase inhibitor, a RNA polymerase inhibitor, an amanitins analog, a tubu-lysin analog, a chemotherapeutic drug, a microtubule polymerization inhibitor, or a microtubule polymerization promoter.

22. The method of claim 1, wherein the partially conjugated antibody or antibody fragment is selected from the group consisting of a conjugated antibody or antibody fragment of formula II,

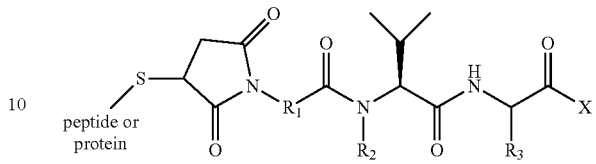

wherein $R_1$ is a spacer, wherein $R_2$ is —H or —$CH_3$, wherein $R_3$ is —$CH_3$, or —$(CH_2)_3NHC(O)NH_2$, wherein X is a payload.

23. The method of claim 22, wherein the spacer comprises polyethylene glycol and wherein the payload is a drug, a compound, a toxin, a cytotoxic agent, an anti-mitotic agent, a microtubule inhibitor, a DNA-damaging agent, a topoisomerase inhibitor, a RNA polymerase inhibitor, an amanitins analog, a tubu-lysin analog, a chemotherapeutic drug, a microtubule polymerization inhibitor, or a microtubule polymerization promoter.

24. The method of claim 1, wherein the partially conjugated antibody or antibody fragment is selected from the group consisting of a conjugated antibody or antibody fragment of formula III,

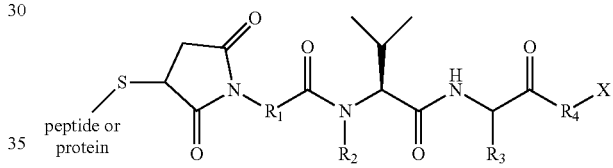

wherein $R_1$ is a first spacer, wherein $R_2$ is —H or —$CH_3$, wherein $R_3$ is —$CH_3$, or —$(CH_2)_3NHC(O)NH_2$, wherein $R_4$ is a second spacer, wherein X is a payload.

25. The method of claim 24, wherein the first spacer comprises polyethylene glycol and wherein the second space comprises para-aminobenzyloxycarbonyl (PABC) or para-aminobenzylalcohol (PABA); wherein the payload is a drug, a compound, a toxin, a cytotoxic agent, an anti-mitotic agent, a microtubule inhibitor, a DNA-damaging agent, a topoisomerase inhibitor, a RNA polymerase inhibitor, an amanitins analog, a tubu-lysin analog, a chemotherapeutic drug, a microtubule polymerization inhibitor, or a microtubule polymerization promoter.

26. The method of claim 1, wherein the conjugation site is located within a lysine residue of the antibody or antibody fragment.

27. The method of claim 1, wherein the step of subjecting the sample to at least one protease comprises a first step of subjecting the sample to at least one first protease to obtain a first peptide mixture, and a second step of subjecting the first peptide mixture to at least one second protease to obtain a second peptide mixture.

28. The method of claim 27, wherein the at least one first protease is trypsin and the at least one second protease is Glu-C.

* * * * *